(12) United States Patent
De Cleyn et al.

(10) Patent No.: US 9,145,399 B2
(45) Date of Patent: Sep. 29, 2015

(54) SUBSTITUTED BICYCLIC TRIAZOLE DERIVATIVES AS GAMMA SECRETASE MODULATORS

(75) Inventors: Michel Anna Jozef De Cleyn, Lille (BE); Sven Franciscus Anna Van Brandt, Nijlen (BE); Henricus Jacobus Maria Gijsen, Breda (NL); Didier Jean-Claude Berthelot, Antwerp (BE); Daniel Oehlrich, Malle (BE)

(73) Assignees: Janssen Pharmaceuticals, Inc., Titusville, NJ (US); Cellzome Limited, Brentford, Middlesex (GB)

( * ) Notice: Subject to any disclaimer, the term of this patent is extended or adjusted under 35 U.S.C. 154(b) by 0 days.

(21) Appl. No.: 13/522,430

(22) PCT Filed: Jan. 12, 2011

(86) PCT No.: PCT/EP2011/050349
§ 371 (c)(1),
(2), (4) Date: Jul. 16, 2012

(87) PCT Pub. No.: WO2011/086098
PCT Pub. Date: Jul. 21, 2011

(65) Prior Publication Data
US 2012/0295901 A1  Nov. 22, 2012

(30) Foreign Application Priority Data
Jul. 29, 2010  (EP) ..................... 10171292

(51) Int. Cl.
C07D 498/04 (2006.01)
A61K 31/5365 (2006.01)
C07D 403/14 (2006.01)
C07D 401/12 (2006.01)
C07D 401/14 (2006.01)
C07D 403/10 (2006.01)
C07D 403/12 (2006.01)
C07D 413/04 (2006.01)

(52) U.S. Cl.
CPC ............ *C07D 403/14* (2013.01); *C07D 401/12* (2013.01); *C07D 401/14* (2013.01); *C07D 403/10* (2013.01); *C07D 403/12* (2013.01); *C07D 413/04* (2013.01)

(58) Field of Classification Search
CPC . C07D 471/04; C07D 498/04; A61K 31/5365
USPC .................. 546/119; 544/91, 105; 514/230.5
See application file for complete search history.

(56) References Cited

U.S. PATENT DOCUMENTS

| | | | |
|---|---|---|---|
| 5,767,144 A | 6/1998 | Winn et al. | |
| 6,114,334 A | 9/2000 | Kerrigan et al. | |
| 7,923,563 B2 | 4/2011 | Kushida et al. | |
| 8,598,353 B2 | 12/2013 | Mjalli et al. | |
| 2002/0128319 A1 | 9/2002 | Koo et al. | |
| 2006/0004013 A1 | 1/2006 | Kimura et al. | |
| 2008/0280948 A1 | 11/2008 | Baumann et al. | |
| 2009/0062529 A1 | 3/2009 | Kimura et al. | |
| 2010/0137320 A1 | 6/2010 | Huang et al. | |

FOREIGN PATENT DOCUMENTS

| | | |
|---|---|---|
| CN | 101142194 | 3/2008 |
| EP | 1757591 | 2/2007 |
| EP | 1992618 A1 | 11/2008 |
| JP | 2003/502313 | 1/2003 |
| WO | WO 01/78721 | 10/2001 |
| WO | WO 01/87845 | 11/2001 |
| WO | WO 02/069946 | 9/2002 |
| WO | WO 2004/017963 | 3/2004 |
| WO | WO 2004/076448 | 9/2004 |
| WO | WO 2004/110350 | 12/2004 |
| WO | WO 2005/016892 | 5/2005 |
| WO | WO 2005/085245 | 9/2005 |
| WO | WO 2005/115990 | 12/2005 |
| WO | WO 2006/135667 | 12/2006 |
| WO | WO 2007/034252 | 3/2007 |

(Continued)

OTHER PUBLICATIONS

International Search Report for PCT/EP2011/050349 dated Feb. 23, 2011.
Citron et al. "Mutant Presenilins of Alzheimer's Disease Increase Production of 42-Residue Amyloid β-Protein in Both Transfected Cells and Transgenic Mice", Nature Medicine, Jan. 1997, 3(1), 67-72.
"Crystallization", Kirk-Othmer Encyclopedia of Chemical Technology, 2002, 8, 95-147.
Dorwald, "Side Reactions in Organic Synthesis", Wiley: VCH Weinheim Preface, Chapter 8, 45 pages.

(Continued)

*Primary Examiner* — Timothy Thomas
(74) *Attorney, Agent, or Firm* — Baker & Hostetler LLP

(57) ABSTRACT

The present invention is concerned with novel substituted bicyclic triazole derivatives of Formula (I)

(I)

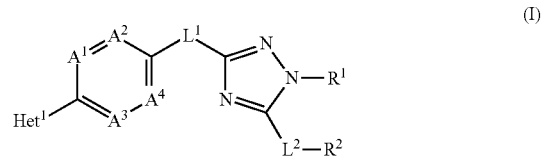

wherein $Het^1$, $R^1$, $R^2$, $A^1$, $A^2$, $A^3$, $A^4$, $L^1$, and $L^2$ have the meaning defined in the claims. The compounds according to the present invention are useful as gamma secretase modulators. The invention further relates to processes for preparing such novel compounds, pharmaceutical compositions comprising said compounds as an active ingredient as well as the use of said compounds as a medicament.

4 Claims, No Drawings

(56) References Cited

FOREIGN PATENT DOCUMENTS

| WO | WO 2007/038314 | 4/2007 |
| --- | --- | --- |
| WO | WO 2007/043786 | 4/2007 |
| WO | WO 2007/044895 | 4/2007 |
| WO | WO 2007/058942 | 5/2007 |
| WO | WO 2007/102580 | 9/2007 |
| WO | WO 2007/105053 | 9/2007 |
| WO | WO 2007/113276 | 10/2007 |
| WO | WO 2007/131991 | 11/2007 |
| WO | WO 2008/065199 | 6/2008 |
| WO | WO 2008/073370 | 6/2008 |
| WO | WO 2008/082490 | 7/2008 |
| WO | WO 2008/097538 | 8/2008 |
| WO | WO 2008/099210 | 8/2008 |
| WO | WO 2008/100412 | 8/2008 |
| WO | WO 2008/137139 | 11/2008 |
| WO | WO 2008/156580 | 12/2008 |
| WO | WO 2009/005729 | 1/2009 |
| WO | WO 2009/028588 | 3/2009 |
| WO | WO 2009/032277 | 3/2009 |
| WO | WO 2009/050227 | 4/2009 |
| WO | WO 2009/073777 | 6/2009 |
| WO | WO 2009/076352 | 6/2009 |
| WO | WO 2009/103652 | 8/2009 |
| WO | WO 2009/155551 | 12/2009 |
| WO | WO 2010/010188 | 1/2010 |
| WO | WO 2010/052199 | 5/2010 |
| WO | WO 2010/054067 | 5/2010 |
| WO | WO 2010/065310 | 6/2010 |
| WO | WO 2010/070008 | 6/2010 |
| WO | WO 2010083141 A1 * | 7/2010 |
| WO | WO 2010/089292 | 8/2010 |
| WO | WO 2010/094647 | 8/2010 |
| WO | WO 2010/098487 | 9/2010 |
| WO | WO 2010/098488 | 9/2010 |
| WO | WO 2010/098495 | 9/2010 |
| WO | WO 2010/100606 | 9/2010 |
| WO | WO 2010/106745 | 9/2010 |
| WO | WO 2010/126745 | 11/2010 |
| WO | WO 2010/137320 | 12/2010 |
| WO | WO 2010/145883 | 12/2010 |
| WO | WO 2011/006903 | 1/2011 |
| WO | WO 2011/086098 | 7/2011 |
| WO | WO 2011/086099 | 7/2011 |
| WO | WO 2012/131539 | 4/2012 |
| WO | WO 2012/126984 | 9/2012 |
| WO | WO 2013/010904 | 1/2013 |

OTHER PUBLICATIONS

Dyatkin et al., "Determination of the Absolute Configuration of a Key Tricyclic Component of a Novel Vasopressin Receptor Antagonist by Use of Vibrational Circular Dichroism", Chirality, 2002, 14, 215-219.

Eriksen et al., "NSAIDs and Enantiomers of Flurbiprofen Target Gamma-Secretase and Lower A-beta-42 In Vivo", J. Clin Invest, 2003, 112(3), 440-449.

Garofalo, "Patents Targeting Gamma-Secretase Inhibition and Modulation for the Treatment of Alzheimer's Disease: 2004-2008", Expert Opinion Ther. Patents, 2008, 18(7), 693-703.

Greene et al., "Protective Groups in Organic Synthesis", John Wiley & Sons, Inc., Third Edition, 1999, 3 pages.

Guillory (Brittain Ed.). "Polymorphism in Pharmaceutical Solids" Marcel Dekker. Inc., NY, 1999, 50 pages.

Jadhav et al. "Ammonium Metavanadate: A Novel Catalyst for Synthesis of 2-Substituted Benzimidazole Derivatives", Chinese Chemical Letters, 2009, 20, 292-295.

Jain et al., "Polymorphism in Pharmacy", Indian Drugs, 1986, 23(6), 315-329.

Larner, "Secretases as Therapeutic Targets in Alzheimer's Disease: Patents 2000-2004", Exp. Opinion Ther. Patents, 2004, 14, 1403-1420.

Marjaux et al., "γ-Secretase Inhibitors: Still in the running as Alzheimer's Therapeutics", Drug Discovery Today: Therapeutics Strategies, 2004, 1(1), 6 pages.

Matthews et al., "A Convenient Procedure for the Preparation of 4(5)-Cyanoimidazoles", J. Org. Chem., 1986 51, 3228-3231.

Moechars et al., "Early Phenotypic Changes in Transgenic Mice That Overexpress Different Mutants of Amyloid Precursor Protein in Brain", J. Biol. Chem., 1999, 274(10), 6483-6492.

Morihara et al., "Selective Inhibition of Aβ42 Production by NSAID R-Enantiomers", Journal of Neurochemistry, 2002, 83, 1009-1012.

Oumata et al., "Roscovitine-Derived, Dual-Specificity Inhibitors of Cyclin-Dependent Kinases and Casein Kinases 1", J. Med. Chem., 2008, 51, 5229-5242.

Peretto et al., "Synthesis and Biological Activity of Fluriprofen Analogues As Selective Inhibitors of β-Amyloid 1-42 Secretion", J Med Chem 2005, 48, 5705.

Schweisguth et al., "Regulation of Notch Signaling Activity", Current Biology, Feb. 3, 2004,14, R129-R138.

Sechi et al., "Design and Synthesis of Novel Indole β-Diketo Acid Derivatives as HIV-1 Integrase Inhibitors", J. Med. Chem., 2004, 47, 5298-5310.

Steiner, "Uncovering γ-Secretase", Current Alzheimer Research, 2004, 1(3), 175-181.

Tanzi et al., "Twenty Years of the Alzheimer's Disease Amyloid Hypothesis: A Genetic Perspective", Cell, 2005, 120, 545-555.

Vippagunta et al., "Crystalline Solids", Advanced Drug Delivery Reviews, 2001, 48, 3-26.

Wang et al., "Preparation of a-Chloroketones by the Chloracetate Claisen Reaction", Synlett, 2000, 6, 902-904.

Weggen et al., "A Subset of NSAIDs Lower Amyloidegenic Aβ42 Independently of Cyclooxygenase Activity", Nature, Nov. 2001, 414, 212-216.

West, "Solid State Chemistry and its Applications", Wiley, New York, 1988, 16 pages (see pp. 358 & 365).

Yu et al. "Physical Characterization of Polymorphic Drugs: An Integrated Characterization Strategy", PSTT, 1998, 1(3), 118-127.

Zettl et al., "Exploring the Chemical Space of γ-Secretase Modulators", Trends in Pharmaceutical Sciences, 2010, 31(9), 402-410.

Wermuth, "Chapter 13—Molecular Variations Based on Isosteric Replacements", The Practice of Medicinal Chemistry, 1996, 35 pages.

* cited by examiner

SUBSTITUTED BICYCLIC TRIAZOLE DERIVATIVES AS GAMMA SECRETASE MODULATORS

CROSS REFERENCE TO RELATED APPLICATIONS

This application is the national stage of PCT Application No. PCT/EP2011/050349, filed Jan. 12, 2011, which claims priority from European Patent Application No. 10150892.7, filed Jan. 15, 2010 and European Patent Application No. 10171292.5, filed Jul. 29, 2010, the entire disclosures of which are hereby incorporated in their entirety.

FIELD OF THE INVENTION

The present invention is concerned with novel substituted bicyclic triazole derivatives useful as gamma secretase modulators. The invention further relates to processes for preparing such novel compounds, pharmaceutical compositions comprising said compounds as an active ingredient as well as the use of said compounds as a medicament.

BACKGROUND OF THE INVENTION

Alzheimer's Disease (AD) is a progressive neurodegenerative disorder marked by loss of memory, cognition, and behavioral stability. AD afflicts 6-10% of the population over age 65 and up to 50% over age 85. It is the leading cause of dementia and the third leading cause of death after cardiovascular disease and cancer. There is currently no effective treatment for AD. The total net cost related to AD in the U.S. exceeds $100 billion annually.

AD does not have a simple etiology, however, it has been associated with certain risk factors including (1) age, (2) family history and (3) head trauma; other factors include environmental toxins and low levels of education. Specific neuropathological lesions in the limbic and cerebral cortices include intracellular neurofibrillary tangles consisting of hyperphosphorylated tau protein and the extracellular deposition of fibrillar aggregates of amyloid beta peptides (amyloid plaques). The major component of amyloid plaques are the amyloid beta (A-beta, Abeta or Aβ) peptides of various lengths. A variant thereof, which is the Aβ1-42-peptide (Abeta-42), is believed to be the major causative agent for amyloid formation. Another variant is the Aβ1-40-peptide (Abeta-40). Aβ is the proteolytic product of a precursor protein, beta amyloid precursor protein (beta-APP or APP).

Familial, early onset autosomal dominant forms of AD have been linked to missense mutations in the β-amyloid precursor protein (β-APP or APP) and in the presenilin proteins 1 and 2. In some patients, late onset forms of AD have been correlated with a specific allele of the apolipoprotein E (ApoE) gene, and, more recently, the finding of a mutation in alpha2-macroglobulin, which may be linked to at least 30% of the AD population. Despite this heterogeneity, all forms of AD exhibit similar pathological findings. Genetic analysis has provided the best clues for a logical therapeutic approach to AD. All mutations found to date, affect the quantitative or qualitative production of the amyloidogenic peptides known as Abeta-peptides (Aβ), specifically Aβ42, and have given strong support to the "amyloid cascade hypothesis" of AD (Tanzi and Bertram, 2005, Cell 120, 545). The likely link between Aβ peptide generation and AD pathology emphasizes the need for a better understanding of the mechanisms of Aβ production and strongly warrants a therapeutic approach at modulating Aβ levels.

The release of Aβ peptides is modulated by at least two proteolytic activities referred to as β- and γ-secretase cleavage at the N-terminus (Met-Asp bond) and the C-terminus (residues 37-42) of the Aβ peptide, respectively. In the secretory pathway, there is evidence that β-secretase cleaves first, leading to the secretion of s-APPβ (sβ) and the retention of a 11 kDa membrane-bound carboxy terminal fragment (CTF). The latter is believed to give rise to Aβ peptides following cleavage by γ-secretase. The amount of the longer isoform, Aβ42, is selectively increased in patients carrying certain mutations in a particular protein (presenilin), and these mutations have been correlated with early-onset familial AD. Therefore, Aβ42 is believed by many researchers to be the main culprit of the pathogenesis of AD.

It has now become clear that the γ-secretase activity cannot be ascribed to a single protein, but is in fact associated with an assembly of different proteins.

The gamma (γ)-secretase activity resides within a multiprotein complex containing at least four components: the presenilin (PS) heterodimer, nicastrin, aph-1 and pen-2. The PS heterodimer consists of the amino- and carboxyterminal PS fragments generated by endoproteolysis of the precursor protein. The two aspartates of the catalytic site are at the interface of this heterodimer. It has recently been suggested that nicastrin serves as a gamma-secretase-substrate receptor. The functions of the other members of gamma-secretase are unknown, but they are all required for activity (Steiner, 2004. Curr. Alzheimer Research 1(3): 175-181).

Thus, although the molecular mechanism of the second cleavage-step has remained elusive until now, the γ-secretase-complex has become one of the prime targets in the search for compounds for the treatment of AD.

Various strategies have been proposed for targeting γ-secretase in AD, ranging from targeting the catalytic site directly, developing substrate-specific inhibitors and modulators of γ-secretase activity (Marjaux et al., 2004. Drug Discovery Today: Therapeutic Strategies, Volume 1, 1-6). Accordingly, a variety of compounds were described that have secretases as targets (Lamer, 2004. Secretases as therapeutics targets in AD: patents 2000-2004. Expert Opin. Ther. Patents 14, 1403-1420).

Indeed, this finding was supported by biochemical studies in which an effect of certain Non-Steroidal Anti-Inflammatory Drugs (NSAIDs) on γ-secretase was shown (US 2002/0128319; Eriksen (2003) J. Clin. Invest. 112, 440). Potential limitations for the use of NSAIDs to prevent or treat AD are their inhibition activity of cyclooxygenase (COX) enzymes, which can lead to unwanted side effects, and their low CNS penetration (Peretto et al., 2005, J. Med. Chem. 48, 5705-5720). More recently the NSAID R-flurbiprofen, an enantiomer lacking Cox-inhibitory activity and related gastric toxicity, has failed in large phase III trial since the drug did not improve thinking ability or the ability of patients to carry out daily activities significantly more than those patients on placebo.

WO-2009/103652 relates to 1H-1,2,4-triazol-3-amine derivatives as modulators for Aβ;

WO-2009/032277 relates to heterocyclic compounds useful as γ secretase modulators;

WO-2009/050227 relates to pyridazine derivatives for inhibiting beta amyloid peptide reduction;

WO-2004/110350 relates to thiazolyl derivatives and their use in modulating Aβ;

WO-2010/010188 relates to [1,2,4]triazolo-[1,5-a]pyridine compounds, including 5-(4-methoxyphenyl)-N-[4-(5-oxazolyl)phenyl]-[1,2,4]triazolo[1,5-c]pyridin-2-amine, 5-(4-methoxyphenyl)-N-[4-(3-pyridinyl)phenyl]-[1,2,4]triazolo[1,5-c]pyridin-2-amine, and 5-(4-methoxyphenyl)-N-[6-(1H-pyrazol-4-yl)-3-pyridinyl]-[1,2,4]triazolo[1,5-a]-pyridin-2-amine, useful for the treatment of degenerative joint diseases and inflammatory diseases;

WO-2010/098495 relates to imidazolylpyrazine derivatives as therapeutic agents for AD;

and WO-2010/083141 relates to bicyclic compounds for the reduction of beta-amyloid production.

There is a strong need for novel compounds which modulate γ-secretase activity thereby opening new avenues for the treatment of AD. It is an object of the present invention to overcome or ameliorate at least one of the disadvantages of the prior art, or to provide a useful alternative. It is accordingly an object of the present invention to provide such novel compounds.

SUMMARY OF THE INVENTION

It has been found that the compounds of the present invention are useful as γ secretase modulators. The compounds according to the invention and the pharmaceutically acceptable compositions thereof, may be useful in the treatment or prevention of AD.

The present invention concerns novel compounds of Formula (I):

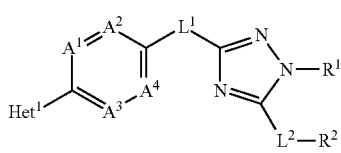

and stereoisomeric forms thereof, wherein
Het$^1$ is a heterocycle, having formula (a-1), (a-2), (a-3), or (a-4)

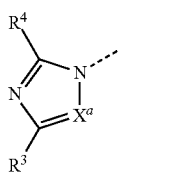         (a-1)

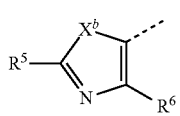         (a-2)

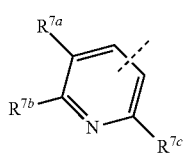         (a-3)

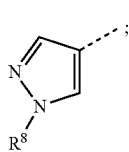         (a-4)

$R^3$ is $C_{1-4}$alkyl;
$R^4$, $R^5$, $R^6$, and $R^8$ each independently are hydrogen or $C_{1-4}$alkyl optionally substituted with one or more halo substituents;
$R^{7a}$ is hydrogen, halo, or $C_{1-4}$alkyl;
$R^{7b}$ and $R^{7c}$ each independently are hydrogen, halo, cyano, $C_{1-4}$alkyloxy, cyclo$C_{3-7}$alkyl, or $C_{1-4}$alkyl optionally substituted with one or more halo substituents;
$X^a$ is CH or N;
$X^b$ is O or S;
$A^1$ is $CR^9$ or N; wherein $R^9$ is hydrogen, halo, or $C_{1-4}$alkyloxy;
$A^2$, $A^3$ and $A^4$ each independently are CH or N;
provided that maximum two of $A^1$, $A^2$, $A^3$ and $A^4$ are N;
$L^1$ is O, carbonyl, $NR^{10}$, NH—(C═O), or (C═O)—NH; wherein $R^{10}$ is hydrogen or $C_{1-4}$alkyl;
$R^1$ and -$L^2$-$R^2$ are taken together to form a bivalent radical —$R^1$—$R^2$-$L^2$- having formula (b-1), (b-2), (b-3), (b-4), (b-5), (b-6), or (b-7)

—(CH$_2$)$_{m-n}$—Y—(CH$_2$)$_n$—     (b-1);

—(CH$_2$)$_n$—Y—(CH$_2$)$_{m-n}$—     (b-2);

—CH═CH—CH═CH—     (b-3);

—CH═CH—N═CH—     (b-4);

—CH═N—CH═CH—     (b-5);

—(CH$_2$)$_{q-r}$—Y—(CH$_2$)$_r$-1,2-benzenediyl-     (b-6);

—(CH$_2$)$_r$—Y—(CH$_2$)$_{q-r}$-1,2-benzenediyl-     (b-7);

wherein (b-1) or (b-2) may contain one unsaturated bond;
wherein (b-1), (b-2) or the radical containing one unsaturated bond, may be substituted on one or more carbon atoms with one or where possible two substituents each independently selected from the group consisting of aryl$^1$, (C═O)-aryl$^1$, O-aryl$^1$, NR$^{13d}$-aryl$^1$, $C_{1-4}$alkylcarbonyl, halo, hydroxy, and $C_{1-4}$alkyl optionally substituted with one or more halo substituents;
wherein (b-3), (b-4), or (b-5) may be substituted where possible with one or more substituents each independently selected from the group consisting of aryl$^1$, 1-piperidinyl, 1-pyrrolidinyl, 4-morpholinyl, (C═O)-aryl$^1$, O-aryl$^1$, NR$^{13f}$-aryl$^1$, $C_{1-4}$alkylcarbonyl, and $C_{1-4}$alkyl optionally substituted with one or more halo substituents;
wherein said 1-piperidinyl, 1-pyrrolidinyl, or 4-morpholinyl may be substituted with one or more trifluoromethyl groups;
wherein (b-6) or (b-7) may be substituted on one or more CH$_2$ groups with one or where possible two substituents each independently selected from the group consisting of aryl$^1$, (C═O)-aryl$^1$, O-aryl$^1$, NR$^{13e}$-aryl$^1$, $C_{1-4}$alkylcarbonyl, halo, hydroxy, and $C_{1-4}$alkyl optionally substituted with one or more halo substituents; and wherein (b-6) or (b-7) may be substituted on the 1,2-benzenediyl-moiety with one or more substituents each independently selected from the group consisting of halo, $C_{1-4}$alkyloxy, cyano, NR$^{11d}$R$^{12d}$, morpholinyl, and $C_{1-4}$alkyl optionally substituted with one or more halo substituents;
Y represents a direct bond, NR$^{14}$ or O; wherein R$^{14}$ is hydrogen, aryl$^1$, (C═O)-aryl$^1$, $C_{1-4}$alkylcarbonyl, or $C_{1-4}$alkyl optionally substituted with one or more halo substituents;
m represents 3 or 4;
n represents 1;
q represents 3, 4, 5 or 6;

r represents 0, 1, 2 or 3;
wherein each aryl$^1$ independently represents phenyl optionally substituted with one or more substituents each independently selected from the group consisting of halo, $C_{1-4}$alkyloxy, cyano, $NR^{11e}R^{12e}$, morpholinyl, and $C_{1-4}$alkyl optionally substituted with one or more halo substituents;

or a 5- or 6-membered heteroaryl selected from the group consisting of furanyl, thiophenyl, pyrazolyl, oxazolyl, isoxazolyl, thiazolyl, isothiazolyl, thiadiazolyl, oxadiazolyl, pyridinyl, pyrimidinyl, pyridazinyl, and pyrazinyl, wherein said 5- or 6-membered heteroaryl may be substituted with one or more substituents each independently selected from the group consisting of halo, $C_{1-4}$alkyloxy, cyano, $NR^{11f}R^{12f}$, morpholinyl, and $C_{1-4}$alkyl optionally substituted with one or more halo substituents;

each $R^{11d}$, $R^{11e}$ and $R^{11f}$ independently is hydrogen, $C_{1-4}$alkyl or $C_{1-4}$alkylcarbonyl;

each $R^{12d}$, $R^{12e}$ and $R^{12f}$ independently is hydrogen or $C_{1-4}$alkyl;

each $R^{13d}$, $R^{13e}$ and $R^{13f}$ independently is hydrogen, or $C_{1-4}$alkyl optionally substituted with one or more substituents each independently selected from the group consisting of halo and cyclo$C_{3-7}$alkyl;

and the pharmaceutically acceptable addition salts, and the solvates thereof; provided that the compound is not 5-(4-methoxyphenyl)-N-[4-(5-oxazolyl)phenyl]-[1,2,4]triazolo[1,5-c]pyridin-2-amine, 5-(4-methoxyphenyl)-N-[4-(3-pyridinyl)phenyl]-[1,2,4]triazolo[1,5-c]pyridin-2-amine, or 5-(4-methoxyphenyl)-N-[6-(1H-pyrazol-4-yl)-3-pyridinyl]-[1,2,4]triazolo[1,5-a]-pyridin-2-amine The present invention also concerns methods for the preparation of compounds of Formula (I) and pharmaceutical compositions comprising them.

The present compounds were found to modulate the γ-secretase activity in vitro and in vivo, and therefore may be useful in the treatment or prevention of AD, traumatic brain injury (TBI), mild cognitive impairment (MCI), senility, dementia, dementia with Lewy bodies, cerebral amyloid angiopathy, multi-infarct dementia, Down's syndrome, dementia associated with Parkinson's disease and dementia associated with beta-amyloid, preferably AD and other disorders with Beta-amyloid pathology (e.g. glaucoma).

In view of the aforementioned pharmacology of the compounds of Formula (I), it follows that they may be suitable for use as a medicament.

More especially the compounds may be suitable in the treatment or prevention of AD, cerebral amyloid angiopathy, multi-infarct dementia, dementia pugilistica or Down syndrome.

The present invention also concerns to the use of a compound according to the general Formula (I), the stereoisomeric forms thereof and the pharmaceutically acceptable acid or base addition salts and the solvates thereof, for the manufacture of a medicament for the modulation of γ-secretase activity.

Use of a compound of Formula (I) for the modulation of γ-secretase activity resulting in a decrease in the relative amount of Aβ42-peptides produced are preferred. One advantage of the compounds or a part of the compounds of the present invention may lie in their enhanced CNS-penetration.

The present invention will now be further described. In the following passages, different aspects of the invention are defined in more detail. Each aspect so defined may be combined with any other aspect or aspects unless clearly indicated to the contrary. In particular, any feature indicated as being preferred or advantageous may be combined with any other feature or features indicated as being preferred or advantageous.

DETAILED DESCRIPTION

When describing the compounds of the invention, the terms used are to be construed in accordance with the following definitions, unless a context dictates otherwise.

Whenever the term "substituted" is used in the present invention, it is meant, unless otherwise is indicated or is clear from the context, to indicate that one or more hydrogens, in particular from 1 to 4 hydrogens, preferably from 1 to 3 hydrogens, more preferably 1 hydrogen, on the atom or radical indicated in the expression using "substituted" are replaced with a selection from the indicated group, provided that the normal valency is not exceeded, and that the substitution results in a chemically stable compound, i.e. a compound that is sufficiently robust to survive isolation to a useful degree of purity from a reaction mixture, and formulation into a therapeutic agent.

The term "halo" as a group or part of a group is generic for fluoro, chloro, bromo, iodo unless otherwise is indicated or is clear from the context.

The term "$C_{1-6}$alkyl" as a group or part of a group refers to a hydrocarbyl radical of Formula $C_nH_{2n+1}$ wherein n is a number ranging from 1 to 6. $C_{1-6}$alkyl groups comprise from 1 to 6 carbon atoms, preferably from 1 to 4 carbon atoms, more preferably from 1 to 3 carbon atoms, still more preferably 1 to 2 carbon atoms. Alkyl groups may be linear or branched and may be substituted as indicated herein. When a subscript is used herein following a carbon atom, the subscript refers to the number of carbon atoms that the named group may contain. Thus, for example, $C_{1-6}$alkyl includes all linear, or branched alkyl groups with between 1 and 6 carbon atoms, and thus includes such as for example methyl, ethyl, n-propyl, i-propyl, 2-methyl-ethyl, butyl and its isomers (e.g. n-butyl, isobutyl and tert-butyl), pentyl and its isomers, hexyl and its isomers, and the like.

The term "$C_{1-4}$alkyl" as a group or part of a group refers to a hydrocarbyl radical of Formula $C_nH_{2n+1}$ wherein n is a number ranging from 1 to 4. $C_{1-4}$alkyl groups comprise from 1 to 4 carbon atoms, preferably from 1 to 3 carbon atoms, more preferably 1 to 2 carbon atoms. $C_{1-4}$alkyl includes all linear, or branched alkyl groups with between 1 and 4 carbon atoms, and thus includes such as for example methyl, ethyl, n-propyl, i-propyl, 2-methyl-ethyl, butyl and its isomers (e.g. n-butyl, isobutyl and tert-butyl), and the like.

The term "$C_{2-6}$alkyl" as a group or part of a group refers to a hydrocarbyl radical of Formula $C_nH_{2n+1}$ wherein n is a number ranging from 2 to 6. $C_{2-6}$alkyl groups comprise from 2 to 6 carbon atoms, in particular from 2 to 4 carbon atoms, more in particular from 2 to 3 carbon atoms. Alkyl groups may be linear or branched and may be substituted as indicated herein. When a subscript is used herein following a carbon atom, the subscript refers to the number of carbon atoms that the named group may contain. Thus, for example, $C_{2-6}$alkyl includes all linear, or branched alkyl groups with between 2 and 6 carbon atoms, and thus includes such as for example ethyl, n-propyl, i-propyl, 2-methyl-ethyl, butyl and its isomers (e.g. n-butyl, isobutyl and tert-butyl), pentyl and its isomers, hexyl and its isomers, and the like.

The term "$C_{1-6}$alkyloxy" as a group or part of a group refers to a radical having the Formula $OR^b$ wherein $R^b$ is $C_{1-6}$alkyl. Non-limiting examples of suitable alkyloxy include methyloxy, ethyloxy, propyloxy, isopropyloxy, butyloxy, isobutyloxy, sec-butyloxy, tert-butyloxy, pentyloxy, and hexyloxy.

The term "$C_{1-4}$alkyloxy" as a group or part of a group refers to a radical having the Formula $OR^c$ wherein $R^c$ is $C_{1-4}$alkyl. Non-limiting examples of suitable $C_{1-4}$alkyloxy include methyloxy (also methoxy), ethyloxy (also ethoxy), propyloxy, isopropyloxy, butyloxy, isobutyloxy, sec-butyloxy and tert-butyloxy.

In the framework of this application, $C_{2-6}$alkenyl is a straight or branched hydrocarbon radical having from 2 to 6 carbon atoms containing a double bond such as ethenyl, propenyl, butenyl, pentenyl, 1-propen-2-yl, hexenyl and the like.

The term "cyclo$C_{3-7}$alkyl" alone or in combination, refers to a cyclic saturated hydrocarbon radical having from 3 to 7 carbon atoms. Non-limiting examples of suitable cyclo$C_{3-7}$alkyl include cyclopropyl, cyclobutyl, cyclopentyl, cyclohexyl and cycloheptyl.

The term "$C_{1-3}$alkanediyl" as a group or part of a group defines bivalent straight or branched chained saturated hydrocarbon radicals having from 1 to 3 carbon atoms such as, for example, methylene or methanediyl, ethan-1,2-diyl, propan-1,3-diyl, propan-1,2-diyl, and the like.

The term "$C_{2-6}$alkanediyl" as a group or part of a group defines bivalent straight or branched chained saturated hydrocarbon radicals having from 2 to 6 carbon atoms such as, for example, ethan-1,2-diyl, propan-1,3-diyl, propan-1,2-diyl, butan-1,4-diyl, pentan-1,5-diyl, hexan-1,6-diyl, 2-methylbutan-1,4-diyl, 3-methylpentan-1,5-diyl and the like.

In a particular embodiment, $C_{1-3}$alkanediyl and $C_{2-6}$alkanediyl defines bivalent straight chained saturated hydrocarbon radicals.

The term "$C_{2-6}$alkenediyl" as a group or part of a group defines bivalent straight and branched chain hydrocarbon radicals containing one double bond and having from 2 to 6 carbon atoms such as, for example, 1,2-ethenediyl, 2-propenediyl, 3-butenediyl, 2-pentenediyl, 3-pentenediyl, 3-methyl-2-butenediyl, and the like.

In a particular embodiment, $C_{2-6}$alkenediyl defines bivalent straight chain hydrocarbon radicals.

The term "thiophenyl" is equivalent to "thienyl".

When $L^1$ is defined as for instance as NH—(C=O), this means that the nitrogen is linked to the 6-membered ring structure containing $A^1$, $A^2$, $A^3$ and $A^4$, and that the carbonyl group is attached to the triazole moiety.

When $L^1$ is defined as for instance as (C=O)—NH, this means that the carbonyl group is linked to the 6-membered ring structure containing $A^1$, $A^2$, $A^3$ and $A^4$, and that the nitrogen is attached to the triazole moiety.

The symbol "—" denotes the point of attachment to the remainder of the molecule.

The chemical names of the compounds of the present invention were generated according to the nomenclature rules agreed upon by the Chemical Abstracts Service, using Advanced Chemical Development, Inc., nomenclature software (ACD/Name product version 10.01; Build 15494, 1 Dec. 2006).

In case of tautomeric forms, it should be clear that the other non-depicted tautomeric form is also included within the scope of the present invention.

When any variable occurs more than one time in any constituent, each definition is independent.

It will be appreciated that some of the compounds of Formula (I) and their pharmaceutically acceptable addition salts and stereoisomeric forms may contain one or more centers of chirality and exist as stereoisomeric forms.

The term "stereoisomeric forms" as used hereinbefore defines all the possible isomeric forms that the compounds of Formula (I) may possess. Unless otherwise mentioned or indicated, the chemical designation of compounds denotes the mixture of all possible stereochemically isomeric forms. More in particular, stereogenic centers may have the R- or S-configuration; substituents on bivalent cyclic (partially) saturated radicals may have either the cis- or trans-configuration. Compounds encompassing double bonds can have an E or Z-stereochemistry at said double bond. Stereoisomeric forms of the compounds of Formula (I) are embraced within the scope of this invention.

When a specific stereoisomeric form is indicated, this means that said form is substantially free, i.e. associated with less than 50%, preferably less than 20%, more preferably less than 10%, even more preferably less than 5%, further preferably less than 2% and most preferably less than 1% of the other isomer(s).

When a specific regioisomeric form is indicated, this means that said form is substantially free, i.e. associated with less than 50%, preferably less than 20%, more preferably less than 10%, even more preferably less than 5%, further preferably less than 2% and most preferably less than 1% of the other isomer(s).

For therapeutic use, salts of the compounds of Formula (I) are those wherein the counterion is pharmaceutically acceptable. However, salts of acids and bases which are non-pharmaceutically acceptable may also find use, for example, in the preparation or purification of a pharmaceutically acceptable compound. All salts, whether pharmaceutically acceptable or not are included within the ambit of the present invention.

The pharmaceutically acceptable acid and base addition salts as mentioned hereinabove or hereinafter are meant to comprise the therapeutically active non-toxic acid and base addition salt forms which the compounds of Formula (I) are able to form. The pharmaceutically acceptable acid addition salts can conveniently be obtained by treating the base form with such appropriate acid. Appropriate acids comprise, for example, inorganic acids such as hydrohalic acids, e.g. hydrochloric or hydrobromic acid, sulfuric, nitric, phosphoric and the like acids; or organic acids such as, for example, acetic, propanoic, hydroxyacetic, lactic, pyruvic, oxalic (i.e. ethanedioic), malonic, succinic (i.e. butanedioic acid), maleic, fumaric, malic, tartaric, citric, methanesulfonic, ethanesulfonic, benzenesulfonic, p-toluenesulfonic, cyclamic, salicylic, p-aminosalicylic, pamoic and the like acids. Conversely said salt forms can be converted by treatment with an appropriate base into the free base form.

The compounds of Formula (I) containing an acidic proton may also be converted into their non-toxic metal or amine addition salt forms by treatment with appropriate organic and inorganic bases. Appropriate base salt forms comprise, for example, the ammonium salts, the alkali and earth alkaline metal salts, e.g. the lithium, sodium, potassium, magnesium, calcium salts and the like, salts with organic bases, e.g. primary, secondary and tertiary aliphatic and aromatic amines such as methylamine, ethylamine, propylamine, isopropylamine, the four butylamine isomers, dimethylamine, diethylamine, diethanolamine, dipropylamine, diisopropylamine, di-n-butylamine, pyrrolidine, piperidine, morpholine, trimethylamine, triethylamine, tripropylamine, quinuclidine, pyridine, quinoline and isoquinoline; the benzathine, N-methyl-D-glucamine, hydrabamine salts, and salts with amino acids such as, for example, arginine, lysine and the like. Conversely the salt form can be converted by treatment with acid into the free acid form.

The term solvate comprises the hydrates and solvent addition forms which the compounds of Formula (I) are able to form, as well as the salts thereof. Examples of such forms are e.g. hydrates, alcoholates and the like.

The compounds of Formula (I) as prepared in the processes described below may be synthesized in the form of racemic mixtures of enantiomers that can be separated from one another following art-known resolution procedures. An manner of separating the enantiomeric forms of the compounds of Formula (I) involves liquid chromatography using a chiral stationary phase. Said pure stereochemically isomeric forms may also be derived from the corresponding pure stereochemically isomeric forms of the appropriate starting materials, provided that the reaction occurs stereospecifically. Preferably if a specific stereoisomer is desired, said compound would be synthesized by stereospecific methods of preparation. These methods will advantageously employ enantiomerically pure starting materials.

The compounds of Formula (I), or part of the compounds of the present invention may have improved solubility compared with compounds disclosed in the prior art.

In the framework of this application, a compound according to the invention is inherently intended to comprise all isotopic combinations of its chemical elements. In the framework of this application, a chemical element, in particular when mentioned in relation to a compound according to Formula (I), comprises all isotopes and isotopic mixtures of this element. For example, when hydrogen is mentioned, it is understood to refer to $^1H$, $^2H$, $^3H$ and mixtures thereof.

A compound according to the invention therefore inherently comprises a compound with one or more isotopes of one or more element, and mixtures thereof, including a radioactive compound, also called radiolabelled compound, wherein one or more non-radioactive atoms has been replaced by one of its radioactive isotopes. By the term "radiolabelled compound" is meant any compound according to Formula (I), or a pharmaceutically acceptable salt thereof, which contains at least one radioactive atom. For example, a compound can be labelled with positron or with gamma emitting radioactive isotopes. For radioligand-binding techniques, the $^3H$-atom or the $^{125}I$-atom is the atom of choice to be replaced. For imaging, the most commonly used positron emitting (PET) radioactive isotopes are $^{11}C$, $^{18}F$, $^{15}O$ and $^{13}N$, all of which are accelerator produced and have half-lives of 20, 100, 2 and 10 minutes (min) respectively. Since the half-lives of these radioactive isotopes are so short, it is only feasible to use them at institutions which have an accelerator on site for their production, thus limiting their use. The most widely used of these are $^{18}F$, $^{99m}Tc$, $^{201}Tl$ and $^{123}I$. The handling of these radioactive isotopes, their production, isolation and incorporation in a molecule are known to the skilled person.

In particular, the radioactive atom is selected from the group of hydrogen, carbon, nitrogen, sulfur, oxygen and halogen. In particular, the radioactive isotope is selected from the group of $^3H$, $^{11}C$, $^{18}F$, $^{122}I$, $^{123}I$, $^{125}I$, $^{131}I$, $^{75}Br$, $^{76}Br$, $^{77}Br$ and $^{82}Br$.

As used in the specification and the appended claims, the singular forms "a", "an," and "the" also include plural referents unless the context clearly dictates otherwise. For example, "a compound" means 1 compound or more than 1 compound.

The terms described above and others used in the specification are well understood to those in the art.

Preferred features of the compounds of this invention are now set forth.

In an embodiment, the present invention concerns novel compounds of Formula (I):

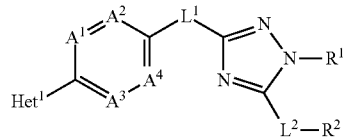

and stereoisomeric forms thereof, wherein
Het$^1$ is a heterocycle, having formula (a-1), (a-2), (a-3a), or (a-4)

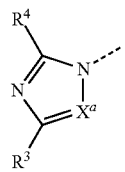

(a-1)

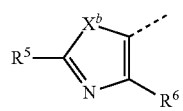

(a-2)

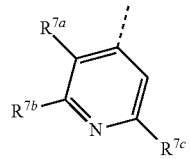

(a-3a)

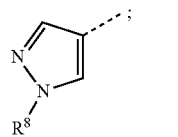

(a-4)

R$^3$ is C$_{1-4}$alkyl;
R$^4$, R$^5$, R$^6$, and R$^8$ each independently are hydrogen or C$_{1-4}$alkyl optionally substituted with one or more halo substituents;
R$^{7a}$ is hydrogen, halo, or C$_{1-4}$alkyl;
R$^{7b}$ and R$^{7c}$ each independently are hydrogen, halo, cyano, C$_{1-4}$alkyloxy, cycloC$_{3-7}$alkyl, or C$_{1-4}$alkyl optionally substituted with one or more halo substituents;
X$^a$ is CH or N;
X$^b$ is O or S;
A$^1$ is CR$^9$ or N; wherein R$^9$ is hydrogen, halo, or C$_{1-4}$alkyloxy;
A$^2$, A$^3$ and A$^4$ each independently are CH or N;
provided that maximum two of A$^1$, A$^2$, A$^3$ and A$^4$ are N;
L$^1$ is O, carbonyl, NR$^{10}$, NH—(C═O), or (C═O)—NH; wherein R$^{10}$ is hydrogen or C$_{1-4}$alkyl;
R$^1$ and -L$^2$-R$^2$ are taken together to form a bivalent radical —R$^1$-R$^2$-L$^2$- having formula (b-1), (b-2), (b-3), (b-4), (b-5), (b-6), or (b-7)

—(CH$_2$)$_{m-n}$—Y—(CH$_2$)$_n$— (b-1);

—(CH$_2$)$_n$—Y—(CH$_2$)$_{m-n}$— (b-2);

—CH═CH—CH═CH— (b-3);

—CH═CH—N═CH— (b-4);

—CH═N—CH═CH— (b-5);

—(CH₂)$_{q-r}$—Y—(CH₂)$_r$-1,2-benzenediyl- (b-6);

—(CH₂)$_r$—Y—(CH₂)$_{q-r}$-1,2-benzenediyl- (b-7);

wherein (b-1) or (b-2) may contain one unsaturated bond;
wherein (b-1), (b-2) or the radical containing one unsaturated bond, may be substituted on one or more carbon atoms with one or where possible two substituents each independently selected from the group consisting of aryl¹, (C═O)-aryl¹, O-aryl¹, NR$^{13d}$-aryl¹, C$_{1-4}$alkylcarbonyl, halo, hydroxy, and C$_{1-4}$alkyl optionally substituted with one or more halo substituents;
wherein (b-3), (b-4), or (b-5) may be substituted where possible with one or more substituents each independently selected from the group consisting of aryl¹, 1-piperidinyl, 1-pyrrolidinyl, 4-morpholinyl, (C═O)-aryl¹, O-aryl¹, NR$^{13f}$-aryl¹, C$_{1-4}$alkylcarbonyl, and C$_{1-4}$alkyl optionally substituted with one or more halo substituents;
wherein said 1-piperidinyl, 1-pyrrolidinyl, or 4-morpholinyl may be substituted with one or more trifluoromethyl groups;
wherein (b-6) or (b-7) may be substituted on one or more CH₂ groups with one or where possible two substituents each independently selected from the group consisting of aryl¹, (C═O)-aryl¹, O-aryl¹, NR$^{13e}$-aryl¹, C$_{1-4}$alkylcarbonyl, halo, hydroxy, and C$_{1-4}$alkyl optionally substituted with one or more halo substituents; and wherein (b-6) or (b-7) may be substituted on the 1,2-benzenediyl-moiety with one or more substituents each independently selected from the group consisting of halo, C$_{1-4}$alkyloxy, cyano, NR$^{11d}$R$^{12d}$, morpholinyl, and C$_{1-4}$alkyl optionally substituted with one or more halo substituents;
Y represents a direct bond, NR¹⁴ or O; wherein R¹⁴ is hydrogen, aryl¹, (C═O)-aryl¹, C$_{1-4}$alkylcarbonyl, or C$_{1-4}$alkyl optionally substituted with one or more halo substituents;
m represents 3 or 4;
n represents 1;
q represents 3, 4, 5 or 6;
r represents 0, 1, 2 or 3;
aryl¹ represents phenyl optionally substituted with one or more substituents each independently selected from the group consisting of halo, C$_{1-4}$alkyloxy, cyano, NR$^{11e}$R$^{12e}$, morpholinyl, and C$_{1-4}$alkyl optionally substituted with one or more halo substituents;
or a 5- or 6-membered heteroaryl selected from the group consisting of furanyl, thiophenyl, pyrazolyl, oxazolyl, isoxazolyl, thiazolyl, isothiazolyl, thiadiazolyl, oxadiazolyl, pyridinyl, pyrimidinyl, pyridazinyl, and pyrazinyl, wherein said 5- or 6-membered heteroaryl may be substituted with one or more substituents each independently selected from the group consisting of halo, C$_{1-4}$alkyloxy, cyano, NR$^{11f}$R$^{12f}$, morpholinyl, and C$_{1-4}$alkyl optionally substituted with one or more halo substituents;
each R$^{11d}$, R$^{11e}$ and R$^{11f}$ independently is hydrogen, C$_{1-4}$alkyl or C$_{1-4}$alkylcarbonyl;
each R$^{12d}$, R$^{12e}$ and R$^{12f}$ independently is hydrogen or C$_{1-4}$alkyl;
each R$^{13d}$, R$^{13e}$ and R$^{13f}$ independently is hydrogen, or C$_{1-4}$alkyl optionally substituted with one or more substituents each independently selected from the group consisting of halo and cycloC$_{3-7}$alkyl;
and the pharmaceutically acceptable addition salts, and the solvates thereof; provided that the compound is not 5-(4-methoxyphenyl)-N-[4-(5-oxazolyl)phenyl]-[1,2,4]triazolo[1,5-c]pyridin-2-amine or 5-(4-methoxyphenyl)-N-[6-(1H-pyrazol-4-yl)-3-pyridinyl]-[1,2,4]triazolo[1,5-a]-pyridin-2-amine In an embodiment, the present invention relates to those compounds of Formula (I) and stereoisomeric forms thereof wherein
Het¹ is a heterocycle, having formula (a-1), (a-2), (a-3a), or (a-4)

(a-1)

(a-2)

(a-3a)

(a-4)

R³ is C$_{1-4}$alkyl;
R⁴, R⁵, R⁶, and R⁸ each independently are hydrogen or C$_{1-4}$alkyl optionally substituted with one or more halo substituents;
R$^{7a}$ is hydrogen, halo, or C$_{1-4}$alkyl;
R$^{7b}$ and R$^{7c}$ each independently are hydrogen, halo, cyano, C$_{1-4}$alkyloxy, cycloC$_{3-7}$alkyl, or C$_{1-4}$alkyl optionally substituted with one or more halo substituents;
X$^a$ is CH or N;
X$^b$ is O or S;
A¹ is CR⁹ or N; wherein R⁹ is hydrogen, halo, or C$_{1-4}$alkyloxy;
A², A³ and A⁴ each independently are CH or N;
provided that maximum two of A¹, A², A³ and A⁴ are N;
L¹ is O, carbonyl, NR¹⁰, NH—(C═O), or (C═O)—NH; wherein R¹⁰ is hydrogen or C$_{1-4}$alkyl;
R¹ and -L²-R² are taken together to form a bivalent radical —R¹—R²-L²- having formula (b-1), (b-2), (b-3), (b-4), (b-5), (b-6), or (b-7)

—(CH₂)$_{m-n}$—Y—(CH₂)$_n$— (b-1);

—(CH₂)$_n$—Y—(CH₂)$_{m-n}$— (b-2);

—CH═CH—CH═CH— (b-3);

—CH═CH—N═CH— (b-4);

—CH═N—CH═CH— (b-5);

—(CH₂)$_{q-r}$—Y—(CH₂)$_r$-1,2-benzenediyl- (b-6);

—(CH₂)$_r$—Y—(CH₂)$_{q-r}$-1,2-benzenediyl- (b-7);

wherein (b-1) or (b-2) may contain one unsaturated bond;
wherein (b-1), (b-2) or the radical containing one unsaturated bond, may be substituted on one or more carbon atoms with one or where possible two substituents each independently selected from the group consisting of aryl$^1$, (C=O)-aryl$^1$, O-aryl$^1$, NR$^{13d}$-aryl$^1$, C$_{1-4}$alkylcarbonyl, halo, hydroxy, and C$_{1-4}$alkyl optionally substituted with one or more halo substituents;
wherein (b-3), (b-4), or (b-5) may be substituted where possible with one or more substituents each independently selected from the group consisting of aryl$^1$, (C=O)-aryl$^1$, O-aryl$^1$, NR$^{13f}$-aryl$^1$, C$_{1-4}$alkylcarbonyl, and C$_{1-4}$alkyl optionally substituted with one or more halo substituents;
wherein (b-6) or (b-7) may be substituted on one or more CH$_2$ groups with one or where possible two substituents each independently selected from the group consisting of aryl$^1$, (C=O)-aryl$^1$, O-aryl$^1$, NR$^{13e}$-aryl$^1$, C$_{1-4}$alkylcarbonyl, halo, hydroxy, and C$_{1-4}$alkyl optionally substituted with one or more halo substituents; and wherein (b-6) or (b-7) may be substituted on the 1,2-benzenediyl-moiety with one or more substituents each independently selected from the group consisting of halo, C$_{1-4}$alkyloxy, cyano, NR$^{11d}$R$^{12d}$, morpholinyl, and C$_{1-4}$alkyl optionally substituted with one or more halo substituents;
Y represents a direct bond, NR$^{14}$ or O; wherein R$^{14}$ is hydrogen, aryl$^1$, (C=O)-aryl$^1$, C$_{1-4}$alkylcarbonyl, or C$_{1-4}$alkyl optionally substituted with one or more halo substituents;
m represents 3 or 4;
n represents 1;
q represents 3, 4, 5 or 6;
r represents 0, 1, 2 or 3;
aryl$^1$ represents phenyl optionally substituted with one or more substituents each independently selected from the group consisting of halo, C$_{1-4}$alkyloxy, cyano, NR$^{11e}$R$^{12e}$, morpholinyl, and C$_{1-4}$alkyl optionally substituted with one or more halo substituents; or a 5- or 6-membered heteroaryl selected from the group consisting of furanyl, thiophenyl, pyrazolyl, oxazolyl, isoxazolyl, thiazolyl, isothiazolyl, thiadiazolyl, oxadiazolyl, pyridinyl, pyrimidinyl, pyridazinyl, and pyrazinyl, wherein said 5- or 6-membered heteroaryl may be substituted with one or more substituents each independently selected from the group consisting of halo, C$_{1-4}$alkyloxy, cyano, NR$^{11f}$R$^{12f}$, morpholinyl, and
C$_{1-4}$alkyl optionally substituted with one or more halo substituents;
each R$^{11d}$, R$^{11e}$ and R$^{11f}$ independently is hydrogen, C$_{1-4}$alkyl or C$_{1-4}$alkylcarbonyl;
each R$^{12d}$, R$^{12e}$ and R$^{12f}$ independently is hydrogen or C$_{1-4}$alkyl;
each R$^{13d}$, R$^{13e}$ and R$^{13f}$ independently is hydrogen, or C$_{1-4}$alkyl optionally substituted with one or more substituents each independently selected from the group consisting of halo and cycloC$_{3-7}$alkyl;
and the pharmaceutically acceptable addition salts, and the solvates thereof; provided that the compound is not 5-(4-methoxyphenyl)-N-[4-(5-oxazolyl)phenyl]-[1,2,4]triazolo[1,5-c]pyridin-2-amine or 5-(4-methoxyphenyl)-N-[6-(1H-pyrazol-4-yl)-3-pyridinyl]-[1,2,4]triazolo[1,5-a]-pyridin-2-amine
In an embodiment, the present invention concerns novel compounds of Formula (I) and stereoisomeric forms thereof, wherein Het$^1$ is a heterocycle, having formula (a-1), (a-2), (a-3a), or (a-4)

(a-1)

(a-2)

(a-3a)

(a-4)

R$^3$ is C$_{1-4}$alkyl;
R$^4$, R$^5$, R$^6$, and R$^8$ each independently are hydrogen or C$_{1-4}$alkyl optionally substituted with one or more halo substituents;
R$^{7a}$ is hydrogen, halo, or C$_{1-4}$alkyl;
R$^{7b}$ and R$^{7c}$ each independently are hydrogen, halo, cyano, C$_{1-4}$alkyloxy, cycloC$_{3-7}$alkyl, or C$_{1-4}$alkyl optionally substituted with one or more halo substituents;
X$^a$ is CH or N;
X$^b$ is O or S;
A$^1$ is CR$^9$ or N; wherein R$^9$ is hydrogen, halo, or C$_{1-4}$alkyloxy;
A$^2$, A$^3$ and A$^4$ each independently are CH or N;
provided that maximum two of A$^1$, A$^2$, A$^3$ and A$^4$ are N;
L$^1$ is O, carbonyl, NR$^{10}$, NH—(C=O), or (C=O)—NH; wherein R$^{16}$ is hydrogen or C$_{1-4}$alkyl;
R$^1$ and -L$^2$-R$^2$ are taken together to form a bivalent radical —R$^1$—R$^2$-L$^2$- having formula (b-1), (b-2), (b-3), (b-4), (b-5), (b-6), or (b-7)

—(CH$_2$)$_{m-n}$—Y—(CH$_2$)$_n$—     (b-1);

—(CH$_2$)$_n$—Y—(CH$_2$)$_{m-n}$—     (b-2);

—CH=CH—CH=CH—     (b-3);

—CH=CH—N=CH—     (b-4);

—CH=N—CH=CH—     (b-5);

—(CH$_2$)$_{q-r}$—Y—(CH$_2$)$_r$-1,2-benzenediyl-     (b-6);

—(CH$_2$)$_r$—Y—(CH$_2$)$_{q-r}$-1,2-benzenediyl-     (b-7);

wherein (b-1) or (b-2) may contain one unsaturated bond;
wherein (b-1), (b-2) or the radical containing one unsaturated bond, may be substituted on one or more carbon atoms with one or where possible two substituents each independently selected from the group consisting of aryl¹, aryl¹-carbonyl, aryl¹-O, aryl¹-NR¹³ᵈ, $C_{1-4}$alkyl-carbonyl, halo, hydroxy, and $C_{1-4}$alkyl optionally substituted with one or more halo substituents;
  wherein (b-3), (b-4), or (b-5) may be substituted where possible with one or more substituents each independently selected from the group consisting of aryl¹, aryl¹-carbonyl, aryl¹-O, aryl¹-NR¹³ᶠ, $C_{1-4}$alkylcarbonyl, and $C_{1-4}$alkyl optionally substituted with one or more halo substituents;
  wherein (b-6) or (b-7) may be substituted on one or more $CH_2$ groups with one or where possible two substituents each independently selected from the group consisting of aryl¹, aryl¹-carbonyl, aryl¹-O, aryl¹-NR¹³ᵉ,
    $C_{1-4}$alkylcarbonyl, halo, hydroxy, and $C_{1-4}$alkyl optionally substituted with one or more halo substituents; and wherein (b-6) or (b-7) may be substituted on the 1,2-benzenediyl-moiety with one or more substituents each independently selected from the group consisting of halo, $C_{1-4}$alkyloxy, cyano, NR¹¹ᵈR¹²ᵈ, morpholinyl, and $C_{1-4}$alkyl optionally substituted with one or more halo substituents;
Y represents a direct bond, NR¹⁴ or O; wherein R¹⁴ is hydrogen, aryl¹, aryl¹-carbonyl, $C_{1-4}$alkylcarbonyl, or $C_{1-4}$alkyl optionally substituted with one or more halo substituents;
m represents 3 or 4;
n represents 1;
q represents 3, 4, 5 or 6;
r represents 0, 1, 2 or 3;
aryl¹ represents phenyl optionally substituted with one or more substituents each independently selected from the group consisting of halo, $C_{1-4}$alkyloxy, cyano, NR¹¹ᵉR¹²ᵉ, morpholinyl, and $C_{1-4}$alkyl optionally substituted with one or more halo substituents; or a 5- or 6-membered heteroaryl selected from the group consisting of pyridinyl, pyrimidinyl, oxazolyl, furanyl, thiophenyl, pyrazolyl, morpholinyl, isoxazolyl, thiazolyl, isothiazolyl, thiadiazolyl, oxadiazolyl, pyridazinyl, and pyrazinyl, wherein said 5- or 6-membered heteroaryl may be substituted with one or more substituents each independently selected from the group consisting of halo, $C_{1-4}$alkyloxy, cyano, NR¹¹ᶠR¹²ᶠ, morpholinyl, and $C_{1-4}$alkyl optionally substituted with one or more halo substituents;
each R¹¹ᵈ, R¹¹ᵉ and R¹¹ᶠ independently is hydrogen, $C_{1-4}$alkyl or $C_{1-4}$alkylcarbonyl;
each R¹²ᵈ, R¹²ᵉ and R¹²ᶠ independently is hydrogen or $C_{1-4}$alkyl;
each R¹³ᵈ, R¹³ᵉ and R¹³ᶠ independently is hydrogen, or $C_{1-4}$alkyl optionally substituted with one or more substituents each independently selected from the group consisting of halo and cyclo$C_{3-7}$alkyl;
and the pharmaceutically acceptable addition salts, and the solvates thereof;
provided that the compound is not 5-(4-methoxyphenyl)-N-[4-(5-oxazolyl)phenyl]-[1,2,4]triazolo[1,5-a]pyridin-2-amine An embodiment of the present invention relates to those compounds of Formula (I) and stereoisomeric forms thereof, or any subgroup thereof as mentioned in any of the other embodiments, wherein one or more of the following restrictions apply:
(i) Het¹ is a heterocycle, having formula (a-1), (a-2), or (a-3);
(ii) R³ is $C_{1-4}$alkyl;
(iii) R⁴, R⁵, and R⁶ each independently are hydrogen or $C_{1-4}$alkyl optionally substituted with one or more halo substituents;
(iv) R⁷ᵃ is hydrogen, halo, or $C_{1-4}$alkyl;
  R⁷ᵇ and R⁷ᶜ each independently are hydrogen, halo, cyano, $C_{1-4}$alkyloxy, or $C_{1-4}$alkyl optionally substituted with one or more halo substituents;
(v) R¹ and -L²-R² taken together form a bivalent radical —R¹—R²-L²- having formula (b-1), (b-2), (b-3), (b-4), (b-5), (b-6), or (b-7); in particular (b-1), (b-2), (b-3), (b-4), or (b-5); more in particular (b-1), (b-2), or (b-3);
  wherein (b-1) or (b-2) is substituted on one carbon atom with one aryl¹ group, and optionally (b-1) or (b-2) is further substituted on one or more of the other carbon atoms with in total one or two substituents each independently selected from the group consisting of $C_{1-4}$alkylcarbonyl, halo, hydroxy, and $C_{1-4}$alkyl optionally substituted with one or more halo substituents; in particular wherein (b-1) or (b-2) is substituted on one carbon atom with one aryl¹ group and optionally (b-1) or (b-2) is further substituted on one of the other carbon atoms with one $C_{1-4}$alkyl substituent;
  wherein (b-3), (b-4), or (b-5) are substituted with one aryl¹ substituent;
(vi) Y represents a direct bond, NR¹⁴ or O; in particular NR¹⁴ or O;
  wherein R¹⁴ is hydrogen, $C_{1-4}$alkylcarbonyl, or $C_{1-4}$alkyl optionally substituted with one or more halo substituents;
(vii) m represents 3 or 4;
(viii) n represents 1;
(ix) aryl¹ represents phenyl optionally substituted with one or more substituents each independently selected from the group consisting of halo, $C_{1-4}$alkyloxy, cyano, NR¹¹ᵉR¹²ᵉ, morpholinyl, and $C_{1-4}$alkyl optionally substituted with one or more halo substituents;
(x) each R¹¹ᵉ independently is hydrogen, $C_{1-4}$alkyl or $C_{1-4}$alkylcarbonyl;
(xi) each R¹²ᵉ independently is hydrogen or $C_{1-4}$alkyl.

In an embodiment, the present invention relates to those compounds of Formula (I) and stereoisomeric forms thereof wherein
Het¹ is a heterocycle, having formula (a-1), (a-2), or (a-3);
R³ is $C_{1-4}$alkyl; in particular methyl;
R⁴ is hydrogen;
R⁵ is hydrogen or $C_{1-4}$alkyl; in particular hydrogen or methyl;
R⁶ is hydrogen or $C_{1-4}$alkyl; in particular hydrogen or methyl;
R⁷ᵃ is hydrogen or $C_{1-4}$alkyl; in particular hydrogen or methyl;
R⁷ᵇ is hydrogen, $C_{1-4}$alkyloxy, or $C_{1-4}$alkyl optionally substituted with one or more halo substituents, in particular hydrogen, methyl, trifluoromethyl or methoxy;
R⁷ᶜ is hydrogen or $C_{1-4}$alkyl; in particular hydrogen or methyl;
Xᵃ is CH or N;
Xᵇ is O;
A¹ is CR⁹; wherein R⁹ is hydrogen, halo, or $C_{1-4}$alkyloxy; in particular wherein R⁹ is hydrogen, fluoro or methoxy;
A² is CH or N;
A³ and A⁴ are CH;
L¹ is carbonyl, NR¹⁰, NH—(C=O) or (C=O)—NH; wherein R¹⁰ is hydrogen or $C_{1-4}$alkyl; in particular wherein R¹⁰ is hydrogen or methyl;
R¹ and -L²-R² are taken together to form a bivalent radical —R¹—R²-L²-, wherein
—R¹—R²-L²- is selected from the group consisting of
  —CH=CH—CH=C(aryl¹)—,
  —CH=CH—N=C(aryl¹)—, —CH=CH—C($C_{1-4}$alkyl)=C(aryl¹)—, —(CH$_2$)$_2$—CH$_2$—CH(aryl¹)—,
  —(CH$_2$)$_2$—CH($C_{1-4}$alkyl)-CH(aryl¹)—, —(CH$_2$)$_2$—Y—CH(aryl¹)—, —CH=CH—C(aryl¹)=CH—, —CH=CH—CH=C(1-piperidinyl)-, and —(CH$_2$)$_2$—CH(aryl$^1$)—CH$_2$—;

wherein 1-piperidinyl may be substituted with one or more trifluoromethyl groups;

Y represents NR$^{14}$ or O; wherein R$^{14}$ is hydrogen, C$_{1-4}$alkylcarbonyl, or C$_{1-4}$alkyl; in particular R$^{14}$ represents hydrogen, methylcarbonyl, or methyl;

aryl$^1$ represents phenyl optionally substituted with one or more substituents each independently selected from the group consisting of halo, C$_{1-4}$alkyloxy, NR$^{11e}$R$^{12e}$, and C$_{1-4}$alkyl optionally substituted with one or more halo substituents; in particular aryl$^1$ represents phenyl optionally substituted with one, two or three substituents each independently selected from the group consisting of fluoro, chloro, methoxy, N(CH$_3$)$_2$, and methyl optionally substituted with one or more fluoro substituents;

R$^{11e}$ is hydrogen or C$_{1-4}$alkyl; in particular hydrogen, isopropyl or methyl;

each R$^{12e}$ independently is hydrogen or C$_{1-4}$alkyl; in particular hydrogen or methyl; and the pharmaceutically acceptable addition salts, and the solvates thereof provided that the compound is not 5-(4-methoxyphenyl)-N-[4-(5-oxazolyl)phenyl]-[1,2,4]triazolo[1,5-c]pyridin-2-amine In an embodiment, the present invention relates to those compounds of Formula (I) and stereoisomeric forms thereof wherein Het$^1$ is a heterocycle, having formula (a-1), (a-2), or (a-3);
R$^3$ is C$_{1-4}$alkyl; in particular methyl;
R$^4$ is hydrogen;
R$^5$ is hydrogen or C$_{1-4}$alkyl; in particular hydrogen or methyl;
R$^6$ is hydrogen or C$_{1-4}$alkyl; in particular hydrogen or methyl;
R$^{7a}$ is hydrogen or C$_{1-4}$alkyl; in particular hydrogen or methyl;
R$^{7b}$ is hydrogen, C$_{1-4}$alkyloxy, or C$_{1-4}$alkyl optionally substituted with one or more halo substituents, in particular hydrogen, methyl, trifluoromethyl or methoxy;
R$^{7c}$ is hydrogen or C$_{1-4}$alkyl; in particular hydrogen or methyl;
X$^a$ is CH or N;
X$^b$ is O;
A$^1$ is CR$^9$; wherein R$^9$ is hydrogen, halo, or C$_{1-4}$alkyloxy; in particular wherein R$^9$ is hydrogen, fluoro or methoxy;
A$^2$ is CH or N;
A$^3$ and A$^4$ are CH;
L$^1$ is carbonyl, NR$^{10}$, NH—(C=O) or (C=O)—NH; wherein R$^{10}$ is hydrogen or C$_{1-4}$alkyl; in particular wherein R$^{10}$ is hydrogen or methyl;

R$^1$ and -L$^2$-R$^2$ are taken together to form a bivalent radical —R$^1$—R$^2$-L$^2$-, wherein —R$^1$—R$^2$-L$^2$- is selected from the group consisting of
—CH=CH—CH=C(aryl$^1$)—,
—CH=CH—N=C(aryl$^1$)—, —CH=CH—C(C$_{1-4}$alkyl)=C(aryl$^1$)—, —(CH$_2$)$_2$—CH$_2$—CH(aryl$^1$)—,
—(CH$_2$)$_2$—CH(C$_{1-4}$alkyl)-CH(aryl$^1$)—, —(CH$_2$)$_2$—NR$^{14}$—CH(aryl$^1$)—,
—(CH$_2$)$_2$—O—CH(aryl$^1$)—, —CH=CH—C(aryl$^1$)=CH—, —CH=CH—CH=C(1-piperidinyl)-,
and —(CH$_2$)$_2$—CH(aryl$^1$)—CH$_2$—;

wherein 1-piperidinyl may be substituted with one or more trifluoromethyl groups;

wherein R$^{14}$ is hydrogen, C$_{1-4}$alkylcarbonyl, or C$_{1-4}$alkyl; in particular R$^{14}$ represents hydrogen, methylcarbonyl, or methyl;

aryl$^1$ represents phenyl optionally substituted with one or more substituents each independently selected from the group consisting of halo, C$_{1-4}$alkyloxy, NR$^{11e}$R$^{12e}$, and C$_{1-4}$alkyl optionally substituted with one or more halo substituents; in particular aryl$^1$ represents phenyl optionally substituted with one, two or three substituents each independently selected from the group consisting of fluoro, chloro, methoxy, N(CH$_3$)$_2$, and methyl optionally substituted with one or more fluoro substituents;

R$^{11e}$ is hydrogen or C$_{1-4}$alkyl; in particular hydrogen, isopropyl or methyl; each R$^{12e}$ independently is hydrogen or C$_{1-4}$alkyl; in particular hydrogen or methyl; and the pharmaceutically acceptable addition salts, and the solvates thereof provided that the compound is not 5-(4-methoxyphenyl)-N-[4-(5-oxazolyl)phenyl]-[1,2,4]triazolo[1,5-c]pyridin-2-amine In an embodiment, the present invention relates to those compounds of Formula (I) and stereoisomeric forms thereof wherein Het$^1$ is a heterocycle, having formula (a-1), (a-2), or (a-3a)
R$^3$ is C$_{1-4}$alkyl;
R$^4$, R$^5$, and R$^6$ each independently are hydrogen or C$_{1-4}$alkyl;
R$^{7a}$ is hydrogen, or C$_{1-4}$alkyl;
R$^{7b}$ and R$^{7c}$ each independently are hydrogen or C$_{1-4}$alkyl;
X$^a$ is CH or N;
X$^b$ is O;
A$^1$ is CR$^9$; wherein R$^9$ is hydrogen, halo, or C$_{1-4}$alkyloxy;
A$^2$, A$^3$ and A$^4$ each independently are CH or N;
provided that maximum two of A$^1$, A$^2$, A$^3$ and A$^4$ are N;
L$^1$ is NR$^{10}$, carbonyl or (C=O)—NH; wherein R$^{10}$ is hydrogen or C$_{1-4}$alkyl;

R$^1$ and -L$^2$-R$^2$ are taken together to form a bivalent radical —R$^1$—R$^2$-L$^2$- having formula (b-1), (b-2), (b-3), or (b-4)

—(CH$_2$)$_{m-n}$—Y—(CH$_2$)$_n$—     (b-1);

—(CH$_2$)$_n$—Y—(CH$_2$)$_{m-n}$—     (b-2);

—CH=CH—CH=CH—     (b-3);

—CH=CH—N=CH—     (b-4);

wherein (b-1) or (b-2) may be substituted on one carbon atom with one aryl$^1$ substituent;

wherein (b-3) or (b-4) may be substituted where possible with one aryl$^1$ substituent;

Y represents a direct bond, O or NR$^{14}$; wherein R$^{14}$ is hydrogen, C$_{1-4}$alkylcarbonyl, or C$_{1-4}$alkyl;

m represents 3 or 4;

n represents 1;

aryl$^1$ represents phenyl optionally substituted with one or more substituents each independently selected from the group consisting of halo, C$_{1-4}$alkyloxy, and C$_{1-4}$alkyl optionally substituted with one or more halo substituents;

and the pharmaceutically acceptable addition salts, and the solvates thereof provided that the compound is not 5-(4-methoxyphenyl)-N-[4-(5-oxazolyl)phenyl]-[1,2,4]triazolo[1,5-a]pyridin-2-amine In an embodiment, the present invention relates to those compounds of Formula (I) and stereoisomeric forms thereof wherein Het$^1$ is a heterocycle, having formula (a-1), (a-2), (a-3), or (a-4);
R$^3$ is C$_{1-4}$alkyl;
R$^4$, R$^5$, R$^6$, and R$^8$ each independently are hydrogen or C$_{1-4}$alkyl optionally substituted with one or more halo substituents;
R$^{7a}$ is hydrogen, halo, or C$_{1-4}$alkyl;
R$^{7b}$ and R$^{7c}$ each independently are hydrogen, halo, cyano, C$_{1-4}$alkyloxy, cycloC$_{3-7}$alkyl, or C$_{1-4}$alkyl optionally substituted with one or more halo substituents;

$X^a$ is CH or N;
$X^b$ is O or S;
$A^1$ is $CR^9$ or N; wherein $R^9$ is hydrogen, halo, or $C_{1-4}$alkyloxy;
$A^2$, $A^3$ and $A^4$ each independently are CH or N;
provided that maximum two of $A^1$, $A^2$, $A^3$ and $A^4$ are N;
$L^1$ is O, carbonyl, $NR^{10}$, NH—(C=O), or (C=O)—NH; wherein $R^{10}$ is hydrogen or $C_{1-4}$alkyl;
$R^1$ and -$L^2$-$R^2$ are taken together to form a bivalent radical —$R^1$—$R^2$-$L^2$- having formula (b-1), (b-2), (b-3), (b-4), or (b-5), —(CH$_2$)$_{m-n}$—Y—(CH$_2$)$_n$— (b-1);

—(CH$_2$)$_n$—Y—(CH$_2$)$_{m-n}$— (b-2);

—CH=CH—CH=CH— (b-3);

—CH=CH—N=CH— (b-4);

—CH=N—CH=CH— (b-5);

wherein (b-1) or (b-2) may contain one unsaturated bond;
wherein (b-1), (b-2) or the radical containing one unsaturated bond, may be substituted on one or more carbon atoms with one or where possible two substituents each independently selected from the group consisting of aryl$^1$, (C=O)-aryl$^1$, O-aryl$^1$, $NR^{13d}$-aryl$^1$, $C_{1-4}$alkylcarbonyl, halo, hydroxy, and $C_{1-4}$alkyl optionally substituted with one or more halo substituents;
wherein (b-3), (b-4), or (b-5) may be substituted where possible with one or more substituents each independently selected from the group consisting of aryl$^1$, 1-piperidinyl, 1-pyrrolidinyl, 4-morpholinyl, (C=O)-aryl$^1$, O-aryl$^1$, $NR^{13f}$-aryl$^1$, $C_{1-4}$alkylcarbonyl, and $C_{1-4}$alkyl optionally substituted with one or more halo substituents;
wherein said 1-piperidinyl, 1-pyrrolidinyl, or 4-morpholinyl may be substituted with one or more trifluoromethyl groups; and
wherein Y represents $NR^{14}$ or O; wherein $R^{14}$ is hydrogen, aryl$^1$, (C=O)-aryl$^1$, $C_{1-4}$alkylcarbonyl, or $C_{1-4}$alkyl optionally substituted with one or more halo substituents;
m represents 3 or 4; in particular m represents 3;
n represents 1;
wherein each aryl$^1$ independently represents phenyl optionally substituted with one or more substituents each independently selected from the group consisting of halo, $C_{1-4}$alkyloxy, cyano, $NR^{11e}R^{12e}$, morpholinyl, and $C_{1-4}$alkyl optionally substituted with one or more halo substituents;
or a 5- or 6-membered heteroaryl selected from the group consisting of furanyl, thiophenyl, pyrazolyl, oxazolyl, isoxazolyl, thiazolyl, isothiazolyl, thiadiazolyl, oxadiazolyl, pyridinyl, pyrimidinyl, pyridazinyl, and pyrazinyl, wherein said 5- or 6-membered heteroaryl may be substituted with one or more substituents each independently selected from the group consisting of halo, $C_{1-4}$alkyloxy, cyano, $NR^{11f}R^{12f}$, morpholinyl, and $C_{1-4}$alkyl optionally substituted with one or more halo substituents;
each $R^{11d}$, $R^{11e}$ and $R^{11f}$ independently is hydrogen, $C_{1-4}$alkyl or $C_{1-4}$alkylcarbonyl;
each $R^{12d}$, $R^{12e}$ and $R^{12f}$ independently is hydrogen or $C_{1-4}$alkyl;
each $R^{13d}$ and $R^{13f}$ independently is hydrogen, or $C_{1-4}$alkyl optionally substituted with one or more substituents each independently selected from the group consisting of halo and cyclo$C_{3-7}$alkyl;

and the pharmaceutically acceptable addition salts, and the solvates thereof; provided that the compound is not 5-(4-methoxyphenyl)-N-[4-(5-oxazolyl)phenyl]-[1,2,4]triazolo[1,5-c]pyridin-2-amine, 5-(4-methoxyphenyl)-N-[4-(3-pyridinyl)phenyl]-[1,2,4]triazolo[1,5-c]pyridin-2-amine, or 5-(4-methoxyphenyl)-N-[6-(1H-pyrazol-4-yl)-3-pyridinyl]-[1,2,4]triazolo[1,5-a]-pyridin-2-amine.

An embodiment of the present invention relates to those compounds of Formula (I) and stereoisomeric forms thereof, or any subgroup thereof as mentioned in any of the other embodiments, wherein one or more of the following restrictions apply:
(a) Het$^1$ is a heterocycle, having formula (a-1), (a-2), or (a-3); in particular Het$^1$ is a heterocycle, having formula (a-1), (a-2), or (a-3a);
(b) $R^3$ is $C_{1-4}$alkyl;
(c) $R^4$, $R^5$ and $R^6$ each independently are hydrogen or $C_{1-4}$alkyl;
(d) $R^{7a}$ is hydrogen or $C_{1-4}$alkyl;
(e) $R^{7b}$ and $R^{7c}$ each independently are hydrogen, or $C_{1-4}$alkyl;
(f) $X^b$ is O;
(g) $A^1$ is $CR^9$; wherein $R^9$ is hydrogen, halo, or $C_{1-4}$alkyloxy;
(h) $A^2$ is CH or N; and $A^3$ and $A^4$ are CH;
(i) $L^1$ is $NR^{10}$, carbonyl or (C=O)—NH; wherein $R^{10}$ is hydrogen or $C_{1-4}$alkyl;
(j) $R^1$ and -$L^2$-$R^2$ are taken together to form a bivalent radical —$R^1$-$R^2$-$L^2$- having formula (b-1), (b-2), (b-3), or (b-4); in particular (b-1) or (b-2);
(k) (b-1) or (b-2) may be substituted on one carbon atom with one aryl$^1$ substituent;
(l) (b-3) or (b-4) may be substituted where possible with one aryl$^1$ substituent;
(m) Y represents a direct bond, O or $NR^{14}$;
(n) $R^{14}$ is hydrogen, $C_{1-4}$alkylcarbonyl, or $C_{1-4}$alkyl;
(o) aryl$^1$ represents phenyl optionally substituted with one or more substituents each independently selected from the group consisting of halo, $C_{1-4}$alkyloxy, and $C_{1-4}$alkyl optionally substituted with one or more halo substituents.

Another embodiment of the present invention relates to those compounds of Formula (I) and stereoisomeric forms thereof, or any subgroup thereof as mentioned in any of the other embodiments, wherein one or more of the following restrictions apply:
(a) Het$^1$ is a heterocycle, having formula (a-1), (a-2), or (a-3a);
(b) $R^3$ is methyl;
(c) $R^4$, $R^5$ and $R^6$ each independently are hydrogen or methyl;
(d) $R^{7a}$ is hydrogen or methyl;
(e) $R^{7b}$ and $R^{7c}$ each independently are hydrogen, or methyl;
(f) $X^b$ is O;
(g) $A^1$ is $CR^9$; wherein $R^9$ is hydrogen, fluoro, or methoxy;
(h) $A^2$ is CH or N; and $A^3$ and $A^4$ are CH;
(i) $L^1$ is $NR^{10}$, carbonyl or (C=O)—NH; wherein $R^{10}$ is hydrogen or methyl;
(j) $R^1$ and -$L^2$-$R^2$ are taken together to form a bivalent radical —$R^1$—$R^2$-$L^2$- having formula (b-1), (b-2), (b-3), or (b-4);
(k) (b-1) or (b-2) may be substituted on one carbon atom with one aryl$^1$ substituent;
(l) (b-3) or (b-4) may be substituted where possible with one aryl$^1$ substituent;
(m) Y represents a direct bond, O or $NR^{14}$;
(n) $R^{14}$ is hydrogen, methylcarbonyl, or methyl;
(o) aryl$^1$ represents phenyl optionally substituted with one or more substituents each independently selected from the group consisting of fluoro, methoxy, and methyl optionally substituted with one or more fluoro substituents.

An embodiment of the present invention relates to those compounds of Formula (I) and stereoisomeric forms thereof, or any subgroup thereof as mentioned in any of the other embodiments, wherein one or more of the following restrictions apply:
(i) $Het^1$ is a heterocycle, having formula (a-1) or (a-3a); in particular (a-1)
(ii) $R^3$ is $C_{1-4}$alkyl; in particular methyl;
(iii) $R^4$ is hydrogen;
(iv) $R^{7a}$ and $R^{7b}$ are hydrogen; $R^{7c}$ is $C_{1-4}$alkyl; in particular $R^{7c}$ is methyl;
(v) $X^a$ is N;
(vi) $A^1$ is $CR^9$ wherein $R^9$ is $C_{1-4}$alkyloxy; in particular $R^9$ is methoxy;
$A^2$, $A^3$ and $A^4$ are CH;
(vii) $L^1$ is NH.

Another embodiment of the present invention relates to those compounds of Formula (I) and stereoisomeric forms thereof, or any subgroup thereof as mentioned in any of the other embodiments, wherein $R^1$ and $-L^2-R^2$ taken together form a bivalent radical —$R^1$—$R^2$-$L^2$- having formula (b-1), (b-2), (b-3), (b-4) or (b-5); in particular (b-1), (b-2), (b-3) or (b-4); more in particular (b-1) or (b-2);
wherein (b-1) or (b-2) may contain one unsaturated bond;
wherein (b-1), (b-2) or the radical containing one unsaturated bond, may be substituted with substituents as listed in any of the other embodiments;
wherein (b-3), (b-4) or (b-5) may be substituted with substituents as listed in any of the other embodiments.

Another embodiment of the present invention relates to those compounds of Formula (I) and stereoisomeric forms thereof, or any subgroup thereof as mentioned in any of the other embodiments, wherein $R^1$ and $-L^2-R^2$ taken together form a bivalent radical —$R^1$—$R^2$-$L^2$- having formula (b-1), (b-2), (b-3), (b-4) or (b-5); in particular (b-1), (b-2), (b-3) or (b-4); more in particular (b-1) or (b-2);
wherein (b-1), (b-2), (b-3), (b-4) or (b-5) may be substituted with substituents as listed in any of the other embodiments.

Another embodiment of the present invention relates to those compounds of Formula (I) and stereoisomeric forms thereof, or any subgroup thereof as mentioned in any of the other embodiments, wherein $R^1$ and $-L^2-R^2$ taken together form a bivalent radical —$R^1$—$R^2$-$L^2$- having formula (b-3), (b-4) or (b-5); in particular (b-4) or (b-5);
wherein (b-3), (b-4) or (b-5) may be substituted with substituents as listed in any of the other embodiments.

Another embodiment of the present invention relates to those compounds of Formula (I) and stereoisomeric forms thereof, or any subgroup thereof as mentioned in any of the other embodiments, wherein $R^1$ and $-L^2-R^2$ taken together form a bivalent radical —$R^1$—$R^2$-$L^2$- having formula (b-1) or (b-2), wherein (b-1) and (b-2) may be substituted with substituents as listed in any of the other embodiments.

Another embodiment of the present invention relates to those compounds of Formula (I) and stereoisomeric forms thereof, or any subgroup thereof as mentioned in any of the other embodiments, wherein $R^1$ and $-L^2-R^2$ taken together form a bivalent radical —$R^1$—$R^2$-$L^2$- selected from the group consisting of —(CH$_2$)$_4$—,
—(CH$_2$)$_2$—NH—CH$_2$—, —(CH$_2$)$_2$—N(CH$_3$)—CH$_2$—, —(CH$_2$)$_2$—N(COCH$_3$)—CH$_2$—,
—(CH$_2$)$_2$—O—CH$_2$—, —CH=CH—CH=CH—, and —CH=CH—N=CH—; wherein each of these groups may be substituted with one aryl$^1$ substituent.

Another embodiment of the present invention relates to those compounds of Formula (I) and stereoisomeric forms thereof, or any subgroup thereof as mentioned in any of the other embodiments, wherein $R^1$ and $-L^2-R^2$ taken together form a bivalent radical —$R^1$—$R^2$-$L^2$- selected from the group consisting of —(CH$_2$)$_3$—CH(aryl$^1$)—, —(CH$_2$)$_2$—NH—CH(aryl$^1$)—, —(CH$_2$)$_2$—N(CH$_3$)—CH(aryl$^1$)—, —(CH$_2$)$_2$—N(COCH$_3$)—CH(aryl$^1$)—, —(CH$_2$)$_2$—O—CH(aryl$^1$)—, —CH=CH—CH=C(aryl$^1$)—, and —CH=CH—N=C(aryl$^1$)—.

Another embodiment of the present invention relates to those compounds of Formula (I) and stereoisomeric forms thereof, or any subgroup thereof as mentioned in any of the other embodiments, wherein $R^1$ and $-L^2-R^2$ taken together form a bivalent radical —$R^1$—$R^2$-$L^2$-, wherein —$R^1$—$R^2$-$L^2$- is selected from the group consisting of —CH=CH—CH=C(aryl$^1$)—, —CH=CH—N=C(aryl$^1$)—, —CH=CH—C(C$_{1-4}$alkyl)=C(aryl$^1$)—, —(CH$_2$)$_2$—CH$_2$—CH(aryl$^1$)—, —(CH$_2$)$_2$—CH(C$_{1-4}$alkyl)-CH(aryl$^1$)—, —(CH$_2$)$_2$—Y—CH(aryl$^1$)-, —CH=CH—C(aryl$^1$)=CH—, —CH=CH—CH=C(1-piperidinyl)-, and —(CH$_2$)$_2$—CH(aryl$^1$)—CH$_2$—;
wherein 1-piperidinyl may be substituted with one or more trifluoromethyl groups.

Another embodiment of the present invention relates to those compounds of Formula (I) and stereoisomeric forms thereof, or any subgroup thereof as mentioned in any of the other embodiments, wherein $R^1$ and $-L^2-R^2$ taken together form a bivalent radical —$R^1$—$R^2$-$L^2$-, wherein —$R^1$—$R^2$-$L^2$- is selected from the group consisting of —CH=CH—CH=C(aryl$^1$)—, —CH=CH—N=C(aryl$^1$)—, —CH=CH—C(C$_{1-4}$alkyl)=C(aryl$^1$)—, —(CH$_2$)$_2$—CH$_2$—CH(aryl$^1$)—, —(CH$_2$)$_2$—CH(C$_{1-4}$alkyl)-CH(aryl$^1$)—, —(CH$_2$)$_2$—Y—CH(aryl$^1$)-, —CH=CH—C(aryl$^1$)=CH—, —CH=CH—CH=C(1-piperidinyl)-, and —(CH$_2$)$_2$—CH(aryl$^1$)—CH$_2$—;
wherein 1-piperidinyl may be substituted with one or more trifluoromethyl groups;
wherein Y represents $NR^{14}$ or O.

Another embodiment of the present invention relates to those compounds of Formula (I) and stereoisomeric forms thereof, or any subgroup thereof as mentioned in any of the other embodiments, wherein $R^1$ and $-L^2-R^2$ taken together form a bivalent radical —$R^1$—$R^2$-$L^2$-, wherein —$R^1$—$R^2$-$L^2$- is selected from the group consisting of —CH=CH—CH=C(aryl$^1$)—, —CH=CH—N=C(aryl$^1$)—, —CH=CH—C(C$_{1-4}$alkyl)=C(aryl$^1$)—, —(CH$_2$)$_2$—CH$_2$—CH(aryl$^1$)—, —(CH$_2$)$_2$—CH(C$_{1-4}$alkyl)-CH(aryl$^1$)—, —(CH$_2$)$_2$—NR$^{14}$—CH(aryl$^1$)—, —(CH$_2$)$_2$—O—CH(aryl$^1$)—, —CH=CH—C(aryl$^1$)=CH—, —CH=CH—CH=C(1-piperidinyl)-, and —(CH$_2$)$_2$—CH(aryl$^1$)—CH$_2$—;
wherein 1-piperidinyl may be substituted with one or more trifluoromethyl groups;
wherein $R^{14}$ represents hydrogen, $C_{1-4}$alkylcarbonyl or $C_{1-4}$alkyl.

Another embodiment of the present invention relates to those compounds of Formula (I) and stereoisomeric forms thereof, or any subgroup thereof as mentioned in any of the other embodiments, wherein $R^1$ and $-L^2-R^2$ taken together form a bivalent radical —$R^1$—$R^2$-$L^2$-, wherein —$R^1$—$R^2$-$L^2$- is selected from the group consisting of —CH=CH—CH=C(aryl$^1$)—, —CH=CH—N=C(aryl$^1$)—, —CH=CH—C(C$_{1-4}$alkyl)=C(aryl$^1$)—, —(CH$_2$)$_2$—CH$_2$—CH(aryl$^1$)—, —(CH$_2$)$_2$—CH(C$_{1-4}$alkyl)-CH(aryl$^1$)—, —(CH$_2$)$_2$—NR$^{14}$—CH(aryl$^1$)—, —(CH$_2$)$_2$—O—CH(aryl$^1$)—, —CH=CH—C(aryl$^1$)=CH—, —CH=CH—CH=C(1-piperidinyl)-, —(CH$_2$)$_2$—CH(aryl$^1$)—CH$_2$—, and —CH(aryl$^1$)—(CH$_2$)$_3$—;

wherein 1-piperidinyl may be substituted with one or more trifluoromethyl groups;
wherein $R^{14}$ represents hydrogen, $C_{1-4}$alkylcarbonyl or $C_{1-4}$alkyl.

Another embodiment of the present invention relates to those compounds of Formula (I) and stereoisomeric forms thereof, or any subgroup thereof as mentioned in any of the other embodiments, wherein $R^1$ and -$L^2$-$R^2$ taken together form a bivalent radical —$R^1$—$R^2$-$L^2$-, wherein —$R^1$—$R^2$-$L^2$- is selected from the group consisting of —CH=CH—CH=C(aryl$^1$)—, —CH=CH—N=C(aryl$^1$)—, —CH=CH—C(C$_{1-4}$alkyl)=C(aryl$^1$)—, —(CH$_2$)$_2$—CH(C$_{1-4}$alkyl)-CH(aryl$^1$)-, —(CH$_2$)$_2$—NR$^{14}$—CH(aryl$^1$)—, —(CH$_2$)$_2$—O—CH(aryl$^1$)—, —CH=CH—C(aryl$^1$)=CH—, —CH=CH—CH=C(1-piperidinyl)-, and —(CH$_2$)$_2$—CH(aryl$^1$)—CH$_2$—,
wherein 1-piperidinyl may be substituted with one or more trifluoromethyl groups;
wherein $R^{14}$ represents hydrogen, $C_{1-4}$alkylcarbonyl or $C_{1-4}$alkyl.

Another embodiment of the present invention relates to those compounds of Formula (I) and stereoisomeric forms thereof, or any subgroup thereof as mentioned in any of the other embodiments, wherein $R^1$ and -$L^2$-$R^2$ taken together form a bivalent radical —$R^1$—$R^2$-$L^2$-, wherein —$R^1$—$R^2$-$L^2$- is selected from the group consisting of —CH=CH—CH=C(aryl$^1$)—, —CH=CH—N=C(aryl$^1$)—, —CH=CH—C(C$_{1-4}$alkyl)=C(aryl$^1$)—, —(CH$_2$)$_2$—NR$^{14}$—CH(aryl$^1$)—, —(CH$_2$)$_2$—O—CH(aryl$^1$)—, —CH=CH—C(aryl$^1$)=CH—, —CH=CH—CH=C(1-piperidinyl)-, and —(CH$_2$)$_2$—CH(aryl$^1$)—CH$_2$—,
wherein 1-piperidinyl may be substituted with one or more trifluoromethyl groups;
wherein $R^{14}$ represents hydrogen, $C_{1-4}$alkylcarbonyl or $C_{1-4}$alkyl.

Another embodiment of the present invention relates to those compounds of Formula (I) and stereoisomeric forms thereof, or any subgroup thereof as mentioned in any of the other embodiments, wherein $R^1$ and -$L^2$-$R^2$ taken together form a bivalent radical —$R^1$—$R^2$-$L^2$-, wherein —$R^1$—$R^2$-$L^2$- is selected from the group consisting of —CH=CH—CH=C(aryl$^1$)—, —CH=CH—N=C(aryl$^1$)—, —CH=CH—C(C$_{1-4}$alkyl)=C(aryl$^1$)—, —(CH$_2$)$_2$—NR$^{14}$—CH(aryl$^1$)—, —(CH$_2$)$_2$—O—CH(aryl$^1$)—, —CH=CH—C(aryl$^1$)=CH—, and —CH=CH—CH=C(1-piperidinyl)-, wherein 1-piperidinyl may be substituted with one or more trifluoromethyl groups;
wherein $R^{14}$ represents hydrogen, $C_{1-4}$alkylcarbonyl or $C_{1-4}$alkyl.

Another embodiment of the present invention relates to those compounds of Formula (I) and stereoisomeric forms thereof, or any subgroup thereof as mentioned in any of the other embodiments, wherein $R^1$ and -$L^2$-$R^2$ taken together form a bivalent radical —$R^1$—$R^2$-$L^2$-, wherein —$R^1$—$R^2$-$L^2$- is —(CH$_2$)$_2$—NR$^{14}$—CH(aryl$^1$)— or —(CH$_2$)$_2$—O—CH(aryl$^1$)—.

Another embodiment of the present invention relates to those compounds of Formula (I) and stereoisomeric forms thereof, or any subgroup thereof as mentioned in any of the other embodiments, wherein $R^1$ and -$L^2$-$R^2$ taken together form a bivalent radical —$R^1$—$R^2$-$L^2$-, wherein —$R^1$—$R^2$-$L^2$- is —(CH$_2$)$_2$—CH(C$_{1-4}$alkyl)-CH(aryl$^1$)— or —(CH$_2$)$_2$—CH(aryl$^1$)—CH$_2$—, in particular —(CH$_2$)$_2$—CH(aryl$^1$)—CH$_2$—.

An embodiment of the present invention relates to those compounds of Formula (I) and stereoisomeric forms thereof, or any subgroup thereof as mentioned in any of the other embodiments, wherein (b-3) is restricted to —CH=CH—CH=C(aryl$^1$)—, wherein (b-4) is restricted to —CH=CH—N=C(aryl$^1$)—, and wherein (b-5) is restricted to —CH=N—CH=C(aryl$^1$)—.

Another embodiment of the present invention relates to those compounds of Formula (I) and stereoisomeric forms thereof, or any subgroup thereof as mentioned in any of the other embodiments, wherein $R^1$ and -$L^2$-$R^2$ taken together form a bivalent radical —$R^1$—$R^2$-$L^2$-, wherein —$R^1$—$R^2$-$L^2$- is selected from the group consisting of —(CH$_2$)$_2$—CH(C$_{1-4}$alkyl)-CH(aryl$^1$)—, —(CH$_2$)$_2$—NR$^{14}$—CH(aryl$^1$)—, —(CH$_2$)$_2$—O—CH(aryl$^1$)—, —(CH$_2$)$_2$—CH(aryl$^1$)—CH$_2$—, (b-3), (b-4), and (b-5), wherein (b-3), (b-4) or (b-5) may be further substituted according to any of the other embodiments;

in particular —$R^1$—$R^2$-$L^2$- is selected from the group consisting of —(CH$_2$)$_2$—NR$^{14}$—CH(aryl$^1$)—, —(CH$_2$)$_2$—O—CH(aryl$^1$)—, —(CH$_2$)$_2$—CH(aryl$^1$)—CH$_2$—, (b-3), (b-4), and (b-5), wherein (b-3), (b-4) or (b-5) may be further substituted according to any of the other embodiments;

even more in particular —$R^1$—$R^2$-$L^2$- is selected from the group consisting of —(CH$_2$)$_2$—NR$^{14}$—CH(aryl$^1$)—, —(CH$_2$)$_2$—O—CH(aryl$^1$)—, (b-3), (b-4), and (b-5), wherein (b-3), (b-4) or (b-5) may be further substituted according to any of the other embodiments.

Another embodiment of the present invention relates to those compounds of Formula (I) and stereoisomeric forms thereof, or any subgroup thereof as mentioned in any of the other embodiments, wherein $R^1$ and -$L^2$-$R^2$ are taken together to form a bivalent radical —$R^1$—$R^2$-$L^2$- having formula (b-1), (b-2), (b-3), (b-4), (b-5), (b-6), (b-7) or —(CH$_2$)$_2$—CH(aryl$^1$)—CH$_2$—; in particular (b-1), (b-2), (b-3), (b-4), (b-5), or —(CH$_2$)$_2$—CH(aryl$^1$)—CH$_2$— wherein (b-1) or (b-2) may contain one unsaturated bond;
wherein (b-1), (b-2) or the radical containing one unsaturated bond, may be substituted on one or more carbon atoms with one or where possible two substituents each independently selected from the group consisting of aryl$^1$, (C=O)-aryl$^1$, O-aryl$^1$, NR$^{13d}$-aryl$^1$, $C_{1-4}$alkylcarbonyl, halo, hydroxy, and $C_{1-4}$alkyl optionally substituted with one or more halo substituents;
wherein (b-3), (b-4), or (b-5) may be substituted where possible with one or more substituents each independently selected from the group consisting of aryl$^1$, 1-piperidinyl, 1-pyrrolidinyl, 4-morpholinyl, (C=O)-aryl$^1$, O-aryl$^1$, NR$^{13f}$-aryl$^1$, $C_{1-4}$alkylcarbonyl, and $C_{1-4}$alkyl optionally substituted with one or more halo substituents;
wherein said 1-piperidinyl, 1-pyrrolidinyl, or 4-morpholinyl may be substituted with one or more trifluoromethyl groups;
wherein (b-6) or (b-7) may be substituted on one or more CH$_2$ groups with one or where possible two substituents each independently selected from the group consisting of aryl$^1$, (C=O)-aryl$^1$, O-aryl$^1$, NR$^{13e}$-aryl$^1$, $C_{1-4}$alkylcarbonyl, halo, hydroxy, and $C_{1-4}$alkyl optionally substituted with one or more halo substituents; and wherein (b-6) or (b-7) may be substituted on the 1,2-benzenediyl-moiety with one or more substituents each independently selected from the group consisting of halo, $C_{1-4}$alkyloxy, cyano, NR$^{11d}$R$^{12d}$, morpholinyl, and $C_{1-4}$alkyl optionally substituted with one or more halo substituents;
Y represents NR$^{14}$ or O; wherein $R^{14}$ is hydrogen, aryl$^1$, (C=O)-aryl$^1$, $C_{1-4}$alkylcarbonyl, or $C_{1-4}$alkyl optionally substituted with one or more halo substituents.

Another embodiment of the present invention relates to those compounds of Formula (I) and stereoisomeric forms thereof, or any subgroup thereof as mentioned in any of the other embodiments, wherein $R^1$ and $-L^2-R^2$ taken together form a bivalent radical $—R^1—R^2-L^2-$, wherein $—R^1—R^2-L^2-$ is selected from the group consisting of $—CH=CH—CH=C(aryl^1)—$, $—CH=CH—N=C(aryl^1)—$, $—CH=CH—C(C_{1-4}alkyl)=C(aryl^1)—$, $—(CH_2)_2—CH_2—CH(aryl^1)—$, $—(CH_2)_2—CH(C_{1-4}alkyl)-CH(aryl^1)—$, $—(CH_2)_2—Y—CH(aryl^1)—$, $—CH=CH—C(aryl^1)=CH—$, and $—(CH_2)_2—CH(aryl^1)—CH_2—$; more in particular $—R^1—R^2-L^2-$ is $—(CH_2)_2—CH_2—CH(aryl^1)—$.

Another embodiment of the present invention relates to those compounds of Formula (I) and stereoisomeric forms thereof, or any subgroup thereof as mentioned in any of the other embodiments, wherein $R^1$ and $-L^2-R^2$ taken together form a bivalent radical $—R^1—R^2-L^2-$, wherein $—R^1—R^2-L^2-$ is selected from the group consisting of $—CH=CH—CH=C(aryl^1)—$, $—CH=CH—N=C(aryl^1)—$, $—CH=CH—C(C_{1-4}alkyl)=C(aryl^1)—$, $—(CH_2)_2—CH_2—CH(aryl^1)—$, $—(CH_2)_2—CH(C_{1-4}alkyl)-CH(aryl^1)—$, $—(CH_2)_2—Y—CH(aryl^1)—$, $—CH=CH—C(aryl^1)=CH—$, and $—(CH_2)_2—CH(aryl^1)—CH_2—$; more in particular $—R^1—R^2-L^2-$ is $—(CH_2)_2—CH_2—CH(aryl^1)—$;
wherein Y represents $NR^{14}$ or O.

Another embodiment of the present invention relates to those compounds of Formula (I) and stereoisomeric forms thereof, or any subgroup thereof as mentioned in any of the other embodiments, wherein $R^1$ and $-L^2-R^2$ taken together form a bivalent radical $—R^1—R^2-L^2-$, wherein $—R^1—R^2-L^2-$ is selected from the group consisting of $—CH=CH—CH=C(aryl^1)—$, $—CH=CH—N=C(aryl^1)—$, $—CH=CH—C(C_{1-4}alkyl)=C(aryl^1)—$, $—(CH_2)_2—CH_2—CH(aryl^1)—$, $—(CH_2)_2—CH(C_{1-4}alkyl)-CH(aryl^1)—$, $—(CH_2)_2—NR^{14}—CH(aryl^1)—$, $—(CH_2)_2—O—CH(aryl^1)—$, $—CH=CH—C(aryl^1)=CH—$, and $—(CH_2)_2—CH(aryl^1)—CH_2—$; wherein $R^{14}$ represents hydrogen, $C_{1-4}$alkylcarbonyl or $C_{1-4}$alkyl.

Another embodiment of the present invention relates to those compounds of Formula (I) and stereoisomeric forms thereof, or any subgroup thereof as mentioned in any of the other embodiments, wherein $R^1$ and $-L^2-R^2$ taken together form a bivalent radical $—R^1—R^2-L^2-$, wherein $—R^1—R^2-L^2-$ is selected from the group consisting of $—CH=CH—CH=C(aryl^1)—$, $—CH=CH—N=C(aryl^1)—$, $—CH=CH—C(C_{1-4}alkyl)=C(aryl^1)—$, $—CH=CH—C(aryl^1)=CH—$, and $—CH=CH—CH=C(1$-piperidinyl$)-$, wherein 1-piperidinyl may be substituted with one or more trifluoromethyl groups.

Another embodiment of the present invention relates to those compounds of Formula (I) and stereoisomeric forms thereof, or any subgroup thereof as mentioned in any of the other embodiments, wherein (b-1) or (b-2) only contain saturated bonds, and wherein (b-1) or (b-2) may be substituted on one or more carbon atoms with one or where possible two substituents each independently selected from the group consisting of $aryl^1$, $(C=O)$-$aryl^1$, O-$aryl^1$, $NR^{13d}$-$aryl^1$, $C_{1-4}$alkylcarbonyl, halo, hydroxy, and $C_{1-4}$alkyl optionally substituted with one or more halo substituents.

Another embodiment of the present invention relates to those compounds of Formula (I) and stereoisomeric forms thereof, or any subgroup thereof as mentioned in any of the other embodiments, wherein $R^1$ and $-L^2-R^2$ taken together form a bivalent radical $—R^1—R^2-L^2-$ having formula (b-1), (b-3), or (b-4); more in particular $R^1$ and $-L^2-R^2$ taken together form a bivalent radical $—R^1—R^2-L^2-$ having formula (b-3), (b-4), or (b-1) wherein (b-1) is $—(CH_2)_4—$, $—(CH_2)_2—NH—CH_2—$, $—(CH_2)_2—N(CH_3)—CH_2—$, $—(CH_2)_2—N(COCH_3)—CH_2—$ or $—(CH_2)_2—O—CH_2—$, wherein said bivalent radicals may be substituted with substituents as listed in any of the other embodiments.

Another embodiment of the present invention relates to those compounds of Formula (I) and stereoisomeric forms thereof, or any subgroup thereof as mentioned in any of the other embodiments, wherein $R^1$ and $-L^2-R^2$ taken together form a bivalent radical $—R^1—R^2-L^2-$ having formula (b-1) or (b-2); in particular (b-1); more in particular $—(CH_2)_4—$, $—(CH_2)_2—NH—CH_2—$, $—(CH_2)_2—N(CH_3)—CH_2—$, $—(CH_2)_2—N(COCH_3)—CH_2—$ or $—(CH_2)_2—O—CH_2—$; even more in particular $—(CH_2)_4—$;
wherein said bivalent radicals may be substituted with substituents as listed in any of the other embodiments.

Another embodiment of the present invention relates to those compounds of Formula (I) and stereoisomeric forms thereof, or any subgroup thereof as mentioned in any of the other embodiments, wherein (b-3), (b-4), or (b-5) may be substituted where possible with one or more substituents each independently selected from the group consisting of $aryl^1$, $(C=O)$-$aryl^1$, O-$aryl^1$, $NR^{13f}$-$aryl^1$, $C_{1-4}$alkylcarbonyl, and $C_{1-4}$alkyl optionally substituted with one or more halo substituents;
and wherein the other bivalent radicals $—R^1—R^2-L^2-$ may be substituted with substituents as listed in any of the other embodiments.

Another embodiment of the present invention relates to those compounds of Formula (I) and stereoisomeric forms thereof, or any subgroup thereof as mentioned in any of the other embodiments, wherein $R^1$ and $-L^2-R^2$ taken together form a bivalent radical $—R^1—R^2-L^2-$ having formula (b-1) or (b-2) wherein (b-1) or (b-2) may be substituted with substituents as listed in any of the other embodiments;
and wherein $Het^1$ is a heterocycle having formula (a-3); in particular $Het^1$ is a heterocycle having formula (a-3a).

An embodiment of the present invention relates to those compounds of Formula (I) and stereoisomeric forms thereof, or any subgroup thereof as mentioned in any of the other embodiments, wherein $Het^1$ is a heterocycle, having formula (a-1) or (a-3); in particular (a-1) or (a-3a).

An embodiment of the present invention relates to those compounds of Formula (I) and stereoisomeric forms thereof, or any subgroup thereof as mentioned in any of the other embodiments, wherein $Het^1$ is a heterocycle, having formula (a-3), in particular (a-3a).

An embodiment of the present invention relates to those compounds of Formula (I) and stereoisomeric forms thereof, or any subgroup thereof as mentioned in any of the other embodiments, wherein $Het^1$ is a heterocycle, having formula (a-2) or (a-3); in particular (a-2) or (a-3a).

An embodiment of the present invention relates to those compounds of Formula (I) and stereoisomeric forms thereof, or any subgroup thereof as mentioned in any of the other embodiments, wherein $Het^1$ is a heterocycle, having formula (a-1), (a-2) or (a-3).

An embodiment of the present invention relates to those compounds of Formula (I) and stereoisomeric forms thereof, or any subgroup thereof as mentioned in any of the other embodiments, wherein $Het^1$ is a heterocycle, having formula (a-1), (a-2) or (a-3).

Another embodiment of the present invention relates to those compounds of Formula (I) or any subgroup thereof as mentioned in any of the other embodiments wherein Y represents $NR^{14}$ or O.

Another embodiment of the present invention relates to those compounds of Formula (I) or any subgroup thereof as mentioned in any of the other embodiments wherein $R^{14}$ is hydrogen, $C_{1-4}$alkylcarbonyl, or $C_{1-4}$alkyl.

Another embodiment of the present invention relates to those compounds of Formula (I) or any subgroup thereof as mentioned in any of the other embodiments wherein $R^9$ is hydrogen or $C_{1-4}$alkyloxy; in particular $C_{1-4}$alkyloxy.

Another embodiment of the present invention relates to those compounds of Formula (I) or any subgroup thereof as mentioned in any of the other embodiments wherein Y represents a direct bond.

Another embodiment of the present invention relates to those compounds of formula (I) or any subgroup thereof as mentioned in any of the other embodiments, wherein at least one of $A^1$, $A^2$, $A^3$ and $A^4$ is other than CH.

Another embodiment of the present invention relates to those compounds of formula (I) or any subgroup thereof as mentioned in any of the other embodiments, wherein at least one of $A^1$, $A^2$, $A^3$ and $A^4$ is N; preferably wherein exactly one of $A^1$, $A^2$, $A^3$ and $A^4$ is N.

Another embodiment of the present invention relates to those compounds of formula (I) or any subgroup thereof as mentioned in any of the other embodiments, wherein $A^3$ and $A^4$ are CH.

Another embodiment of the present invention relates to those compounds of formula (I) or any subgroup thereof as mentioned in any of the other embodiments, wherein maximum one of $A^1$, $A^2$, $A^3$ and $A^4$ is N.

Another embodiment of the present invention relates to those compounds of Formula (I) or any subsgroup thereof as mentioned in any of the other embodiments wherein $R^4$, $R^5$, $R^6$, and $R^8$ each independently are hydrogen or $C_{1-4}$alkyl.

An embodiment of the present invention relates to those compounds of Formula (I) and stereoisomeric forms thereof, or any subgroup thereof as mentioned in any of the other embodiments, wherein each aryl$^1$ independently represents phenyl optionally substituted with one or more substituents each independently selected from the group consisting of halo, $C_{1-4}$alkyloxy, cyano, $NR^{11e}R^{12e}$, morpholinyl, and $C_{1-4}$alkyl optionally substituted with one or more halo substituents; in particular each aryl$^1$ independently represents phenyl substituted with trifluoromethyl or halo in the ortho position; more in particular each aryl$^1$ independently represents phenyl substituted with trifluoromethyl or chloro in the ortho position.

An embodiment of the present invention relates to those compounds of Formula (I) and stereoisomeric forms thereof, or any subgroup thereof as mentioned in any of the other embodiments, wherein $R^1$ and -$L^2$-$R^2$ are taken together to form a bivalent radical —$R^1$-$R^2$-$L^2$- having formula (b-1), (b-2), (b-3), (b-4), (b-5), (b-6), or (b-7); in particular (b-1), (b-2), (b-3), (b-4) or (b-5);
    wherein (b-1) or (b-2) may contain one unsaturated bond; in particular wherein (b-1) or (b-2) only contain saturated bonds;
    wherein (b-1), (b-2) or, where applicable, the radical containing one unsaturated bond, is substituted on one carbon atom with one aryl$^1$ substituent; and wherein optionally (b-1), (b-2) or, where applicable, the radical containing one unsaturated bond, is further substituted on one of the other carbon atoms with one $C_{1-4}$alkyl moiety;
    wherein (b-3), (b-4), or (b-5) is substituted with one substituent selected from the group consisting of aryl$^1$ and 1-piperidinyl; and wherein optionally (b-3), (b-4), or (b-5) is further substituted with one $C_{1-4}$alkyl moiety;
    wherein 1-piperidinyl may be substituted with one or more trifluoromethyl groups;
    in particular wherein (b-3), (b-4), or (b-5) is substituted with one aryl$^1$ substituent and wherein optionally (b-3), (b-4), or (b-5) is further substituted with one $C_{1-4}$alkyl moiety.

An embodiment of the present invention relates to those compounds of Formula (I) and stereoisomeric forms thereof, or any subgroup thereof as mentioned in any of the other embodiments, wherein $R^1$ and -$L^2$-$R^2$ are taken together to form a bivalent radical —$R^1$—$R^2$-$L^2$-, wherein —$R^1$—$R^2$-$L^2$- is selected from the group consisting of
    —CH=CH—CH=C(aryl$^1$)—, —CH=CH—N=C(aryl$^1$)—,
    —CH=CH—C($C_{1-4}$alkyl)=C(aryl$^1$)—, —(CH$_2$)$_2$—CH$_2$—CH(aryl$^1$)—,
    —(CH$_2$)$_2$—CH($C_{1-4}$alkyl)-CH(aryl$^1$)—, —(CH$_2$)$_2$—Y—CH(aryl$^1$)—,
    —CH=CH—C(aryl$^1$)=CH—, —(CH$_2$)$_2$—CH(aryl$^1$)—CH$_2$—, and
    —CH=CH—CH=C(1-piperidinyl)-; wherein 1-piperidinyl may be substituted with one or more trifluoromethyl groups;
    in particular wherein —$R^1$—$R^2$-$L^2$- is selected from the group consisting of —CH=CH—CH=C(aryl$^1$)—, —CH=CH—N=C(aryl$^1$)—, —CH=CH—C($C_{1-4}$alkyl)=C(aryl$^1$)—, —(CH$_2$)$_2$—CH$_2$—CH(aryl$^1$)—, —(CH$_2$)$_2$—CH($C_{1-4}$alkyl)-CH(aryl$^1$)—, —(CH$_2$)$_2$—Y—CH(aryl$^1$)—, —CH=CH—C(aryl$^1$)=CH—, and —(CH$_2$)$_2$—CH(aryl$^1$)—CH$_2$—.

An embodiment of the present invention relates to those compounds of Formula (I) and stereoisomeric forms thereof, or any subgroup thereof as mentioned in any of the other embodiments, wherein $R^1$ and -$L^2$-$R^2$ are taken together to form a bivalent radical —$R^1$—$R^2$-$L^2$-, wherein —$R^1$—$R^2$-$L^2$- is selected from the group consisting of —CH=CH—CH=C(aryl$^1$)—, —CH=CH—N=C(aryl$^1$)—, —CH=CH—C($C_{1-4}$alkyl)=C(aryl$^1$)—, —(CH$_2$)$_2$—CH$_2$—CH(aryl$^1$)—, —(CH$_2$)$_2$—CH($C_{1-4}$alkyl)-CH(aryl$^1$)—, —(CH$_2$)$_2$—Y—CH(aryl$^1$)—, —CH=CH—C(aryl$^1$)=CH—, —(CH$_2$)$_2$—CH(aryl$^1$)—CH$_2$—, and —CH=CH—CH=C(1-piperidinyl)-; wherein 1-piperidinyl may be substituted with one or more trifluoromethyl groups; wherein Y represents $NR^{14}$ or O;
    in particular wherein —$R^1$—$R^2$-$L^2$- is selected from the group consisting of —CH=CH—CH=C(aryl$^1$)—, —CH=CH—N=C(aryl$^1$)—, —CH=CH—C($C_{1-4}$alkyl)=C(aryl$^1$)—, —(CH$_2$)$_2$—CH$_2$—CH(aryl$^1$)—, —(CH$_2$)$_2$—CH($C_{1-4}$alkyl)-CH(aryl$^1$)—, —(CH$_2$)$_2$—Y—CH(aryl$^1$)—, —CH=CH—C(aryl$^1$)=CH—, and —(CH$_2$)$_2$—CH(aryl$^1$)—CH$_2$—; wherein Y represents $NR^{14}$ or O.

An embodiment of the present invention relates to those compounds of Formula (I) and stereoisomeric forms thereof, or any subgroup thereof as mentioned in any of the other embodiments, wherein $R^1$ and -$L^2$-$R^2$ are taken together to form a bivalent radical —$R^1$—$R^2$-$L^2$-, wherein —$R^1$—$R^2$-$L^2$- is selected from the group consisting of —CH=CH—CH=C(aryl$^1$)—, —CH=CH—N=C(aryl$^1$)—, —CH=CH—C($C_{1-4}$alkyl)=C(aryl$^1$)—, —CH$_2$—CH(aryl$^1$)—, —(CH$_2$)$_2$—CH($C_{1-4}$alkyl)-CH(aryl$^1$)—, —(CH$_2$)$_2$—$NR^{14}$—CH(aryl$^1$)—, —(CH$_2$)$_2$—

O—CH(aryl¹)—, —CH=CH—C(aryl¹)=CH—, —(CH₂)₂—CH(aryl¹)—CH₂—, and —CH=CH—CH=C(1-piperidinyl)-;

wherein 1-piperidinyl may be substituted with one or more trifluoromethyl groups;

wherein R¹⁴ represents H, $C_{1-4}$alkylcarbonyl or $C_{1-4}$alkyl;

in particular wherein —R¹—R²-L²- is selected from the group consisting of —CH=CH—CH=C(aryl¹)—, —CH=CH—N=C(aryl¹)—, —CH=CH—C($C_{1-4}$alkyl)=C(aryl¹)—, —(CH₂)₂—CH₂—CH(aryl¹)—, —(CH₂)₂—CH($C_{1-4}$alkyl)-CH(aryl¹)—, —(CH₂)₂—NR¹⁴—CH(aryl¹)—, —(CH₂)₂—O—CH(aryl¹)—, —CH=CH—C(aryl¹)=CH—, and —(CH₂)₂—CH(aryl¹)—CH₂—;

wherein R¹⁴ represents H, $C_{1-4}$alkylcarbonyl or $C_{1-4}$alkyl.

Another embodiment of the present invention relates to those compounds of Formula (I) or any subgroup thereof as mentioned in any of the other embodiments wherein Het¹ is a heterocycle having formula (a-1).

An embodiment of the present invention relates to those compounds of Formula (I) and stereoisomeric forms thereof, or any subgroup thereof as mentioned in any of the other embodiments, wherein R¹ and -L²-R² are taken together to form a bivalent radical —R¹—R²-L²- having formula (b-1), (b-2), (b-3), (b-4), or (b-5), —(CH₂)$_{m-n}$—Y—(CH₂)$_n$— (b-1);

—(CH₂)$_n$—Y—(CH₂)$_{m-n}$— (b-2);

—CH=CH—CH=CH— (b-3);

—CH=CH—N=CH— (b-4);

—CH=N—CH=CH— (b-5);

wherein (b-1) or (b-2) may contain one unsaturated bond;
wherein (b-1), (b-2) or the radical containing one unsaturated bond, may be substituted on one or more carbon atoms with one or where possible two substituents each independently selected from the group consisting of aryl¹, (C=O)-aryl¹, O-aryl¹, NR¹³ᵈ-aryl¹, $C_{1-4}$alkylcarbonyl, halo, hydroxy, and $C_{1-4}$alkyl optionally substituted with one or more halo substituents;
wherein (b-3), (b-4), or (b-5) may be substituted where possible with one or more substituents each independently selected from the group consisting of aryl¹, 1-piperidinyl, 1-pyrrolidinyl, 4-morpholinyl, (C=O)-aryl¹, O-aryl¹, NR¹³ᶠ-aryl¹, $C_{1-4}$alkylcarbonyl, and $C_{1-4}$alkyl optionally substituted with one or more halo substituents;
 wherein said 1-piperidinyl, 1-pyrrolidinyl, or 4-morpholinyl may be substituted with one or more trifluoromethyl groups; and
wherein Y represents NR¹⁴ or O.

An embodiment of the present invention relates to those compounds of Formula (I) and stereoisomeric forms thereof, or any subgroup thereof as mentioned in any of the other embodiments, wherein R¹ and -L²-R² are taken together to form a bivalent radical —R¹—R²-L²- having formula (b-3), (b-4), or (b-5), —CH=CH—CH=CH— (b-3);

—CH=CH—N=CH— (b-4);

—CH=N—CH=CH— (b-5);

wherein (b-3), (b-4), or (b-5) may be substituted where possible with one or more substituents each independently selected from the group consisting of aryl¹, 1-piperidinyl, 1-pyrrolidinyl, 4-morpholinyl, (C=O)-aryl¹, O-aryl¹, NR¹³ᶠ-aryl¹, $C_{1-4}$alkylcarbonyl, and $C_{1-4}$alkyl optionally substituted with one or more halo substituents;
 wherein said 1-piperidinyl, 1-pyrrolidinyl, or 4-morpholinyl may be substituted with one or more trifluoromethyl groups.

Another embodiment of the present invention relates to those compounds of Formula (I) or any subgroup thereof as mentioned in any of the other embodiments wherein one or more of the following restrictions apply
(i) m represents 3 or 4; in particular 3; or in particular m represents 4;
(ii) q represents 3, 4, 5 or 6; in particular 3, 4 or 5; more in particular 3 or 4; even more in particular 3;
(iii) r represents 0, 1, 2 or 3; in particular 0, 1 or 2; more in particular 0 or 1; even more in particular 0; or even more in particular r represents 1.

Another embodiment of the present invention relates to those compounds of Formula (I) or any subgroup thereof as mentioned in any of the other embodiments wherein R⁴, R⁵, R⁶, and R⁸ each independently are hydrogen or $C_{1-4}$alkyl.

An embodiment of the present invention relates to those compounds of Formula (I) and stereoisomeric forms thereof, or any subgroup thereof as mentioned in any of the other embodiments, wherein L¹ is NH.

An embodiment of the present invention relates to those compounds of Formula (I) and stereoisomeric forms thereof, or any subgroup thereof as mentioned in any of the other embodiments, wherein aryl¹ represents phenyl optionally substituted with one or more substituents each independently selected from the group consisting of halo, $C_{1-4}$alkyloxy, cyano, NR¹¹ᵉR¹²ᵉ, morpholinyl, and $C_{1-4}$alkyl optionally substituted with one or more halo substituents;
or a 5- or 6-membered heteroaryl selected from the group consisting of furanyl, thiophenyl, pyrazolyl, oxazolyl, isoxazolyl, thiazolyl, isothiazolyl, thiadiazolyl, oxadiazolyl, pyridinyl, pyrimidinyl, pyridazinyl, and pyrazinyl, wherein said 5- or 6-membered heteroaryl may be substituted with one or more substituents each independently selected from the group consisting of halo, $C_{1-4}$alkyloxy, cyano, NR¹¹ᶠR¹²ᶠ, morpholinyl, and
$C_{1-4}$alkyl optionally substituted with one or more halo substituents.

Another embodiment of the present invention relates to those compounds of Formula (I) or any subgroup thereof as mentioned in any of the other embodiments wherein the structure of the heterocycle (a-3) is restricted to (a-3a)

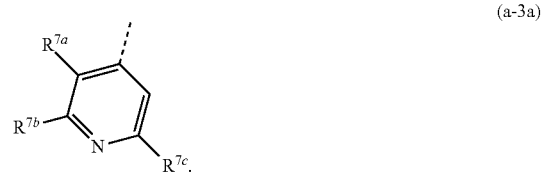

(a-3a)

It should be understood that any bivalent radical, in particular the bivalent radical —R¹—R²-L²-, in any of the embodiments hereabove may be substituted with substituents as listed in any of the other embodiments.

Another embodiment of the present invention relates to those compounds of formula (I) or any subgroup thereof as mentioned in any of the other embodiments wherein the expression "on one or more CH$_2$ groups" is restricted to "on one or two CH$_2$ groups".

In an embodiment the compound of Formula (I) is selected from the group comprising:

N-[8-(4-fluorophenyl)-5,6,7,8-tetrahydro[1,2,4]triazolo[1,5-a]pyridin-2-yl]-3-methoxy-4-(4-methyl-1H-imidazol-1-yl)-benzamide, 8-(2-chlorophenyl)-N-[3-methoxy-4-(4-methyl-1H-imidazol-1-yl)phenyl]-[1,2,4]triazolo[1,5-a]pyridin-2-amine, 8-[4-fluoro-2-(trifluoromethyl)phenyl]-N-[3-methoxy-4-(4-methyl-1H-imidazol-1-yl)phenyl]-[1,2,4]triazolo[1,5-a]pyridin-2-amine, 8-(4-fluorophenyl)-5,6,7,8-tetrahydro-N-[3-methoxy-4-(4-methyl-1H-imidazol-1-yl)phenyl]-[1,2,4]triazolo[1,5-a]pyridin-2-amine, 8-(2-chlorophenyl)-N-[3-methoxy-4-(2-methyl-4-pyridinyl)phenyl]-[1,2,4]triazolo[1,5-a]pyridin-2-amine, 8-(4-fluorophenyl)-5,6,7,8-tetrahydro-N-[3-methoxy-4-(2-methyl-4-pyridinyl)phenyl]-[1,2,4]triazolo[1,5-a]pyridin-2-amine, N-[3-methoxy-4-(4-methyl-1H-imidazol-1-yl)phenyl]-8-[2-(trifluoromethyl)phenyl]-[1,2,4]triazolo[1,5-a]pyrazin-2-amine, 8-[4-fluoro-2-(trifluoromethyl)phenyl]-N-[3-methoxy-4-(3-methyl-1H-1,2,4-triazol-1-yl)phenyl]-[1,2,4]triazolo[1,5-a]pyridin-2-amine, N-[3-methoxy-4-(3-methyl-1H-1,2,4-triazol-1-yl)phenyl]-8-[2-(trifluoromethyl)phenyl]-[1,2,4]triazolo[1,5-a]pyridin-2-amine, 5,6,7,8-tetrahydro-N-[3-methoxy-4-(4-methyl-1H-imidazol-1-yl)phenyl]-8-[2-(trifluoromethyl)phenyl]-[1,2,4]triazolo[1,5-a]pyrazin-2-amine, 5,6,7,8-tetrahydro-N-[3-methoxy-4-(3-methyl-1H-1,2,4-triazol-1-yl)phenyl]-8-[2-(trifluoromethyl)phenyl]-[1,2,4]triazolo[1,5-a]pyridin-2-amine, 5,6,7,8-tetrahydro-N-[3-methoxy-4-(4-methyl-1H-imidazol-1-yl)phenyl]-7-methyl-8-[2-(trifluoromethyl)phenyl]-[1,2,4]triazolo[1,5-a]pyrazin-2-amine, 8-(4-fluoro-2-methylphenyl)-N-[3-methoxy-4-(4-methyl-1H-imidazol-1-yl)phenyl]-[1,2,4]triazolo[1,5-a]pyrazin-2-amine, 7-acetyl-5,6,7,8-tetrahydro-N-[3-methoxy-4-(4-methyl-1H-imidazol-1-yl)phenyl]-8-[2-(trifluoromethyl)phenyl]-[1,2,4]triazolo[1,5-a]pyrazin-2-amine, 8-(4-fluoro-2-methylphenyl)-N-[3-methoxy-4-(4-methyl-1H-imidazol-1-yl)phenyl]-[1,2,4]triazolo[1,5-a]pyridin-2-amine, N-[3-methoxy-4-(4-methyl-5-oxazolyl)phenyl]-8-[2-(trifluoromethyl)phenyl]-[1,2,4]triazolo[1,5-a]pyridin-2-amine, N-[4-(4-methyl-5-oxazolyl)phenyl]-8-[2-(trifluoromethyl)phenyl]-[1,2,4]triazolo[1,5-a]pyridin-2-amine, N-[3-methoxy-4-(4-methyl-1H-imidazol-1-yl)phenyl]-8-[3-(trifluoromethyl)phenyl]-[1,2,4]triazolo[1,5-a]pyridin-2-amine, 8-(4-fluoro-2-methylphenyl)-5,6,7,8-tetrahydro-N-[3-methoxy-4-(4-methyl-1H-imidazol-1-yl)phenyl]-[1,2,4]triazolo[1,5-a]pyridin-2-amine, 5,6,7,8-tetrahydro-N-[3-methoxy-4-(2-methyl-4-pyridinyl)phenyl]-8-[2-(trifluoromethyl)phenyl]-[1,2,4]triazolo[1,5-a]pyridin-2-amine, 5,6,7,8-tetrahydro-N-[4-(2-methyl-4-pyridinyl)phenyl]-8-[2-(trifluoromethyl)phenyl]-[1,2,4]triazolo[1,5-a]pyridin-2-amine, 5,6,7,8-tetrahydro-N-[3-methoxy-4-(4-methyl-1H-imidazol-1-yl)phenyl]-8-[2-(trifluoromethyl)phenyl]-[1,2,4]triazolo[1,5-a]pyridin-2-amine, 5,6,7,8-tetrahydro-N-[3-methoxy-4-(4-methyl-1H-imidazol-1-yl)phenyl]-8-[3-(trifluoromethyl)phenyl]-[1,2,4]triazolo[1,5-a]pyridin-2-amine, 5,6,7,8-tetrahydro-N-[3-methoxy-4-(4-methyl-5-oxazolyl)phenyl]-8-[2-(trifluoromethyl)phenyl]-[1,2,4]triazolo[1,5-a]pyridin-2-amine, 8-(2-chlorophenyl)-5,6,7,8-tetrahydro-N-[4-(2-methyl-4-pyridinyl)phenyl]-[1,2,4]triazolo[1,5-a]pyridin-2-amine, 5,6,7,8-tetrahydro-N-[3-methoxy-4-(4-methyl-1H-imidazol-1-yl)phenyl]-N-methyl-8-[2-(trifluoromethyl)phenyl]-[1,2,4]triazolo[1,5-a]pyridin-2-amine HCl, 5,6,7,8-tetrahydro-N-[4-(2-methyl-5-oxazolyl)phenyl]-8-[2-(trifluoromethyl)phenyl]-[1,2,4]triazolo[1,5-a]pyridin-2-amine, 5,6,7,8-tetrahydro-N-[4-(4-methyl-5-oxazolyl)phenyl]-8-[2-(trifluoromethyl)phenyl]-[1,2,4]triazolo[1,5-a]pyridin-2-amine, 8-(2-chlorophenyl)-5,6,7,8-tetrahydro-N-[3-methoxy-4-(4-methyl-1H-imidazol-1-yl)phenyl]-[1,2,4]triazolo[1,5-a]pyridin-2-amine, 8-(2-chlorophenyl)-N-[3-fluoro-4-(2-methyl-4-pyridinyl)phenyl]-[1,2,4]triazolo[1,5-a]pyridin-2-amine, 8-(2-chlorophenyl)-N-[4-(2,6-dimethyl-4-pyridinyl)phenyl]-[1,2,4]triazolo[1,5-a]pyridin-2-amine, N-[3-methoxy-4-(4-methyl-1H-imidazol-1-yl)phenyl]-8-[3-(trifluoromethyl)phenyl]-[1,2,4]triazolo[1,5-a]pyrazin-2-amine, (8R)-8-(2-chlorophenyl)-5,6,7,8-tetrahydro-N-[3-methoxy-4-(4-methyl-1H-imidazol-1-yl)phenyl]-[1,2,4]triazolo[1,5-a]pyridin-2-amine, (8S)-8-(2-chlorophenyl)-5,6,7,8-tetrahydro-N-[3-methoxy-4-(4-methyl-1H-imidazol-1-yl)phenyl]-[1,2,4]triazolo[1,5-a]pyridin-2-amine, 8-[2-fluoro-5-(trifluoromethyl)phenyl]-N-[3-methoxy-4-(4-methyl-1H-imidazol-1-yl)phenyl]-[1,2,4]triazolo[1,5-a]pyridin-2-amine, 5,6,7,8-tetrahydro-N-[3-methoxy-4-(4-methyl-1H-imidazol-1-yl)phenyl]-8-(3-methoxyphenyl)-[1,2,4]triazolo[1,5-a]pyridin-2-amine.2HCl.H$_2$O, N-[4-(2,5-dimethyl-4-pyridinyl)phenyl]-5,6,7,8-tetrahydro-8-[2-(trifluoromethyl)phenyl]-[1,2,4]triazolo[1,5-a]pyridin-2-amine, 8-(4-fluorophenyl)-5,6,7,8-tetrahydro-N-(2-methoxy-2'-methyl[3,4'-bipyridin]-6-yl)-[1,2,4]triazolo[1,5-a]pyridin-2-amine, 8-(4-fluoro-2-methylphenyl)-N-[6-methoxy-5-(4-methyl-1H-imidazol-1-yl)-2-pyridinyl]-[1,2,4]triazolo[1,5-a]pyrazin-2-amine, 8-(4-fluoro-2-methylphenyl)-N-(2-methoxy-2'-methyl[3,4'-bipyridin]-6-yl)-[1,2,4]triazolo[1,5-a]pyrazin-2-amine, 8-(3-fluorophenyl)-5,6,7,8-tetrahydro-N-[3-methoxy-4-(4-methyl-1H-imidazol-1-yl)phenyl]-[1,2,4]triazolo[1,5-a]pyridin-2-amine, 5,6,7,8-tetrahydro-N-[3-methoxy-4-(2-methyl-4-pyridinyl)phenyl]-8-(3-methoxyphenyl)-[1,2,4]triazolo[1,5-a]pyridin-2-amine.1.8 HCl.0.9H$_2$O, 8-(3-fluorophenyl)-5,6,7,8-tetrahydro-N-[3-methoxy-4-(2-methyl-4-pyridinyl)phenyl]-[1,2,4]triazolo[1,5-a]pyridin-2-amine, N-[3-methoxy-4-(4-methyl-1H-imidazol-1-yl)phenyl]-7-[2-(trifluoromethyl)phenyl]-[1,2,4]triazolo[1,5-a]pyridin-2-amine, 5,6,7,8-tetrahydro-N-[3-methoxy-4-(2-methyl-4-pyridinyl)phenyl]-7-[2-(trifluoromethyl)phenyl]-[1,2,4]triazolo[1,5-a]pyridin-2-amine HCl, 8-(2-chlorophenyl)-N-[3-methoxy-4-(4-methyl-1H-imidazol-1-yl)phenyl]-[1,2,4]triazolo[1,5-a]pyridine-2-carboxamide, 5,6-dihydro-N-[3-methoxy-4-(2-methyl-4-pyridinyl)phenyl]-8-[2-(trifluoromethyl)phenyl]-8H-[1,2,4]triazolo[5,1-c][1,4]oxazin-2-amine, 8-(2-chlorophenyl)-5,6,7,8-tetrahydro-N-[3-methoxy-4-(2-methyl-4-pyridinyl)phenyl]-[1,2,4]triazolo[1,5-a]pyridin-2-amine, 8-(4-fluoro-2-methylphenyl)-N-[6-methoxy-5-(4-methyl-1H-imidazol-1-yl)-2-pyridinyl]-[1,2,4]triazolo[1,5-a]pyrazin-2-amine.HCl, 8-(4-fluoro-2-methylphenyl)-N-(2-methoxy-2'-methyl[3,4'-bipyridin]-6-yl)-[1,2,4]triazolo[1,5-a]pyrazin-2-amine.HCl, 8-[2-fluoro-5-(trifluoromethyl)phenyl]-5,6,7,8-tetrahydro-N-[3-methoxy-4-(2-methyl-4-pyridinyl)phenyl]-[1,2,4]triazolo[1,5-a]pyridin-2-amine, 8-(2-fluorophenyl)-5,6,7,8-tetrahydro-N-[3-methoxy-4-(2-methyl-4-pyridinyl)phenyl]-[1,2,4]triazolo[1,5-a]pyridin-2-amine, 5,6,7,8-tetrahydro-N-[3-methoxy-4-(2-methyl-4-pyridinyl)phenyl]-8-[4-(trifluoromethyl)phenyl]-[1,2,4]triazolo[1,5-a]pyridin-2-amine, 8-[3-(dimethylamino)phenyl]-5,6,7,8-tetrahydro-N-[3-methoxy-4-(2-methyl-4-pyridinyl)phenyl]-[1,2,4]triazolo[1,5-a]pyridin-2-amine, 8-(2,4-difluorophenyl)-5,6,7,8-tetrahydro-N-[3-methoxy-4-(2-methyl-4-pyridinyl)phenyl]-[1,2,4]triazolo[1,5-a]pyridin-2-amine, 8-(2,4-difluorophenyl)-5,6,7,8-tetrahydro-N-[4-(2-methyl-4-pyridinyl)phenyl]-[1,2,4]triazolo[1,5-a]pyridin-2-amine, 8-(2-fluoro-5-methoxyphenyl)-5,6,7,8-tetrahydro-N-[3-methoxy-4-(2-methyl-4-pyridinyl)phenyl]-[1,2,4]triazolo[1,5-a]pyridin-2-amine.1.7HCl, 8-[2-fluoro-5-(trifluoromethyl)phenyl]-5,6,7,8-tetrahydro-N-[4-(2-methyl-4-pyridinyl)phenyl]-[1,2,4]triazolo[1,5-a]pyridin-2-amine, 8-(2-fluoro-5-methoxyphenyl)-5,6,7,8-tetrahydro-N-[4-(2-methyl-4-pyridinyl)phenyl]-[1,2,4]triazolo[1,5-a]pyridin-2-amine, 8-(3-fluoro-5-methoxyphenyl)-5,6,7,8-tetrahydro-N-[3-methoxy-4-(2-methyl-4-pyridinyl)phenyl]-[1,2,4]triazolo[1,5-a]pyridin-2-amine, 8-(3-fluoro-5-methoxyphenyl)-5,6,7,8-tetrahydro-N-[4-(2-methyl-4-pyridinyl)phenyl]-[1,2,4]triazolo[1,5-a]pyridin-2-amine, 5,6,7,8-tetrahydro-N-[4-(4-pyridinyl)phenyl]-8-[2-(trifluoromethyl)phenyl]-[1,2,4]triazolo[1,5-a]pyridin-2-amine, 8-(4-fluoro-2-methylphenyl)-5,6,7,8-tetrahydro-N-[4-(2-methyl-4-pyridinyl)phenyl]-[1,2,4]triazolo[1,5-a]pyridin-2-amine, (8S)-8-(4-fluoro-2-methylphenyl)-5,6,7,8-tetrahydro-N-[4-(2-methyl-4-pyridinyl)phenyl]-[1,2,4]triazolo[1,5-a]pyridin-2-amine, (8R)-8-(4-fluoro-2-methylphenyl)-5,6,7,8-tetrahydro-N-[4-(2-methyl-4-pyridinyl)phenyl]-[1,2,4]triazolo[1,5-a]pyridin-2-amine, 8-(4-fluoro-2-methylphenyl)-5,6,7,8-tetrahydro-N-[3-methoxy-4-(2-methyl-4-pyridinyl)phenyl]-[1,2,4]triazolo[1,5-a]pyridin-2-amine, 5,6,7,8-tetrahydro-8-(3-methoxyphenyl)-N-[4-(2-methyl-4-pyridinyl)phenyl]-[1,2,4]triazolo[1,5-a]pyridin-2-amine, 8-(4-fluorophenyl)-N-[3-methoxy-4-(2-methyl-4-pyridinyl)phenyl]-7-methyl-[1,2,4]triazolo[1,5-a]pyridin-2-amine, 8-(3-fluoro-4-methoxyphenyl)-5,6,7,8-tetrahydro-N-[4-(2-methyl-4-pyridinyl)phenyl]-[1,2,4]triazolo[1,5-a]pyridin-2-amine.1.6HCl.2.4H₂O, 8-(3-fluoro-4-methoxyphenyl)-5,6,7,8-tetrahydro-N-[3-methoxy-4-(2-methyl-4-pyridinyl)phenyl]-[1,2,4]triazolo[1,5-a]pyridin-2-amine.1.3HCl.2.3H₂O, 8-(2-fluoro-5-methoxyphenyl)-N-[3-fluoro-4-(2-methyl-4-pyridinyl)phenyl]-5,6,7,8-tetrahydro-[1,2,4]triazolo[1,5-a]pyridin-2-amine, N-[3-fluoro-4-(2-methyl-4-pyridinyl)phenyl]-5,6,7,8-tetrahydro-8-(3-methoxyphenyl)-[1,2,4]triazolo[1,5-a]pyridin-2-amine, 8-(4-fluoro-3-methoxyphenyl)-5,6,7,8-tetrahydro-N-[4-(2-methyl-4-pyridinyl)phenyl]-[1,2,4]triazolo[1,5-a]pyridin-2-amine, 8-(4-fluoro-3-methoxyphenyl)-5,6,7,8-tetrahydro-N-[3-methoxy-4-(2-methyl-4-pyridinyl)phenyl]-[1,2,4]triazolo[1,5-a]pyridin-2-amine, N-[3-methoxy-4-(2-methyl-4-pyridinyl)phenyl]-8-[3-(trifluoromethyl)-1-piperidinyl]-[1,2,4]triazolo[1,5-a]pyridin-2-amine.1.5HCl.1.7H₂O, 5,6-dihydro-N-[4-(2-methyl-4-pyridinyl)phenyl]-8-[2-(trifluoromethyl)phenyl]-8H-[1,2,4]triazolo[5,1-c][1,4]oxazin-2-amine, N-[3-fluoro-4-(2-methyl-4-pyridinyl)phenyl]-5,6-dihydro-8-[2-(trifluoromethyl)phenyl]-8H-[1,2,4]triazolo[5,1-c][1,4]oxazin-2-amine, 8-(2-chlorophenyl)-5,6-dihydro-N-[4-(2-methyl-4-pyridinyl)phenyl]-8H-[1,2,4]triazolo[5,1-c][1,4]oxazin-2-amine, 8-(2-chlorophenyl)-5,6-dihydro-N-[3-methoxy-4-(2-methyl-4-pyridinyl)phenyl]-8H-[1,2,4]triazolo[5,1-c][1,4]oxazin-2-amine, 8-(2-chlorophenyl)-N-[3-fluoro-4-(2-methyl-4-pyridinyl)phenyl]-5,6-dihydro-8H-[1,2,4]triazolo[5,1-c][1,4]oxazin-2-amine, 8-(4-fluorophenyl)-5,6,7,8-tetrahydro-N-[3-methoxy-4-(2-methyl-4-pyridinyl)phenyl]-7-methyl-[1,2,4]triazolo[1,5-a]pyridin-2-amine, 8-(2-chloro-6-fluorophenyl)-5,6,7,8-tetrahydro-N-[4-(2-methyl-4-pyridinyl)phenyl]-[1,2,4]triazolo[1,5-a]pyridin-2-amine, 8-(2-chloro-6-fluorophenyl)-5,6,7,8-tetrahydro-N-[3-methoxy-4-(2-methyl-4-pyridinyl)phenyl]-[1,2,4]triazolo[1,5-a]pyridin-2-amine, 5,6,7,8-tetrahydro-N-[4-(2-methyl-4-pyridinyl)phenyl]-8-[2-methyl-5-(trifluoromethyl)phenyl]-[1,2,4]triazolo[1,5-a]pyridin-2-amine, 5,6,7,8-tetrahydro-N-[3-methoxy-4-(2-methyl-4-pyridinyl)phenyl]-8-[2-methyl-5-(trifluoromethyl)phenyl]-[1,2,4]triazolo[1,5-a]pyridin-2-amine, 8-(4-fluoro-2-methylphenyl)-5,6-dihydro-N-[3-methoxy-4-(2-methyl-4-pyridinyl)phenyl]-8H-[1,2,4]triazolo[5,1-c][1,4]oxazin-2-amine, 8-(2,4-difluorophenyl)-5,6-dihydro-N-[3-methoxy-4-(2-methyl-4-pyridinyl)phenyl]-8H-[1,2,4]triazolo[5,1-c][1,4]oxazin-2-amine, 5,6,7,8-tetrahydro-N-[6-methoxy-5-(4-methyl-1H-imidazol-1-yl)-2-pyridinyl]-8-[2-(trifluoromethyl)phenyl]-[1,2,4]triazolo[1,5-a]pyridin-2-amine, 8-(2-chlorophenyl)-5,6,7,8-tetrahydro-N-[6-methoxy-5-(4-methyl-1H-imidazol-1-yl)-2-pyridinyl]-[1,2,4]triazolo[1,5-a]pyridin-2-amine, 5,6,7,8-tetrahydro-N-[4-(3-pyridinyl)phenyl]-8-[2-(trifluoromethyl)phenyl]-[1,2,4]triazolo[1,5-a]pyridin-2-amine, 5,6-dihydro-N-[3-methoxy-4-(4-methyl-1H-imidazol-1-yl)phenyl]-8-[2-(trifluoromethyl)phenyl]-8H-[1,2,4]triazolo[5,1-c][1,4]oxazin-2-amine,
8-[2-fluoro-5-(trifluoromethyl)phenyl]-5,6,7,8-tetrahydro-N-[3-methoxy-4-(4-methyl-1H-imidazol-1-yl)phenyl]-[1,2,4]triazolo[1,5-a]pyridin-2-amine,
8-(2-fluorophenyl)-5,6,7,8-tetrahydro-N-[3-methoxy-4-(4-methyl-1H-imidazol-1-yl)phenyl]-[1,2,4]triazolo[1,5-a]pyridin-2-amine,
5,6,7,8-tetrahydro-N-[3-methoxy-4-(4-methyl-1H-imidazol-1-yl)phenyl]-8-[4-(trifluoromethyl)phenyl][1,2,4]triazolo[1,5-a]pyridin-2-amine, -
5,6,7,8-tetrahydro-N-[3-methoxy-4-(4-methyl-1H-imidazol-1-yl)phenyl]-7-[2-(trifluoromethyl)phenyl]-[1,2,4]triazolo[1,5-a]pyridin-2-amine,
5,6,7,8-tetrahydro-N-[3-methoxy-4-(2-methyl-4-pyridinyl)phenyl]-5-[2-(trifluoromethyl)phenyl]-[1,2,4]triazolo[1,5-a]pyridin-2-amine 1.8 HCl3H$_2$O, stereoisomeric forms thereof,
and the pharmaceutically acceptable addition salts, the free bases and the solvates thereof.

In an embodiment the compound of Formula (I) is selected from the group comprising:
5,6,7,8-tetrahydro-N-[4-(2-methyl-4-pyridinyl)phenyl]-8-[2-(trifluoromethyl)phenyl]-[1,2,4]triazolo[1,5-a]pyridin-2-amine,
8-(2-chlorophenyl)-5,6,7,8-tetrahydro-N-[4-(2-methyl-4-pyridinyl)phenyl]-[1,2,4]triazolo[1,5-a]pyridin-2-amine,
8-(2-chlorophenyl)-5,6,7,8-tetrahydro-N-[3-methoxy-4-(2-methyl-4-pyridinyl)phenyl]-[1,2,4]triazolo[1,5-a]pyridin-2-amine, stereoisomeric forms thereof,
and the pharmaceutically acceptable addition salts, the free bases and the solvates thereof.

All possible combinations of the above-indicated interesting embodiments are considered to be embraced within the scope of this invention.

Preparation of the Compounds

The present invention also encompasses processes for the preparation of compounds of Formula (I) and subgroups thereof. In the reactions described, it can be necessary to protect reactive functional groups, for example hydroxy, amino, or carboxy groups, where these are desired in the final product, to avoid their unwanted participation in the reactions. Conventional protecting groups can be used in accordance with standard practice, for example, see T. W. Greene and P. G. M. Wuts in "Protective Groups in Organic Chemistry", John Wiley and Sons, 1999.

The compounds of Formula (I) and the subgroups thereof can be prepared by a succession of steps as described hereunder. They are generally prepared from starting materials which are either commercially available or prepared by standard means obvious to those skilled in the art. The compounds of the present invention can be also prepared using standard synthetic processes commonly used by those skilled in the art of organic chemistry.

The general preparation of some typical examples is shown below. All variables are defined as mentioned hereabove unless otherwise is indicated.

Experimental Procedure 1

In general compounds of Formula (I) where L$^1$ represents NH, hereby named compounds of formula (I-a), can be prepared as set out below in Scheme 1 wherein Halo is defined as Cl, Br or I, and wherein all other variables are defined as mentioned hereabove:

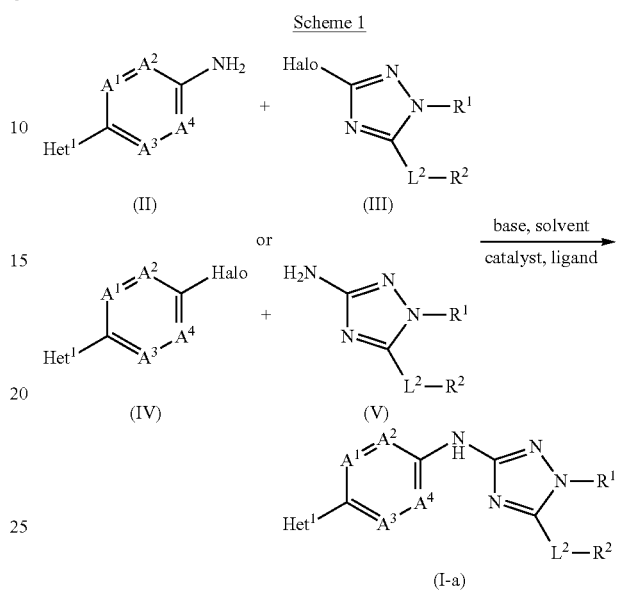

Compounds of formula (I-a) can be prepared via a coupling reaction between an intermediate of formula (II) and an intermediate of formula (III) or alternatively via a coupling reaction between an intermediate of formula (IV) and an intermediate of formula (V) (Scheme 1). This reaction may be performed in the presence of a suitable base such as, for example, Cs$_2$CO$_3$ or sodium tert-butoxide. The reaction can be performed in a reaction-inert solvent such as, for example, toluene, DMF, tert-butanol (t-BuOH) or dioxane. The reaction typically is performed in the presence of a catalyst system comprising of a suitable catalyst such as palladium(II) acetate (Pd(OAc)$_2$) or tris(dibenzylideneacetone)dipalladium (Pd$_2$(dba)$_3$) and a ligand such as (9,9-dimethyl-9H-xanthene-4,5-diyl)bis[diphenylphosphine] (Xantphos), [1,1'-binaphthalene]-2,2'-diylbis[diphenylphosphine] (BINAP), or dicyclohexyl[2',4',6'-tris(1-methylethyl) [1,1'-biphenyl]-2-yl]-phosphine (X-phos). Preferably this reaction is carried out under an inert atmosphere, such as nitrogen or argon. Reaction rate and yield may be enhanced by microwave assisted heating.

Experimental Procedure 2

Compounds of Formula (I) wherein L$^1$ represent (C=O)—NH, hereby named compounds of formula (I-b), can be prepared by standard amide bond formation reaction, using an intermediate of formula (V) as the amine source and an intermediate of formula (VI) as the carboxylic acid source. Alternatively, compounds of formula (I-b) can be prepared by a Pd-catalysed CO-insertion reaction between an intermediate of formula (IV) and an intermediate of formula (V). Both synthesis protocols are illustrated in Scheme 2, wherein Halo is defined as Cl, Br or I, and wherein all other variables are defined as mentioned before. Stirring at elevated temperatures (e.g. 150° C.) and/or pressure may enhance the rate of the reaction. The reaction can be charged with CO gas and may typically be performed in an organic solvent such as THF. The reaction can be catalysed by a Pd source such as, for example, tetrakis(triphenylphosphine)palladium (Pd(PPh$_3$)$_4$), Pd(OAc)$_2$ or Pd$_2$(dba)$_3$, in conjunction with an appropriate ligand.

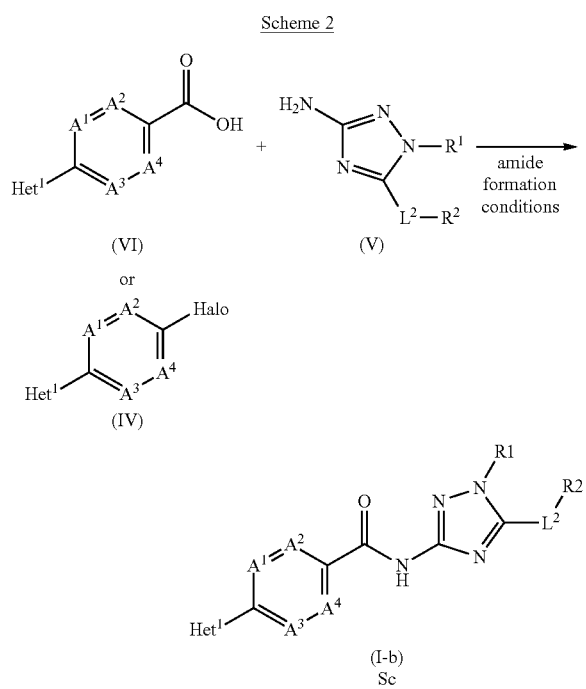

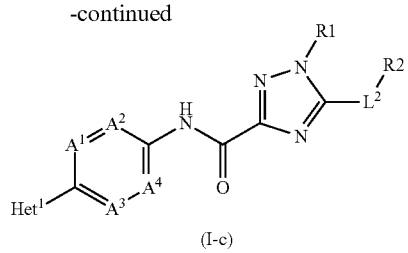

Alternatively, a compound of formula (I-c) can also be prepared by a standard amide bond formation reaction, using an amine source of formula (II) and the corresponding carboxylic acid derivative of the intermediate of formula (III). This reaction can be performed in typical reaction conditions, similarly to the conditions described in Experimental procedure 2.

Experimental Procedure 4

An intermediate of formula (IV), wherein all variables are defined as mentioned before, can be prepared by conversion of the amino-moiety in an intermediate of formula (II) into a halo-group, known as the Sandmeyer reaction (Scheme 4). In Scheme 4, Halo is defined as I, Br or Cl, and all other variables are defined as mentioned hereabove. Intermediate (II) is first converted to the corresponding diazonium salt by treatment with a nitrite source, such as NaNO$_2$ under acidic conditions, then treated with a halide source such as, for example, KI, CuBr or CuCl. Typical reaction conditions known to those skilled in the art can be used.

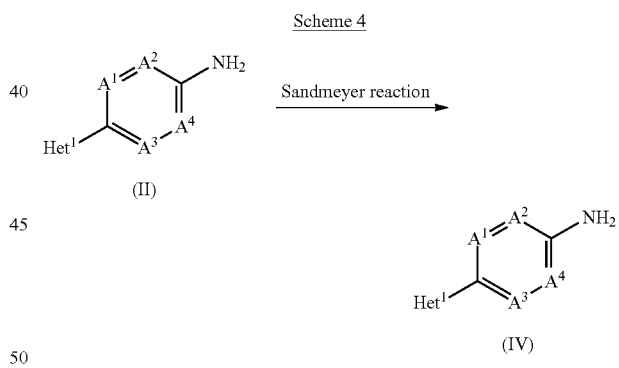

Experimental Procedure 3

Compounds of Formula (I) wherein L$^1$ represents NH—(C═O), hereby named compounds of formula (I-c), may be prepared by a Pd-catalysed CO-insertion reaction between an intermediate of formula (III) and an intermediate of formula (II), according to Scheme 3, wherein Halo is defined as Cl, Br or I and wherein all other variables are defined as mentioned here above. Stirring at elevated temperatures (for example 150° C.) and/or pressure may enhance the rate of the reaction. The reaction is charged with CO gas and is typically performed in an organic solvent such as, for example, THF. The reaction can be catalysed by a Pd source such as, for example, Pd(OAc)$_2$, Pd$_2$(dba)$_3$ or Pd(PPh$_3$)$_4$. An appropriate ligand may be added to the reaction.

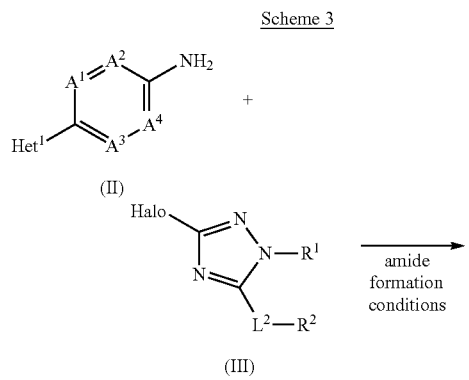

Experimental Procedure 5

An intermediate of formula (II), wherein all variables are defined as mentioned before, can be prepared by reduction of an intermediate of formula (VII), according to Scheme 5. The reduction of an intermediate of formula (VII) to an intermediate of formula (II) can be conducted by a conventional method such as reductive hydrogenation of reduction with a metal or a metal salt and an acid [for example a metal such as Fe, or a metal salt such as SnCl$_2$ and an acid such as an inorganic acid (HCl, H$_2$SO$_4$ or the like) or an organic acid (acetic acid or the like)]. Alternatively, other well-known methods for converting a nitro-group to its corresponding amine may be used.

Scheme 5

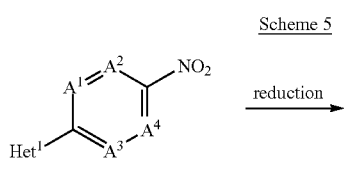

(VII)

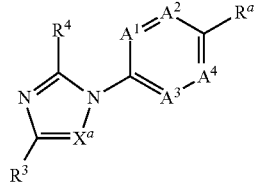

(X): $R^a$=NO$_2$, $R^a$=NH$_2$ (II)

Experimental Procedure 7

An intermediate of formula (VII) wherein Het$^1$ is restricted to oxazole substituted with R$^6$, hereby named intermediate of formula (XIII), can be prepared by a condensation reaction of an intermediate of formula (XI) with an intermediate of formula (XII) as is illustrated in Scheme 7. Intermediate (XI) may be commercially available or may be prepared according to conventional reaction procedures generally know in the art. This condensation reaction is performed in the presence of a suitable base such as, for example, K$_2$CO$_3$ or sodium ethoxide (NaOEt). The reaction can be performed in a protic solvent such as, for example, methanol (MeOH) or ethanol (EtOH). Stirring and/or elevated temperatures (for example between 70-110° C.) may enhance the rate of the reaction. In Scheme 7, all variables are defined as mentioned here above.

Experimental Procedure 6

Intermediates of formula (VII) or (II), wherein Het$^1$ is restricted to heterocycles having formula (a-1), wherein R$^a$ is defined as NO$_2$ or NH$_2$, and wherein other variables are defined as mentioned before, hereby named an intermediate of formula (X), can be prepared via a nucleophilic aromatic substitution of an intermediate of formula (IX) with an intermediate of formula (VIII), according to Scheme 6, wherein LG is defined as a leaving group such as, for example, F, Cl, Br, I, tosylate, mesylate or triflate, in particular F, Cl, Br or I, more in particular Cl, Br or I; and wherein all other variables are defined as mentioned here above. The reaction may be performed under an inert atmosphere such as, for example, N$_2$. Stirring at elevated temperatures (for example between 70-170° C.) and/or pressure may enhance the rate of the reaction. The reaction typically is performed in an organic solvent such as DMSO, DMF, or NMP (N-methylpyrrolidinone) in the presence of a base such as K$_2$CO$_3$, Cs$_2$CO$_3$, or Et$_3$N.

The reaction can be performed in the presence of a copper catalyst. Copper salts such as, for example, Cu$_2$O, CuI, or CuBr can be used in catalytic or stoichiometric amounts.

Scheme 7

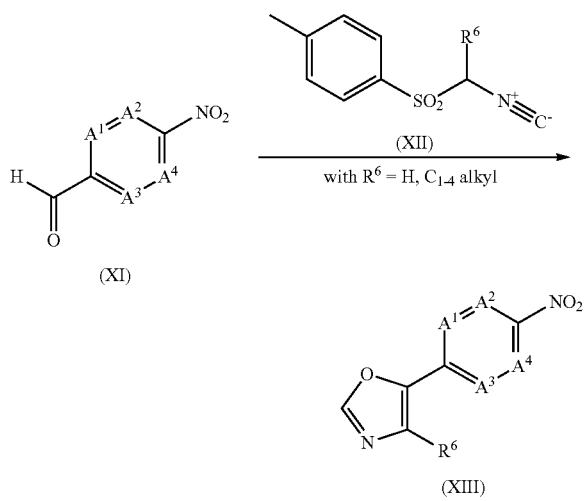

Experimental Procedure 8

An intermediate of formula (VII) wherein Het$^1$ is restricted to oxazole substituted with R$^5$ in the 2-position and CH$_3$ in the 4-position, hereby named an intermediate of formula (XIV), can be prepared by a condensation reaction of an intermediate of formula (XI) with an intermediate of formula (XV) according to Scheme 8 wherein all variables are defined as hereinbefore. Both intermediates may be commercially available or may be prepared according to conventional reaction procedures generally know in the art. This condensation reaction typically can be performed in a solvent such as pyridine. Stirring and/or elevated temperatures (e.g. between 70-110° C.) may enhance the rate of the reaction.

Scheme 6

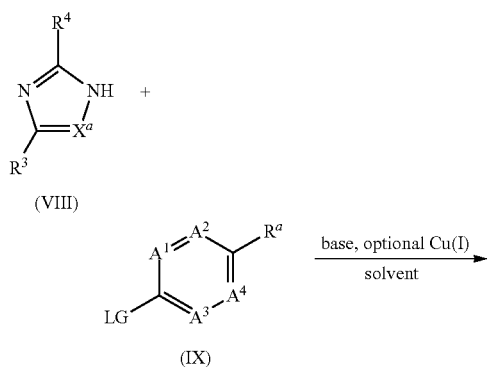

Scheme 8

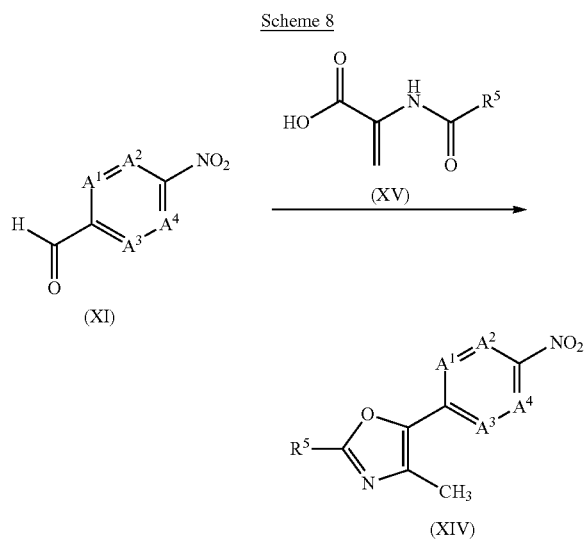

Experimental Procedure 9

Intermediates of formula (VII) or (II) wherein Het$^1$ is restricted to heterocycles (a-2), (a-3) or (a-4), hereby named an intermediate of formula (XVII), may be prepared by a Suzuki-Miyaura cross-coupling reaction between an intermediate of formula (XVI), wherein Het$^1$ is restricted to a heterocycle according to formula (a-2), (a-3) or (a-4), and an intermediate of formula (IX) wherein R$^a$ can be NO$_2$ or NH$_2$, according to Scheme 9. In formula (IX), LG$^a$ is defined as a leaving group such as, for example, Cl, Br, I, tosylate, mesylate or triflate, in particular Cl, Br or I; and in formula (XVI) B(OR)$_2$ refers to the boronic acid B(OH)$_2$ or its corresponding boronate ester, such as a pinacol ester. This reaction is catalysed by a Pd catalyst, such as, for example, Pd(PPh$_3$)$_4$ or [1,1'-bis(diphenylphosphino-κP)ferrocene]dichloropalladium (PdCl$_2$(dppf)). The reaction is performed in the presence of a suitable base, such as, for example K$_2$CO$_3$, or K$_3$PO$_4$ and in a reaction-inert solvent such as toluene, DMF, MeCN and may also include H$_2$O, Stirring at elevated temperatures (for example, between 50-120° C.) and/or pressure may enhance the rate of the reaction, which can be carried out using microwave irradiation, or by conventional heating.

Scheme 9

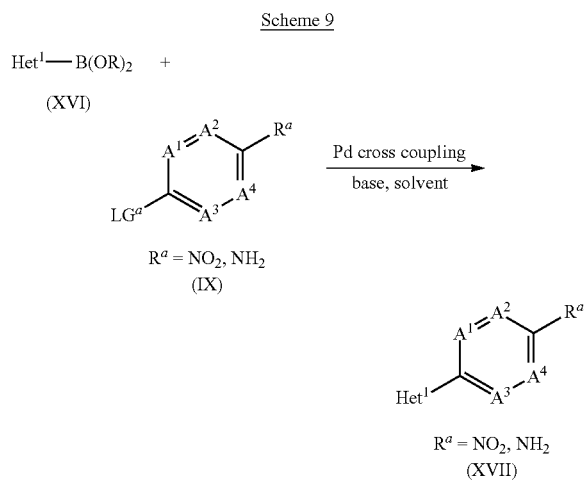

Experimental Procedure 10

An intermediate of formula (IV) wherein at least one of A$^1$ or A$^3$ represents N, and, wherein Het$^1$ is restricted to formula (a-1), and wherein all other variables are defined as mentioned before, hereby named an intermediate of formula (XIX), can be prepared via a nucleophilic aromatic substitution of an intermediate of formula (XVIII), wherein at least one of A$^1$ or A$^3$ represents N, with an optionally substituted imidazole or triazole of formula (VIII) according to Scheme 10, wherein LG is as defined as mentioned before, wherein Halo is defined as Br, Cl or I, and wherein all other substituents are defined as mentioned before. The reaction may be performed under similar reaction conditions as described for Experimental procedure 4.

Scheme 10

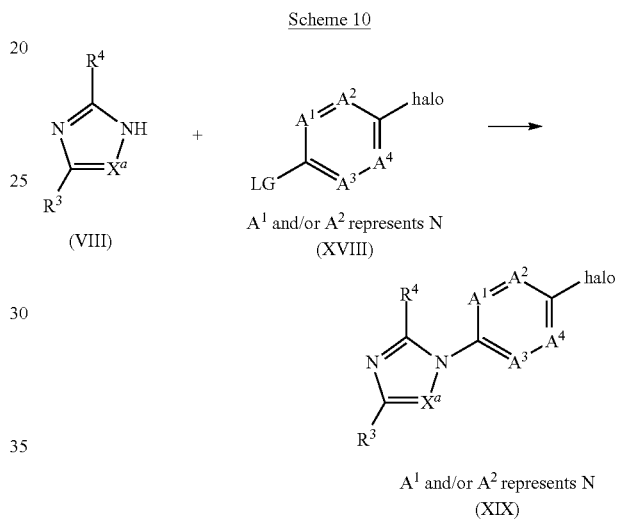

Experimental Procedure 11

An intermediate of formula (IV) wherein Het$^1$ represents the group of formula (a-1) wherein X$^a$ is restricted to CH, and wherein all other variables are defined as mentioned before, hereby named an intermediate of formula (XXIV), can be prepared via acylation of intermediate (XX) to yield intermediate (XXI) in the presence of a reaction inert solvent, such as, for example, THF, and optionally a suitable base, such as Et$_3$N, according to Scheme 11. An intermediate of formula (XXIII) can subsequently be prepared via alkylation of an intermediate of formula (XXI) with an intermediate of formula (XXII), in the presence of a reaction inert solvent such as, for example, DMF, and a suitable base such as, for example, Cs$_2$CO$_3$ or K$_2$CO$_3$, and optionally in the presence of a catalytic amount of a iodide salt such as, for example, KI or NaI. Finally, a condensation reaction of intermediate (XXIII) with an ammonia source such as, for example, ammonium acetate (NH$_4$OAc) yields a compound of formula (XXIV). In Scheme 11, Halo is defined as Cl, Br, or I, Halo$^a$ is defined as Cl or Br, and all other variables are defined as mentioned hereinbefore.

Scheme 11

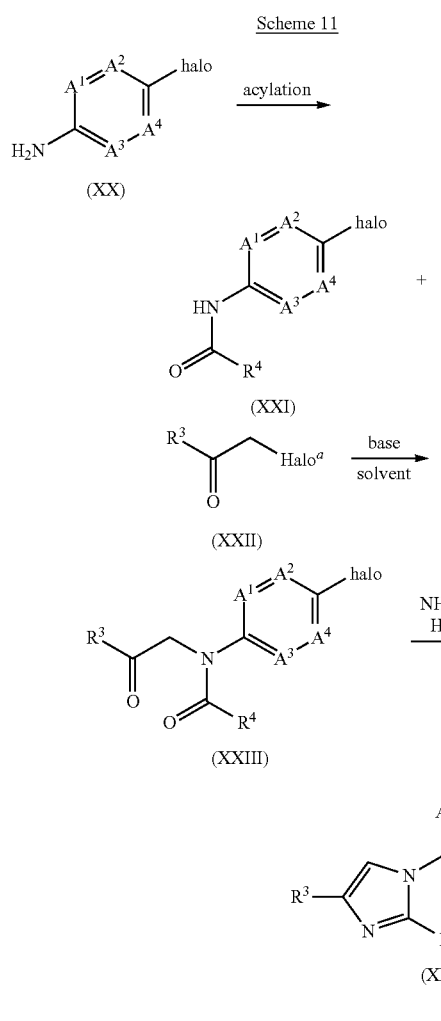

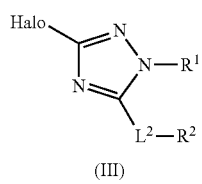

(III)

Experimental Procedure 13

An intermediate of formula (V), wherein $R^1$ and $-L^2-R^2$ are taken together to form a bivalent radical as shown in scheme 13, with t being 0 or 1, and wherein all other variables are defined as in compounds of Formula (I), hereby named intermediates of formula (V-b1), may be prepared by a condensation reaction between an intermediate of formula (XXXI) and an amino guanidine species (XXXII) according to Scheme 13. Stirring at elevated temperatures (e.g. 40-160° C.) and/or pressure may enhance the rate of the reaction, which can be carried out using microwave irradiation or by conventional heating. Typically an alcoholic solvent such as 2-propanol can be used.

Scheme 13

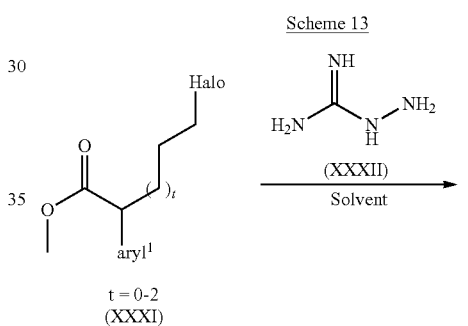

Experimental Procedure 12

An intermediate of formula (III), wherein all variables are defined as mentioned before, can be prepared by conversion of the amino-moiety in intermediate (V) into a halo-group via a Sandmeyer reaction (Scheme 12). In Scheme 12, Halo is defined as I, Br or Cl, and all other variables are defined as mentioned here above. Intermediate (V) is first converted to the corresponding diazonium salt by treatment with a nitrite source, such as $NaNO_2$ under acidic conditions or isoamyl nitrite or t-butyl nitrite in an organic solventy such as $CH_3CN$, then treated with a halide source such as KI, CuBr or CuCl. Typical reaction conditions known to those skilled in the art can be used.

Scheme 12

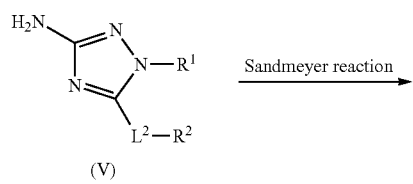

Experimental Procedure 14

Alternatively, an intermediate of formula (V-b1), can be prepared via intermediate of formula (XXXII-a) resulting from substitution reaction with hydrazine (step a) followed by a condensation reaction with an amidine bearing a leaving group $LG^b$ such as a benzotriazole (step b). The substitution reaction is performed in the presence of a suitable base, such as, for example NaH, and in a reaction-inert solvent such as DMF. This reaction is typically performed at low temperature or at r.t., however elevated temperatures (for example 40-160° C.) and/or pressure may enhance the rate of the reaction, which can be carried out using microwave irradiation or conventional heating. This type of reaction typically may be performed in an alcoholic solvent such as 2-propanol.

Scheme 14

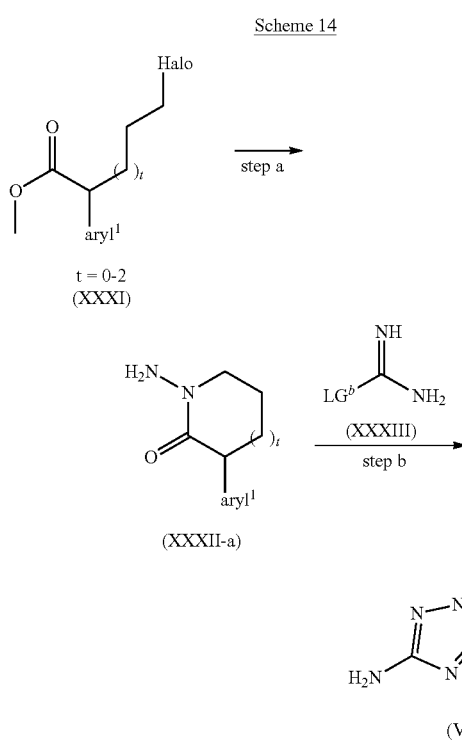

Experimental Procedure 15

An intermediate of formula (V), wherein $R^1$ and -$L^2$-$R^2$ are taken together to form a bivalent radical of formula —CH=CH—CH=CH— or —CH=CH—N=CH—, hereby named intermediates of formula (V-b2) ($Z^a$ representing N, CH or C—$C_{1-4}$alkyl (e.g. C—$CH_3$)), may be prepared starting by a condensation reaction between an intermediate of formula (XXXV) and an isothiocyanate species of formula (XXXVI) in a reaction inert solvent such as dioxane at r.t., according to scheme 15. This reaction is typically performed at low temperature or at r.t., however elevated temperatures (for example 40-160° C.) and/or pressure may enhance the rate of the reaction which can be carried out using microwave irradiation or conventional heating. The condensation reaction between an intermediate of formula (XXXVII) and an amine source such as hydroxyl amine to give intermediate (V-b2) typically can be performed in an appropriate alcoholic solvent such EtOH or MeOH at r.t., however elevated temperatures (for example 40-160° C.) in microwave and/or pressure may enhance the rate of the reaction.

Scheme 15

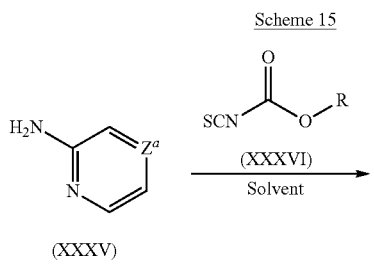

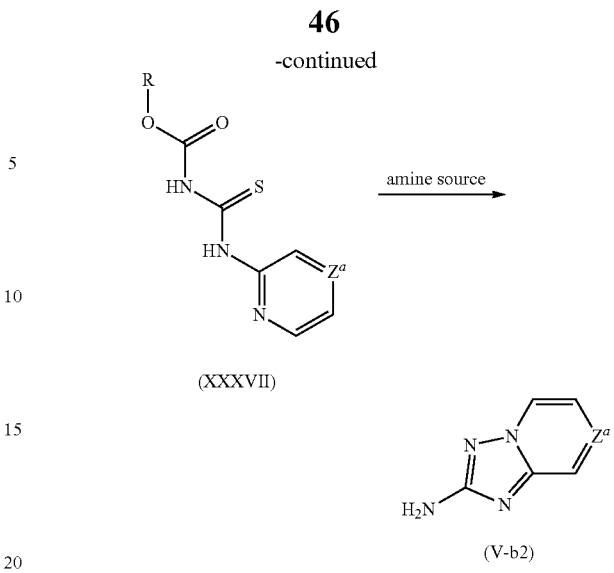

An analogous reaction procedure can be followed to prepare intermediates of formula (V-b2) wherein the bivalent radical —$R^1$—$R^2$-$L^2$- of formula —CH=CH—CH=CH— or —CH=CH—N=CH— is further substituted with substituents as defined for compounds of Formula (I). In this case typically a Pd mediated coupling of an intermediate of formula (XXXIV) with for example the corresponding amine, phenol, boronic acid or ester species is performed to obtain an intermediate of formula (XXXV-a) which can be further reacted in Scheme 15. Halo is defined as Br, Cl or I; $Z^a$ is defined as mentioned hereabove. This is illustrated below in Scheme 15a.

Scheme 15a

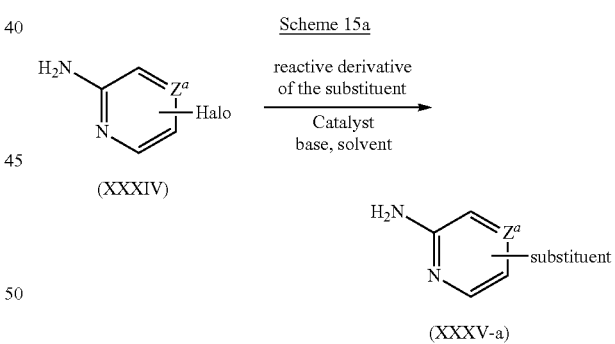

Alternatively, intermediates of formula (V-b2) wherein the bivalent radical —$R^1$—$R^2$-$L^2$- of formula —CH=CH—CH=CH— or —CH=CH—N=CH— is further substituted with substituents as defined for compounds of Formula (I), hereby named intermediates of formula (V-b4), can be obtained by converting an intermediate such as, for example, an intermediate of formula (XXXIV) to an intermediate of formula (V-b3) by following the reaction protocol described in Scheme 15. Subsequently, the intermediate of formula (V-b3) can be converted to an intermediate of formula (V-b4) in a Pd mediated coupling with for example the corresponding amine, phenol or boronic acid or ester species. This is illustrated below in Scheme 15b. All variables are defined as mentioned in Scheme 15a.

Scheme 15b

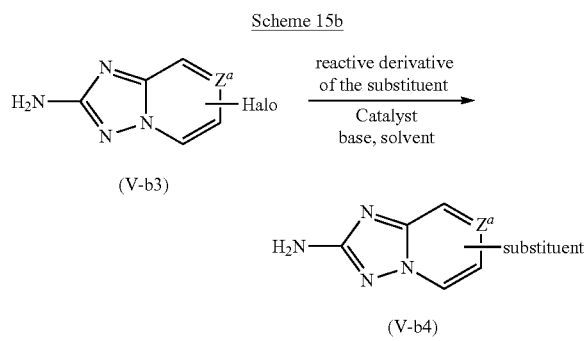

In case the substituent in formula (XXXV-a) or (V-b4) is aryl$^1$, the intermediate of formula (XXXIV) or (V-b3) respectively, can be reacted with a boronic acid (aryl$^1$-B(OH)$_2$) or ester derivative (aryl$^1$-B(OR)$_2$). This coupling reaction may be performed in a suitable solvent such as, for example, dioxane, in the presence of a Pd catalyst such as Pd(PPh$_3$)$_4$, and a base such as NaHCO$_3$ in the presence of H$_2$O. The reaction can be carried out using microwave irradiation or conventional heating (e.g. 150° C.).

In case the substituent in formula (XXXV-a) or (V-b4) is NR$^{13'}$-aryl$^1$, the intermediate of formula (XXXIV) or (V-b3) respectively, typically can be reacted with an amine derivative (H$_2$N-aryl$^1$) of aryl$^1$. This coupling reaction may be performed in a suitable solvent such as, for example, t-BuOH, in the presence of a Pd catalyst such as Pd$_2$(dba)$_3$, and a base such as Cs$_2$CO$_3$. The reaction can be carried out in the presence of a ligand such as, for example, X-Phos. Typically, the reaction can be carried out using conventional heating (e.g. 100° C.).

In case the substituent in formula (XXXV-a) or (V-b4) is O-aryl$^1$, the intermediate of formula (XXXIV) or (V-b3) respectively, typically can be reacted with a phenol derivative (HO-aryl$^1$) of aryl$^1$. This coupling reaction may be performed in a suitable solvent such as N,N-dimethylacetamide (DMA), in the presence of a copper catalyst. Copper salts such as, for example, Cu$_2$O, CuI, or CuBr are used. Usually a base such as K$_2$CO$_3$ is added to the reaction mixture. Typically, the reaction can be carried out using conventional heating (e.g. 150-175° C.).

In case the substituent in formula (XXXV-a) or (V-b4) is (C=O)-aryl$^1$ or C$_{1-4}$alkyl-carbonyl, the intermediate of formula (XXXIV) or (V-b3) respectively, typically can be reacted with the corresponding aldehyde of aryl$^1$ (aryl$^1$-(C=O)H) or C$_{1-4}$alkyl (C$_{1-4}$alkyl-(C=O)H). This coupling reaction typically may be performed in the presence of an organometallic compound, in particular an organolithium reagent such as n-butyl lithium. Usually the reaction can be carried out in a suitable solvent such as, for example, THF. In a final step, the hydroxyl group can be oxidized to the corresponding ketone, using reaction conditions known to those skilled in the art.

In case the substituent in formula (XXXV-a) or (V-b4) is C$_{1-4}$alkyl, the intermediate of formula (XXXIV) or (V-b3) respectively, typically can be reacted with the corresponding aldehyde. This coupling reaction typically may be performed in the presence of an organometallic compound, in particular an organolithium reagent such as n-butyl lithium. Usually the reaction can be carried out in a suitable solvent such as, for example, THF. Subsequently, the hydroxyl group can be converted to the tosylate by reaction with a tosyl chloride in the presence of a base such as, for example, Et$_3$N, in a suitable solvent such as typically DCM. In final step, the tosylate group may be removed with a reducing agent such as, for example, NaBH$_4$, in the presence of an alcoholic solvent such as MeOH. The reaction can be performed at r.t. or at elevated temperatures.

Experimental Procedure 16

The aromatic intermediates of formula (V-b2), (V-b3) and (V-b4) can be reduced to the corresponding reduced forms by conventional methods such as, for example, reductive hydrogenation or reduction with a metal or a metal salt and an acid [for example a metal such as Fe, or a metal salt such as SnCl$_2$ and an acid such as an inorganic acid (HCl, H$_2$SO$_4$ or the like) or an organic acid (acetic acid or the like)]. Alternatively, other well-known methods for converting an aromatic to its corresponding reduced form may be used.

An analogous reaction protocol may be used to convert compounds of Formula (I) wherein R$^1$ and -L$^2$-R$^2$ are taken together to form a bivalent radical of formula —CH=CH—CH=CH— or —CH=CH—N=CH— to their corresponding reduced forms.

Starting materials in the above described schemes are commercially available or can be prepared by those skilled in the art.

Where necessary or desired, any one or more of the following further steps in any order may be performed:
  Compounds of Formula (I), any subgroup thereof, addition salts, solvates, and stereochemical isomeric forms thereof can be converted into further compounds according to the invention using procedures known in the art.
  It will be appreciated by those skilled in the art that in the processes described above the functional groups of intermediate compounds may need to be blocked by protecting groups. In case the functional groups of intermediate compounds were blocked by protecting groups, they can be deprotected after a reaction step.

Pharmacology

It has been found that the compounds of the present invention modulate the γ-secretase activity. The compounds according to the invention and the pharmaceutically acceptable compositions thereof therefore may be useful in the treatment or prevention of AD, TBI, MCI, senility, dementia, dementia with Lewy bodies, cerebral amyloid angiopathy, multi-infarct dementia, Down's syndrome, dementia associated with Parkinson's disease and dementia associated with beta-amyloid, preferably AD.

The compounds according to the present invention and the pharmaceutically acceptable compositions thereof may be useful in the treatment or prevention of a disease or condition selected from the group consisting of AD, TBI, MCI, senility, dementia, dementia with Lewy bodies, cerebral amyloid angiopathy, multi-infarct dementia, dementia pugilistica, Down's syndrome, dementia associated with Parkinson's disease and dementia associated with beta-amyloid.

As used herein, the term "modulation of γ-secretase activity" refers to an effect on the processing of APP by the γ-secretase-complex. Preferably it refers to an effect in which the overall rate of processing of APP remains essentially as without the application of said compounds, but in which the relative quantities of the processed products are changed, more preferably in such a way that the amount of the Aβ42-peptide produced is reduced. For example a different Abeta species can be produced (e.g. Abeta-38 or other Abeta peptide species of shorter amino acid sequence instead of Abeta-42)

or the relative quantities of the products are different (e.g. the ratio of Abeta-40 to Abeta-42 is changed, preferably increased).

It has been previously shown that the γ-secretase complex is also involved in the processing of the Notch-protein. Notch is a signaling protein which plays a crucial role in developmental processes (e.g. reviewed in Schweisguth F (2004) Curr. Biol. 14, R129). With respect to the use of γ-secretase modulators in therapy, it seems particularly advantageous not to interfere with the Notch-processing activity of the γ-secretase activity in order to avoid putative undesired side-effects. While γ-secretase inhibitors show side effects due to concomitant inhibition of Notch processing, γ-secretase modulators may have the advantage of selectively decreasing the production of highly aggregatable and neurotoxic forms of Aβ, i.e. Aβ42, without decreasing the production of smaller, less aggregatable forms of Aβ, i.e. Aβ38 and without concomitant inhibition of Notch processing. Thus, compounds are preferred which do not show an effect on the Notch-processing activity of the γ-secretase-complex.

As used herein, the term "treatment" is intended to refer to all processes, wherein there may be a slowing, interrupting, arresting, or stopping of the progression of a disease, but does not necessarily indicate a total elimination of all symptoms.

The invention relates to a compound according to the general Formula (I), the stereoisomeric forms thereof and the pharmaceutically acceptable acid or base addition salts and the solvates thereof, for use as a medicament.

The invention also relates to a compound according to the general Formula (I), the stereoisomeric forms thereof and the pharmaceutically acceptable acid or base addition salts and the solvates thereof, for use in the modulation of γ-secretase activity.

The invention also relates to a compound according to the general Formula (I), the stereoisomeric forms thereof and the pharmaceutically acceptable acid or base addition salts and the solvates thereof, for use in the treatment or prevention of diseases or conditions selected from the group consisting of AD, TBI, MCI, senility, dementia, dementia with Lewy bodies, cerebral amyloid angiopathy, multi-infarct dementia, Down's syndrome, dementia associated with Parkinson's disease and dementia associated with beta-amyloid.

In an embodiment, said disease or condition is preferably AD.

The invention also relates to a compound according to the general Formula (I), the stereoisomeric forms thereof and the pharmaceutically acceptable acid or base addition salts and the solvates thereof, for use in the treatment of said diseases.

The invention also relates to a compound according to the general Formula (I), the stereoisomeric forms thereof and the pharmaceutically acceptable acid or base addition salts and the solvates thereof, for the treatment or prevention of said diseases.

The invention also relates to a compound according to the general formula (I), the stereoisomeric forms thereof and the pharmaceutically acceptable acid or base addition salts and the solvates thereof, for the treatment or prevention, in particular treatment, of γ-secretase mediated diseases or conditions.

The invention also relates to the use of a compound according to the general Formula (I), the stereoisomeric forms thereof and the pharmaceutically acceptable acid or base addition salts and the solvates thereof, for the manufacture of a medicament.

The invention also relates to the use of a compound according to the general Formula (I), the stereoisomeric forms thereof and the pharmaceutically acceptable acid or base addition salts and the solvates thereof, for the manufacture of a medicament for the modulation of γ-secretase activity.

The invention also relates to the use of a compound according to the general Formula (I), the stereoisomeric forms thereof and the pharmaceutically acceptable acid or base addition salts and the solvates thereof, for the manufacture of a medicament for the treatment or prevention of any one of the disease conditions mentioned hereinbefore.

The invention also relates to the use of a compound according to the general Formula (I), the stereoisomeric forms thereof and the pharmaceutically acceptable acid or base addition salts and the solvates thereof, for the manufacture of a medicament for the treatment of any one of the disease conditions mentioned hereinbefore.

In the invention, particular preference is given to compounds of Formula (I), or any subgroup thereof with a $IC_{50}$ value for the inhibition of the production of Aβ42-peptide of less than 1000 nM, preferably less than 100 nM, more preferably less than 50 nM, even more preferably less than 20 nM as determined by a suitable assay, such as the assay used in the Examples below.

The compounds of the present invention can be administered to mammals, preferably humans for the treatment or prevention of any one of the diseases mentioned hereinbefore.

In view of the utility of the compound of Formula (I), there is provided a method of treating warm-blooded animals, including humans, suffering from or a method of preventing warm-blooded animals, including humans, to suffer from any one of the diseases mentioned hereinbefore.

Said methods comprise the administration, i.e. the systemic or topical administration, preferably oral administration, of an effective amount of a compound of Formula (I), a stereoisomeric form thereof and a pharmaceutically acceptable addition salt or solvate thereof, to warm-blooded animals, including humans.

Those of skill in the treatment of such diseases could determine the effective therapeutic daily amount from the test results presented hereinafter. An effective therapeutic daily amount would be from about 0.005 mg/kg to 50 mg/kg, in particular 0.01 mg/kg to 50 mg/kg body weight, more in particular from 0.01 mg/kg to 25 mg/kg body weight, preferably from about 0.01 mg/kg to about 15 mg/kg, more preferably from about 0.01 mg/kg to about 10 mg/kg, even more preferably from about 0.01 mg/kg to about 1 mg/kg, most preferably from about 0.05 mg/kg to about 1 mg/kg body weight. The amount of a compound according to the present invention, also referred to here as the active ingredient, which is required to achieve a therapeutically effect will of course, vary on case-by-case basis, for example with the particular compound, the route of administration, the age and condition of the recipient, and the particular disorder or disease being treated.

A method of treatment may also include administering the active ingredient on a regimen of between one and four intakes per day. In these methods of treatment the compounds according to the invention are preferably formulated prior to administration.

As described herein below, suitable pharmaceutical formulations are prepared by known procedures using well known and readily available ingredients.

The compounds of the present invention, that can be suitable to treat or prevent Alzheimer's disease or the symptoms thereof, may be administered alone or in combination with one or more additional therapeutic agents. Combination therapy includes administration of a single pharmaceutical dosage formulation which contains a compound of Formula (I) and one or more additional therapeutic agents, as well as administration of the compound of Formula (I) and each additional therapeutic agents in its own separate pharmaceutical dosage formulation. For example, a compound of Formula (I) and a therapeutic agent may be administered to the patient together in a single oral dosage composition such as a tablet or capsule, or each agent may be administered in separate oral dosage formulations.

While it is possible for the active ingredient to be administered alone, it is preferable to present it as a pharmaceutical composition.

Accordingly, the present invention further provides a pharmaceutical composition comprising a pharmaceutically acceptable carrier and, as active ingredient, a therapeutically effective amount of a compound according to Formula (I).

The carrier or diluent must be "acceptable" in the sense of being compatible with the other ingredients of the composition and not deleterious to the recipients thereof.

For ease of administration, the subject compounds may be formulated into various pharmaceutical forms for administration purposes. The compounds according to the invention, in particular the compounds according to Formula (I), a pharmaceutically acceptable acid or base addition salt thereof, a stereochemically isomeric form thereof, or any subgroup or combination thereof may be formulated into various pharmaceutical forms for administration purposes. As appropriate compositions there may be cited all compositions usually employed for systemically administering drugs.

To prepare the pharmaceutical compositions of this invention, an effective amount of the particular compound, optionally in addition salt form, as the active ingredient is combined in intimate admixture with a pharmaceutically acceptable carrier, which carrier may take a wide variety of forms depending on the form of preparation desired for administration. These pharmaceutical compositions are desirable in unitary dosage form suitable, in particular, for administration orally, rectally, percutaneously, by parenteral injection or by inhalation. For example, in preparing the compositions in oral dosage form, any of the usual pharmaceutical media may be employed such as, for example, water, glycols, oils, alcohols and the like in the case of oral liquid preparations such as suspensions, syrups, elixirs, emulsions and solutions; or solid carriers such as starches, sugars, kaolin, diluents, lubricants, binders, disintegrating agents and the like in the case of powders, pills, capsules and tablets. Because of their ease in administration, tablets and capsules represent the most advantageous oral dosage unit forms in which case solid pharmaceutical carriers are obviously employed. For parenteral compositions, the carrier will usually comprise sterile water, at least in large part, though other ingredients, for example, to aid solubility, may be included. Injectable solutions, for example, may be prepared in which the carrier comprises saline solution, glucose solution or a mixture of saline and glucose solution. Injectable solutions, for example, may be prepared in which the carrier comprises saline solution, glucose solution or a mixture of saline and glucose solution. Injectable solutions containing compounds of Formula (I) may be formulated in an oil for prolonged action. Appropriate oils for this purpose are, for example, peanut oil, sesame oil, cottonseed oil, corn oil, soybean oil, synthetic glycerol esters of long chain fatty acids and mixtures of these and other oils. Injectable suspensions may also be prepared in which case appropriate liquid carriers, suspending agents and the like may be employed. Also included are solid form preparations that are intended to be converted, shortly before use, to liquid form preparations. In the compositions suitable for percutaneous administration, the carrier optionally comprises a penetration enhancing agent and/or a suitable wetting agent, optionally combined with suitable additives of any nature in minor proportions, which additives do not introduce a significant deleterious effect on the skin. Said additives may facilitate the administration to the skin and/or may be helpful for preparing the desired compositions. These compositions may be administered in various ways, e.g., as a transdermal patch, as a spot-on, as an ointment.

Acid or base addition salts of compounds of Formula (I) due to their increased water solubility over the corresponding base or acid form, are more suitable in the preparation of aqueous compositions.

It is especially advantageous to formulate the aforementioned pharmaceutical compositions in unit dosage form for ease of administration and uniformity of dosage. Unit dosage form as used herein refers to physically discrete units suitable as unitary dosages, each unit containing a predetermined quantity of active ingredient calculated to produce the desired therapeutic effect in association with the required pharmaceutical carrier. Examples of such unit dosage forms are tablets (including scored or coated tablets), capsules, pills, powder packets, wafers, suppositories, injectable solutions or suspensions and the like, and segregated multiples thereof.

Since the compounds according to the invention are potent orally administrable compounds, pharmaceutical compositions comprising said compounds for administration orally are especially advantageous.

In order to enhance the solubility and/or the stability of the compounds of Formula (I) in pharmaceutical compositions, it can be advantageous to employ α-, β- or γ-cyclodextrins or their derivatives, in particular hydroxyalkyl substituted cyclodextrins, e.g. 2-hydroxypropyl-β-cyclodextrin or sulfobutyl-β-cyclodextrin. Also co-solvents such as alcohols may improve the solubility and/or the stability of the compounds according to the invention in pharmaceutical compositions.

Depending on the mode of administration, the pharmaceutical composition will preferably comprise from 0.05 to 99% by weight, more preferably from 0.1 to 70% by weight, even more preferably from 0.1 to 50% by weight of the compound of Formula (I), and, from 1 to 99.95% by weight, more preferably from 30 to 99.9% by weight, even more preferably from 50 to 99.9% by weight of a pharmaceutically acceptable carrier, all percentages being based on the total weight of the composition.

The following examples illustrate the present invention.

EXAMPLES

Hereinafter, the term "THF" means tetrahydrofuran; "DCM" means dichloromethane; "MeOH" means methanol; "EtOH" means ethanol; "HPLC" means high-performance liquid chromatography; "sat." means saturated; "sol." means solution; "aq." means aqueous; "EtOAc" means ethyl acetate; "r.t." means room temperature; "r.m." means reaction mixture; "HOAc" means acetic acid; "Et$_3$N" means triethylamine; "RP" means reversed phase; "o.l." means organic layer; "min" means minute(s); "conc." means concentrated; "h" means hour(s); "q.s." means quantum sufficit; "I.D." means internal diameter; "Et$_2$O" means diethyl ether; "SFC" means Supercritical Fluid Chromatography; "DCE" means 1,2-dichloroethane; "DIPEA" means diisopropylethylamine; "eq." means equivalent; "DIPE" means diisopropyl ether; "DME" means 1,2-dimethoxyethane; "DMF" means N,N-dimethyl formamide; "Pd(PPh$_3$)$_4$" means tetrakis(triphenylphosphine)palladium; "Pd(OAc)$_2$" means palladium(II) acetate; "Grubbs second generation catalyst" means (1,3-dimesitylimidazolidin-2-ylidene)(tricyclohexylphosphine)

benzylidene ruthenium dichloride; "Pd$_2$(dba)$_3$" means tris (dibenzylideneacetone)dipalladium; "X-Phos" means dicyclohexyl[2',4',6'-tris(1-methylethyl)[1,1'-biphenyl]-2-yl]-phosphine; "Xantphos" means (9,9-dimethyl-9H-xanthene-4,5-diyl)bis[diphenylphosphine]; "Tebbes reagent" means μ-chlorobis(η5-2,4-cyclopentadien-1-yl)(dimethylaluminum)-μ-methylene-titanium; "Dess-Martin periodinane" means 1,1,1-tris(acetyloxy)-1,1-dihydro-1,2-benziodoxol-3(1H)-one; "rac" means racemic mixture; and "iPrOH" means 2-propanol.

The absolute stereochemical configuration for some of the compounds was determined using vibrational circular dichroism (VCD). A description on the use of VCD for the determination of absolute configuration can be found in Dyatkin A. B. et. al, *Chirality*, 14:215-219 (2002).

A. Preparation of the Intermediates

Example A 1 a) Preparation of Intermediate 1

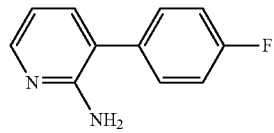

4-Fluorophenylboronic acid (1.21 g, 8.7 mmol) and Pd(PPh$_3$)$_4$ (0.42 g, 0.36 mmol) were added to a solution of 2-amino-3-bromopyridine (1.25 g, 7.20 mmol) in DMF (10 ml), water (4 ml) and K$_2$CO$_3$ (3.00 g, 21.70 mmol). The resulting mixture was stirred and heated at 160° C. for 30 min under microwave irradiation. The r.m. was cooled to r.t. and partitioned between water and DCM. The organic phase was separated, dried (MgSO$_4$), filtered and the solvent was evaporated in vacuo. The residue was purified by flash column chromatography over silica gel (eluent: DCM/MeOH from 100/0 to 98/2). The product fractions were collected and concentrated in vacuo, yielding 1.20 g of intermediate 1 (88%).

b) Preparation of Intermediate 2

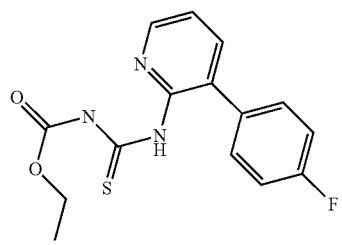 [SMILES: CCOC(=O)NC(=S)Nc1ncccc1-c1ccc(F)cc1]

Ethoxycarbonyl isothiocyanate (1.92 g, 15 mmol) was added dropwise at r.t. to a mixture of intermediate 1 (2.4 g, 13 mmol) in dioxane (125 ml). The r.m. was stirred at r.t. for 6 h. The solvents were then evaporated under reduced pressure. The resulting solid was triturated in DIPE, filtered and dried under vacuum, yielding 2.9 g of intermediate 2 (71%).

c) Preparation of Intermediate 3

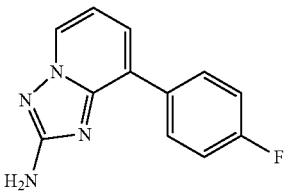 [SMILES: Nc1nc2c(-c3ccc(F)cc3)cccn2n1]

DIPEA (3.4 g, 26 mmol) was added dropwise at r.t. to a stirring mixture of hydroxylamine hydrochloride (3.05 g, 44 mmol) in MeOH (100 ml) and EtOH (10 ml). The r.m. was stirred at r.t. for 30 min. Subsequently, intermediate 2 (2.80 g, 8.8 mmol) was added portionwise and the r.m. was stirred at reflux for 16 h. The r.m. was cooled to r.t. and evaporated under reduced pressure. The residue was dissolved in DCM and the solution was washed with brine. The combined organic layers were dried (MgSO$_4$), filtered and concentrated in vacuo. The residue was purified by flash column chromatography over silica gel (eluent: DCM/MeOH from 100/0 to 98/2). The product fractions were collected and concentrated in vacuo, yielding 1.4 g of intermediate 3 (70%).

d) Preparation of Intermediate 4

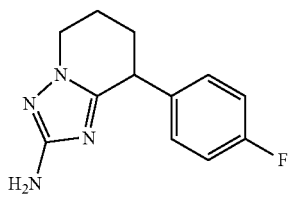 [SMILES: Nc1nc2n(n1)CCCC2c1ccc(F)cc1]

MeOH (100 ml) was added to Pt/C$_5$% (200 mg) under N$_2$ atmosphere. A mixture of intermediate 3 (1.20 g, 5.26 mmol) in HCl/iPrOH (6 N; q.s.) was added. The r.m. was stirred at 25° C. under H$_2$ atmosphere until 2 eq. of H$_2$ were absorbed. The catalyst was filtered off over diatomaceous earth and the filtrate was evaporated. The residue was suspended in DIPE, filtered and dried, yielding 1.1 g of intermediate 4 (78%).

e) Preparation of Intermediate 5

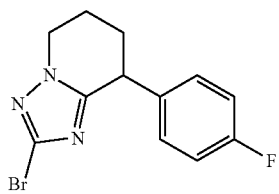 [SMILES: Fc1ccc(C2CCCn3nc(Br)nc32)cc1]

A solution of intermediate 4 (830 mg, 3.57 mmol) in HOAc (7.2 ml) was added to a mixture of NaNO$_2$ (277 mg, 4.13 mmol) in conc. H$_2$SO$_4$ (5.5 ml) at 10° C. The r.m. was stirred at r.t. for 30 min. Subsequently, the r.m. was added dropwise to a solution of CuBr (1.05 g, 7.34 mmol) in 48% HBr (7.2 ml). This mixture was stirred at r.t. for 1 h and was then carefully added to a stirred sat. aq. solution of NaHCO$_3$ and DCM. The organic phase was separated, dried (MgSO$_4$), filtered and the solvent was evaporated in vacuo. The combined organic layers were dried (MgSO$_4$), filtered and concentrated in vacuo. The residue was purified by flash column chromatography over silica gel (eluent: DCM/MeOH from 100/0 to 98/2). The product fractions were collected and concentrated in vacuo, yielding 570 mg of intermediate 5 (54%).

Example A2 a) Preparation of Intermediates 6, 7 and 8

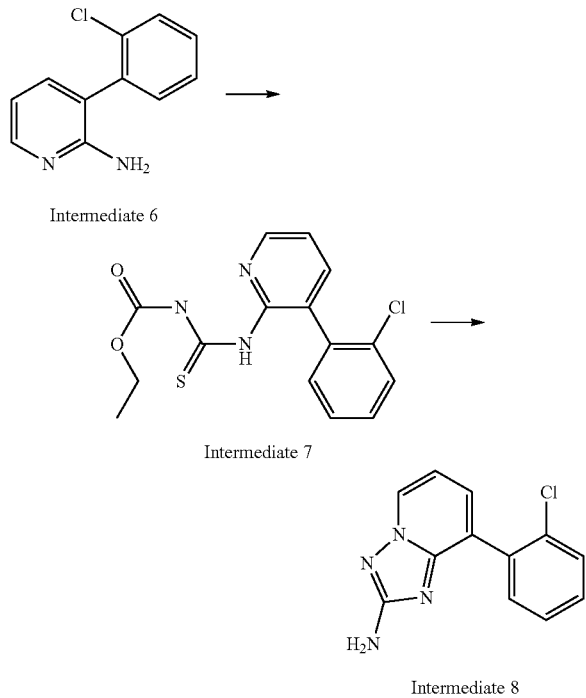

Intermediates 6, 7 and 8 were prepared by analogy to the reaction procedures described in Example A1.a, A1.b and A1.c.

b) Preparation of Intermediate 9

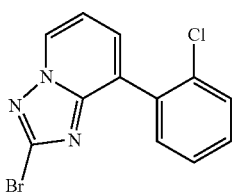 [SMILES: Clc1ccccc1-c1cccn2nc(Br)nc12]

A solution of intermediate 8 (1 g, 4.09 mmol) in HOAc (8 ml) was added to a mixture of NaNO$_2$ (315 mg, 5.57 mmol) in conc H$_2$SO$_4$ (6.7 ml) at 10° C. The r.m. was stirred at r.t. for 30 min and was then added dropwise to a solution of CuBr (1.17 g, 8.18 mmol) in 48% HBr (8 ml). The r.m. was stirred for 1 h at r.t. and was then carefully added to a stirred sat. aq. solution of NaHCO$_3$ in DCM. The combined organic layers were dried (MgSO$_4$), filtered and concentrated in vacuo. The residue was purified by flash column chromatography over silica gel (eluent: DCM/MeOH from 100/0 to 98/2). The product fractions were collected and concentrated in vacuo, yielding 0.6 g of intermediate 9 (48%).

Example A3 a) Preparation of Intermediate 10

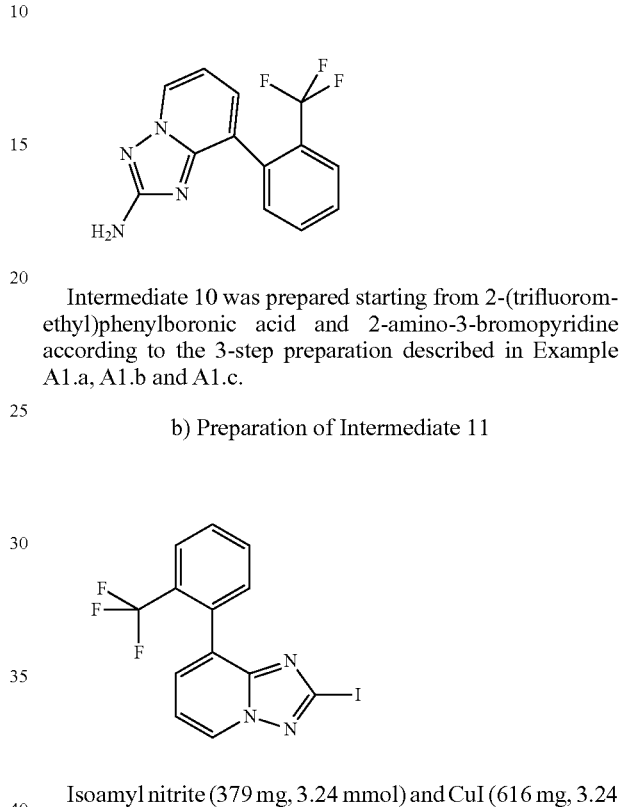

Intermediate 10 was prepared starting from 2-(trifluoromethyl)phenylboronic acid and 2-amino-3-bromopyridine according to the 3-step preparation described in Example A1.a, A1.b and A1.c.

b) Preparation of Intermediate 11

Isoamyl nitrite (379 mg, 3.24 mmol) and CuI (616 mg, 3.24 mmol) were added to a mixture of intermediate 10 (450 mg, 1.62 mmol) in CH$_3$CN (10 ml) at r.t. The r.m. was stirred at reflux for 1 h. The r.m. was cooled to r.t. and filtered over diatomaceous earth. The filtrate was evaporated and the residue was dissolved in DCM. This solution was washed with a 37% solution of NH$_4$OH. The combined organic layers were dried (MgSO$_4$), filtered and concentrated in vacuo. The residue was purified by flash column chromatography over silica gel (eluent: DCM/MeOH from 100/0 to 98/2). The product fractions were collected and concentrated in vacuo, yielding 0.36 g of intermediate 11 (57%).

Example A4 a) Preparation of Intermediate 12

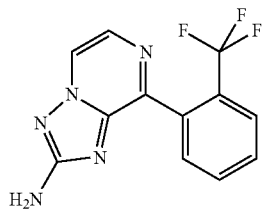 [SMILES: Nc1nc2c(-c3ccccc3C(F)(F)F)nccn2n1]

Intermediate 12 was prepared starting from 2-(trifluoromethyl)phenylboronic acid and 2-amino-3-chloropyrazine according to the 3-step preparation described in Example A1.a, A1.b and A1.c.

Example A5 a) Preparation of Intermediate 13

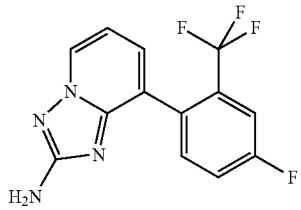 [SMILES: Nc1nc2c(-c3ccc(F)cc3C(F)(F)F)cccn2n1]

Intermediate 13 was prepared starting from 4-fluoro-2-(trifluoromethyl)phenylboronic acid and 2-amino-3-bromopyridine according to the 3-step preparation described in Example A1.a, A1.b and A1.c.

b) Preparation of Intermediate 14

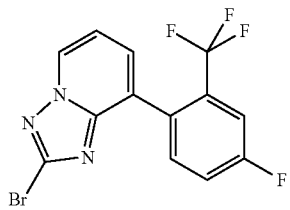 [SMILES: Fc1ccc(-c2cccn3nc(Br)nc23)c(C(F)(F)F)c1]

A solution of intermediate 13 (498 mg, 1.68 mmol) in HOAc (3.3 ml) was added to a mixture of NaNO$_2$ (130 mg, 1.88 mmol) in conc. H$_2$SO$_4$ (2.8 ml) at 10° C. The r.m. was stirred at r.t. for 30 min and was then added dropwise to a solution of CuBr (500 mg, 3.49 mmol) in 48% HBr (3.3 ml). The r.m. was stirred at r.t. for 1 h and was then carefully added to a stirred mixture of a sat. aq. solution of NaHCO$_3$ and DCM. The combined organic layers were dried (MgSO$_4$), filtered and concentrated in vacuo. The residue was purified by flash column chromatography over silica gel (eluent: DCM/MeOH from 100/0 to 98/2). The product fractions were collected and concentrated, yielding 50 mg of intermediate 14 (8%).

Example A6 a) Preparation of Intermediate 15

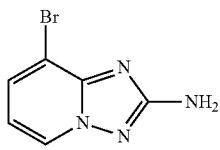

Intermediate 15 was prepared starting from 2-amino-3-bromopyridine according to the synthesis protocol described in Example A1.b and A1.c.

b) Preparation of Intermediate 16

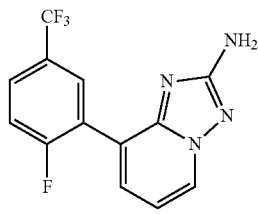 [SMILES: Nc1nc2c(-c3cc(C(F)(F)F)ccc3F)cccn2n1]

Intermediate 16 was prepared starting from intermediate 15 and 2-fluoro-5-(trifluoromethyl)phenylboronic acid according to the synthesis protocol described in Example A1.a.

c) Preparation of Intermediate 17

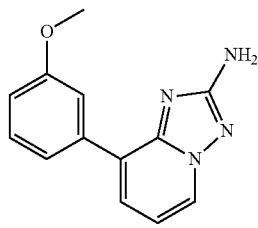 [SMILES: COc1cccc(-c2cccn3nc(N)nc23)c1]

Intermediate 17 was prepared starting from intermediate 15 and 3-methoxyphenylboronic acid according to the synthesis protocol described in Example A1.a.

d) Preparation of Intermediate 18

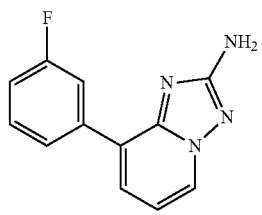 [SMILES: Nc1nc2c(-c3cccc(F)c3)cccn2n1]

Intermediate 18 was prepared starting from intermediate 15 and 3-fluoro-phenylboronic acid according to the synthesis protocol described in Example A1.a.

e) Preparation of Intermediate 19

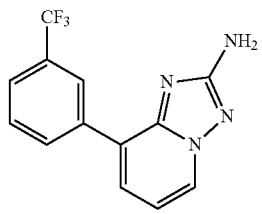 [SMILES: Nc1nc2c(-c3cccc(C(F)(F)F)c3)cccn2n1]

Intermediate 19 was prepared starting from intermediate 15 and 3-(trifluoromethyl)phenylboronic acid according to the synthesis protocol described in Example A1.a.

f) Preparation of Intermediate 20

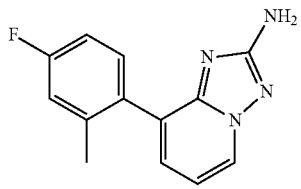 [SMILES: Cc1cc(F)ccc1-c1cccn2nc(N)nc12]

Intermediate 20 was prepared starting from intermediate 15 and 4-fluoro-2-methylphenylboronic acid according to the synthesis protocol described in Example A1.a.

g) Preparation of Intermediate 21

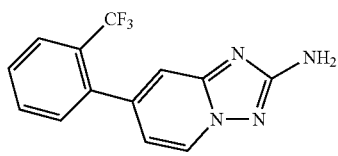 [SMILES: Nc1nc2cc(-c3ccccc3C(F)(F)F)ccn2n1]

Intermediate 21 was prepared starting from 2-amino-4-bromopyridine and 2-(trifluoromethyl)phenylboronic acid according to the two step preparation described in Example A6.a and A6.b.

Example A7 a) Preparation of Intermediate 22

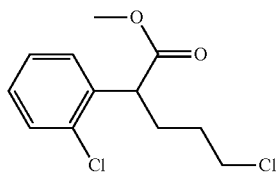 [SMILES: COC(=O)C(CCCCl)c1ccccc1Cl]

NaH (60% dispersion in mineral oil; 2.0 g, 49 mmol) was added to a solution of methyl-2-chlorophenylacetate (8.3 g, 45 mmol) in DMF (120 ml) at 0° C. The r.m. was stirred at 0° C. for 10 min and for 30 min at r.t. The r.m. was then cooled again to 0° C. and 1-chloro-3-iodopropane (5.1 ml, 48.1 mmol) was added dropwise under stirring. The r.m. was stirred at r.t. for 20 h. H$_2$O was then carefully added followed by Et$_2$O, and the layers were separated. The organic layer was washed with H$_2$O and brine, was dried (MgSO$_4$), and was then evaporated under reduced pressure to yield intermediate 22 (8.75 g, 75%) which was used as such in the next reaction step.

b) Preparation of Intermediate 23

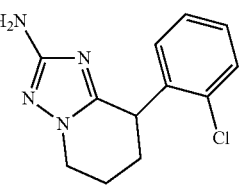

Aminoguanidine bicarbonate (15.4 g, 113 mmol) was added to a solution of intermediate 22 (7.4 g, 28.3 mmol) in 2-propanol (130 ml). The r.m. was heated in a sealed vessel for 48 h at 145° C. The r.m. was then cooled to r.t., the solid was filtered off and the filtrate was concentrated under reduced pressure. The residue was dissolved in DCM, washed with an aq. solution of NaHCO$_3$ and brine. The organic layer was dried (MgSO$_4$) and concentrated in vacuo. The residue was purified by flash column chromatography over silica gel (eluent: DCM/MeOH from 100/0 to 98/2). The product fractions were collected and concentrated in vacuo, yielding 1.5 g of intermediate 23 (21%).

Example A8 a) Preparation of Intermediate 24

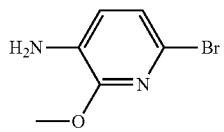

Sodium methoxide (176.2 g, 3.26 mol) was added in portions to a sol. of 3-amino-2,6-dibromopyridine (100 g, 939 mmol) in 1,4-dioxane (1 l) and the r.m. was stirred under reflux for 3 h. After cooling, the r.m. was poured onto a sat. aq. NH$_4$Cl aq. sol (1 l). Additional NH$_4$Cl (150 g) and H$_2$O (1 l) were added and the r.m. was stirred at r.t. for 30 min. Et$_2$O (2 l) was added and the r.m. was stirred for 30 min. The layers were separated and the aq. layer was diluted with H$_2$O (1.5 l) and further extracted with Et$_2$O (6×0.5 l). The combined o.l. were treated with brine (2×0.5 l), dried (MgSO$_4$) and conc. under reduced pressure to give a black residue. The residue was purified by flash chromatography over silicagel (glas filter, eluent DCM). The product fractions were combined and conc. under reduced pressure to afford an orange-brownish solid residue.

Yield: 67.2 g of intermediate 24 (78.3%).

b) Preparation of Intermediate 25

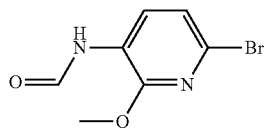

Acetic anhydride (110 ml, 1.16 mol) was added dropwise at r.t. to formic acid (170 ml) and this sol. was stirred at r.t. for 30 min. A sol. of intermediate 24 (67.2 g, 308 mmol) in THF (300 ml) was then added dropwise and the r.m. was stirred at 60° C. for 16 h. After cooling, the r.m. was poured onto ice/H$_2$O (1.5 l) and this resulting suspension was stirred for 30 min, and was then filtered off. Additional product was obtained by crystallization in the filtrate. Yield: 65 g of intermediate 25 (91.3%).

c) Preparation of Intermediate 26

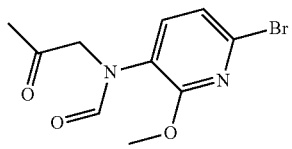 [SMILES: COc1nc(Br)ccc1N(C=O)CC(C)=O]

Chloroacetone (55.9 ml, 701 mmol) was added dropwise to a mechanically stirred suspension of intermediate 25 (65 g, 281 mmol), K$_2$CO$_3$ (135.6 g, 981 mmol), and KI (4.65 g, 28 mmol) in DMF (542 ml). The r.m. was stirred for 16 h at r.t. then poured onto ice/H$_2$O (2 l) and the resulting off white solid was collected by filtration and dried in vacuo at 60° C. Yield: 77.6 g of intermediate 26 (96.1%).

d) Preparation of Intermediate 27

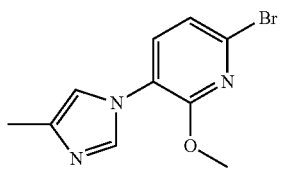

Intermediate 26 (77.6 g, 270 mmol) was added portion wise to a mechanically stirred sol. of NH$_4$OAc (105 g, 1.362 mol) in HOAc (500 ml). The r.m. was refluxed for 1 h, cooled and poured onto ice/H$_2$O (1 l), then diluted with toluene (1 l). This mixture was neutralized by addition of a 50% NaOH aq. sol. (590 ml). The layers were separated and the aq. layer was further extracted with toluene (4×0.3 l) and EtOAc (2×0.5 l). The combined o.l. were dried, filtered and conc. under reduced pressure. The residue was purified by column chromatography on silica gel (eluent: DCM/MeOH 99/1). The product fractions were collected and the solvent was removed under reduced pressure. The resulting white-brownish residue was triturated in DIPE to yield an off white solid which was filtered, washed with DIPE and dried under vacuum at 60° C. Yield: 40 g of intermediate 27 (55.2%).

Example A9

Preparation of Intermediate 28

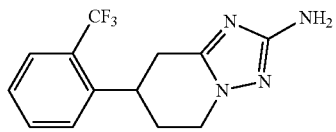 [SMILES: Nc1nc2n(n1)CCC(c1ccccc1C(F)(F)F)C2]

MeOH (100 ml) was added to Pd/C 10% (0.5 g) under N$_2$ atmosphere. Intermediate 21 (0.65 g, 2.34 mmol) and a HCl/iPrOH solution (6 N; 0.78 mL) were added. The r.m. was stirred at 50° C. under H$_2$ atmosphere until 2 eq. of H$_2$ were absorbed. The catalyst was filtered off over diatomaceous earth and the filtrate was evaporated. The residue was partitioned between DCM and an aq. NH$_4$OH solution. The combined o.l. were washed with brine, dried (MgSO$_4$) and conc. under reduced pressure, yielding 0.5 g of intermediate 28 (76%).

Example A 10 a) Preparation of Intermediate 29

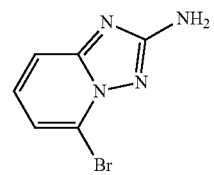 [SMILES: Nc1nc2cccc(Br)n2n1]

Intermediate 29 was prepared starting from 2-amino-6-bromopyridine according to the synthesis protocol described in Example A1.b and A1.c.

b) Preparation of Intermediate 30

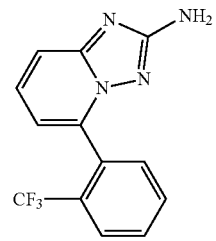 [SMILES: Nc1nc2cccc(-c3ccccc3C(F)(F)F)n2n1]

Intermediate 30 was prepared starting from intermediate 29 and 2-(trifluoromethyl)-phenylboronic acid according to the synthesis protocol described in Example A1.a.

c) Preparation of Intermediate 31

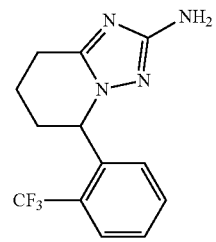 [SMILES: Nc1nc2n(n1)C(c1ccccc1C(F)(F)F)CCC2]

MeOH (100 ml) was added to Pd/C 10% (1 g) under N$_2$ atmosphere. Intermediate 30 (2.11 g, 7.58 mmol) and a HCl/iPrOH solution (6 N; 1.27 mL) were added. The r.m. was stirred at 50° C. under H$_2$ atmosphere until 2 eq. of H$_2$ were absorbed. The catalyst was filtered off over diatomaceous earth and the filtrate was evaporated. The residue was crystallized from DIPE, and the resulting product dried in vacuo, yielding 2.05 g of intermediate 31 (96%).

Example A11 a) Preparation of Intermediate 37 and Intermediate 38

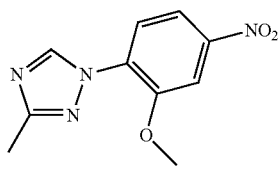

intermediate 37

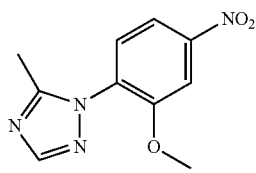

intermediate 38

A mixture of 1-fluoro-2-methoxy-4-nitrobenzene (821 mg, 4.80 mmol), 5-methyl-1H-1,2,4-triazole (800 mg, 9.63 mmol), $K_2CO_3$ (4.80 mmol) and DMSO (8 ml) was stirred at 120° C. for 1 h. After cooling, the r.m. was poured into ice water. The solid was filtered off, washed with water and dried in vacuo at 50° C. Yield: 0.55 g of intermediate 37 (49%). The aq. layer was saturated with NaCl, extracted with DCM and the organic layer was dried ($MgSO_4$), filtered and the solvent was evaporated. The residue was purified by column chromatography over silica gel (eluent: DCM). The desired fraction was collected and the solvent was evaporated. Yield: 0.15 g of intermediate 38 (13%).

b) Preparation of Intermediate 39

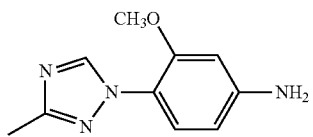

MeOH (50 ml) was added to Pd/C 10% (150 mg) under $N_2$ atmosphere. Subsequently, a 0.4% thiophene solution in DIPE (1 ml) and intermediate 37 (550 mg, 2.35 mmol) were added. The r.m. was stirred at 25° C. under $H_2$ atmosphere until 3 eq. of $H_2$ was absorbed. The catalyst was filtered off over diatomaceous earth. The filtrate was evaporated and the residue was suspended in DIPE, filtered off and dried in vacuo.

Yield: 0.35 g of intermediate 39 (73%).

Example A12 a) Preparation of Intermediate 40

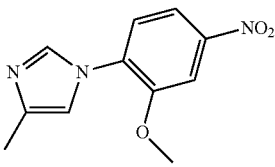 [SMILES: COc1cc([N+](=O)[O-])ccc1-n1cnc(C)c1]

2-Fluoro-5-nitroanisole (50 g, 0.29 mol) was added to a solution of 4-methyl-1H-imidazole (36.0 g, 0.44 mol) and $K_2CO_3$ (40.38 g, 0.29 mol) in DMSO (150 ml) in a stainless steel autoclave under a $N_2$ atmosphere. The vessel was closed and the r.m. was heated at 125° C. for 16 h. Subsequently, the mixture was cooled and the solvent was evaporated under reduced pressure. $H_2O$ (q.s.) was added to the residue and the precipitated product was collected by filtration. This solid was then triturated with DIPE and collected by filtration to yield a light-brown solid. Yield: 53.8 g of intermediate 40 (79%).

b) Preparation of Intermediate 41

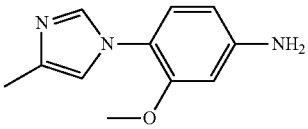

Intermediate 40 (215 g, 0.92 mol) was added to a stirring mixture of 10% Pd/C (10 g) in a 4% thiophene solution in MeOH (700 ml). The r.m. was heated at 50° C. under a $H_2$ atmosphere. After 3 eq. of $H_2$ were absorbed, the catalyst was removed by filtration over diatomaceous earth. The filtrate was evaporated under reduced pressure and the crude product was purified by column chromatography on silica gel (eluent: MeOH/DCM 10/90). The product fractions were combined and evaporated to yield a light-brown solid. Yield: 180 g of intermediate 41 (96%).

c) Preparation of Intermediate 42

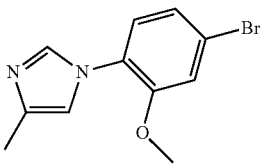

A stirred solution of $NaNO_2$ (7.47 g, 108 mmol) in conc. $H_2SO_4$ (160 ml) was cooled to 10° C. A solution of intermediate 41 (20.0 g, 98.4 mmol) in HOAc (200 ml) was added at such a rate that the temperature of the r.m. was maintained below 10° C. After addition was complete, the mixture was stirred at r.t. for 30 min. This solution was added dropwise, to a stirring solution of CuBr (28.2 g, 197 mmol) in 48% HBr (200 ml) at r.t. This mixture was stirred for 1 h and was then diluted with ice water (1 l). The resulting white precipitate was collected by filtration and washed with H$_2$O, yielding a solid (a) and the mother liquor (b).

The solid (a) was suspended in a mixture of DCM and a sat. aq. Na$_2$CO$_3$ solution. The resulting slurry was filtered over diatomaceous earth. The organic layer of the filtrate was washed with a diluted NH$_4$OH solution until the disappearance of blue colour. The organic phase was dried (MgSO$_4$), filtered and evaporated to yield a brown solid. The mother liquor (b) was basified with solid Na$_2$CO$_3$ and was then extracted with DCM. The combined organic extracts were washed with a diluted NH$_4$OH solution until the disappearance of blue colour. The organic phase was dried (MgSO$_4$), filtered and evaporated to give a brown solid.

The 2 brown solids were combined, yielding 24.0 g of intermediate 42 (91%).

d) Preparation of Intermediate 65

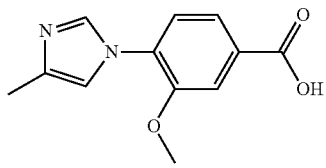 [SMILES: COc1cc(C(=O)O)ccc1-n1cnc(C)c1]

To a solution of intermediate 42 (24.0 g, 89.8 mmol), in THF/H$_2$O (300 ml/3 ml) in a stainless steel autoclave was added Pd(OAc)$_2$ (403 mg, 1.80 mmol) and 1,3-bis(diphenylphosphino)propane (1.48 g, 3.59 mmol) under a N$_2$ atmosphere. The vessel was closed and pressurized to 20 bar CO (gas), and heated at 150° C. for 24 h. The cooled reaction mixture was evaporated under reduced pressure, and was then acidified with a 30% aq. HOAc solution. Et$_2$O was added and the resulting mixture was evaporated until crystallization occurred. The light-brown crystals were collected by filtration. Yield: 18.1 g of intermediate 65 (87%).

e) Preparation of Intermediate 43

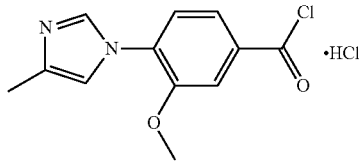 [SMILES: COc1cc(C(=O)Cl)ccc1-n1cnc(C)c1 ; Cl]

A mixture of intermediate 65 (3.24 g, 13.95 mmol), oxalyl chloride (1.68 g, 13 mmol) and DMF (5 ml) in DCM (300 ml) was stirred and heated at reflux for 1 h. The r.m. was then concentrated, and co-evaporated with toluene. The residue was used as such in the next reaction step. Yield: 3.5 g (quantitative) of intermediate 43.

Example A13 a) Preparation of Intermediate 44

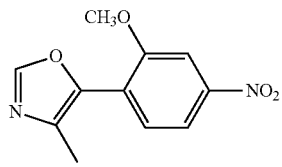

K$_2$CO$_3$ (9.6 g, 69.5 mmol) and 1-methyl-1-tosylmethylisocyanide (8 g, 38.2 mmol) were added to a solution of 2-formyl-5-nitroanisole (6.29 g, 34.7 mmol) in MeOH (150 ml) and the r.m. was refluxed for 4 h. The r.m. was concentrated under reduced pressure, the residue was dissolved in DCM and the organic phase was washed with H$_2$O, dried (MgSO$_4$), filtered and the solvent was evaporated in vacuo. The residue was purified by flash chromatography over silica gel (eluent: n-heptane/EtOAc from 100/0 to 50/50). The product fractions were collected and the solvent was evaporated. Yield: 6.24 g of intermediate 44 (77%).

b) Preparation of Intermediate 45

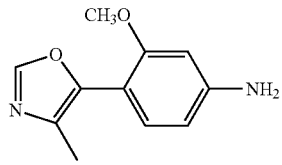

MeOH (150 ml) was added to Pd/C 10% (1 g) under a N$_2$ atmosphere. Subsequently, a 0.4% thiophene solution in DIPE (1 ml) and intermediate 44 (6.24 g, 26.6 mmol) were added. The r.m. was stirred at 25° C. under a H$_2$ atmosphere until 3 eq of H$_2$ was absorbed. The catalyst was filtered off over diatomaceous earth and the filtrate was evaporated. Yield: 5.4 g of intermediate 45 (99%).

Example A14 a) Preparation of Intermediate 46

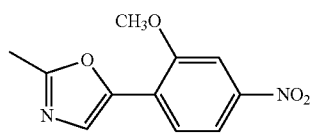

Iodobenzene diacetate (5.49 g, 18.44 mmoll) and trifluoromethanesulfonic acid (6.08 ml, 69.17 mmol) were stirred in CH$_3$CN (100 ml) at r.t. for 1 h under N$_2$. 2'-methoxy-4'-nitroacetophenone (3.0 g, 15.37 mmol) was added all at once at r.t. to the solution, and the r.m. was then refluxed for 2 h, then cooled to r.t. and carefully added to a stirred saturated aqueous solution of Na$_2$CO$_3$ (500 ml). The product was extracted with DCM and the organic phase was dried (MgSO$_4$), filtered and the solvent was evaporated under reduced pressure. The resulting dark brown oil was purified by flash column chromatography over silica gel (eluent: DCM/MeOH 95/5). The product fractions were collected and the solvent was evaporated under reduced pressure. Yield: 3.0 g of intermediate 46 (75%).

b) Preparation of Intermediate 47

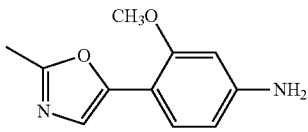

MeOH (50 ml) was added to Pd/C 10% (0.250 g) under a $N_2$ atmosphere. Subsequently, a 0.4% thiophene solution in DIPE (2 ml) and intermediate 46 (0.946 g, 4.04 mmol) were added. The r.m. was stirred at 25° C. under a $H_2$ atmosphere until 3 eq of $H_2$ was absorbed. The catalyst was filtered off over diatomaceous earth and the filtrate was evaporated. The product was triturated in DIPE, filtered off and dried under vacuum. Yield: 0.66 g of intermediate 47 (80%).

Example A15 a) Preparation of Intermediate 48

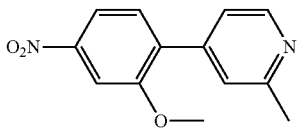 [SMILES: COc1cc([N+](=O)[O-])ccc1-c1ccnc(C)c1]

2-Methylpyridine-4-boronic acid pinacol ester (3.18 g, 14.5 mmol) and $Pd(PPh_3)_4$ (1.22 g, 1.06 mmol) were added to a solution of 2-bromo-5-nitroanisole (3.06 g, 13.2 mmol) and $Cs_2CO_3$ (1.33 g, 40.9 mmol) in DME (40 ml) and $H_2O$ (16 ml). The r.m. was stirred and heated at reflux for 16 h. The r.m. was cooled to r.t. and partitioned between $H_2O$ and DCM. The organic phase was separated, dried ($MgSO_4$), filtered and the solvent was evaporated. The combined organic layers were dried ($MgSO_4$), filtered and concentrated in vacuo. The residue was purified by flash column chromatography over silica gel (eluent: DCM/MeOH from 100/0 to 98/2). The product fractions were collected and concentrated in vacuo, yielding 2.04 g of intermediate 48 (63%).

b) Preparation of Intermediate 49

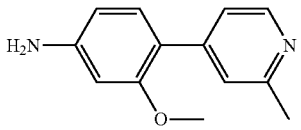

Intermediate 48 (2.04 g, 9.50 mmol) was added to a stirring mixture of 10% Pd/C (500 mg) and a 4% thiophene solution in MeOH (1 ml). The r.m. was heated at 50° C. under a $H_2$ atmosphere. After 3 eq. of $H_2$ were absorbed, the catalyst was removed by filtration over diatomaceous earth. The filtrate was evaporated under reduced pressure and the crude product was purified by column chromatography on silica gel (eluent: MeOH/DCM 10/90). The product fractions were combined and evaporated to yield a light-brown solid. Yield: 1.70 g of intermediate 49 (95%).

Example A16 a) Preparation of Intermediate 50

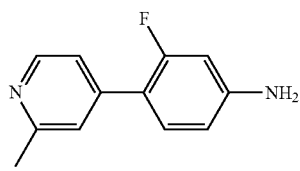

2-Methylpyridine-4-boronic acid pinacol ester (5.54 g, 25 mmol) and $Pd(PPh_3)_4$ (1.95 g, 1.68 mmol) were added to a solution of 4-bromo-3-fluoroaniline (4.0 g, 21 mmol) and $Cs_2CO_3$ (21.3 g, 65.3 mmol) in DME (40 ml) and $H_2O$ (25 ml). The resulting mixture was stirred and heated at 95° C. for 16 hours. The r.m. was cooled to r.t. and partitioned between water and DCM. The combined organic layers were dried ($MgSO_4$), filtered and concentrated in vacuo. The residue was purified by flash column chromatography over silica gel (eluent: DCM/MeOH from 100/0 to 98/2). The product fractions were collected and concentrated in vacuo, yielding 4.1 g of intermediate 50 (96%).

Example A17 b) Preparation of Intermediate 51

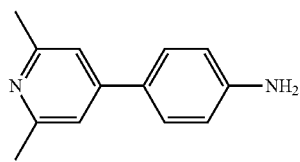

2,6-Dimethylpyridine-4-boronic acid pinacol ester (5.96 g, 26 mmol) and $Pd(PPh_3)_4$ (2150 mg, 1.86 mmol) were added to a solution of 4-bromoaniline (4 g, 23 mmol) and $Cs_2CO_3$ (21.3 g, 65.3 mmol) in DME (40 ml) and $H_2O$ (25 ml). The resulting mixture was stirred and heated at 95° C. for 16 h. The r.m. was cooled to r.t. and partitioned between $H_2O$ and DCM. The combined organic layers were dried ($MgSO_4$), filtered and concentrated in vacuo. The residue was purified by flash column chromatography over silica gel (eluent: DCM/MeOH from 100/0 to 98/2). The product fractions were collected and concentrated in vacuo, yielding 2.50 g of intermediate 51 (54%).

Example A18 a) Preparation of Intermediate 52

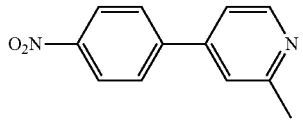 [SMILES: Cc1cc(-c2ccc([N+](=O)[O-])cc2)ccn1]

2-Methylpyridine-4-boronic acid pinacol ester (5 g, 22.8 mmol) and Pd(PPh$_3$)$_4$ (1.92 g, 1.66 mmol) were added to a solution of 1-iodo-4-nitrobenzene (5.17 g, 20.7 mmol) and Cs$_2$CO$_3$ (21 g, 64.3 mmol) in DME (40 ml) and water (25 ml). The resulting mixture was stirred and heated at reflux for 16 h. The r.m. was cooled to r.t. and partitioned between water and DCM. The organic phase was separated, dried (MgSO$_4$), filtered and the solvent was evaporated in vacuo. The combined organic layers were dried (MgSO$_4$), filtered and concentrated in vacuo. The residue was purified by flash column chromatography over silica gel (eluent: DCM/MeOH from 100/0 to 98/2). The product fractions were collected and concentrated in vacuo, yielding 3.1 g of intermediate 52 (70%).

b) Preparation of Intermediate 53

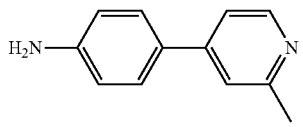

Intermediate 52 (2.0 g, 9.34 mmol) was added to a stirred mixture of 10% Pd/C (1 g) and a 4% thiophene solution in MeOH (2 ml). The r.m. was heated at 25° C. under a H$_2$ atmosphere. After 3 eq. of H$_2$ were absorbed, the catalyst was removed by filtration over diatomaceous earth. The filtrate was evaporated under reduced pressure and the crude product was used as such in the next step. Yield: 1.5 g of intermediate 53 (87%).

Example A19 a) Preparation of Intermediate 54

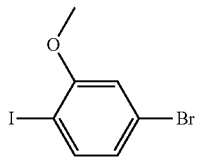

A stirred solution of NaNO$_2$ (5.63 g, 81.7 mmol) in conc. HCl (6.2 ml) was cooled to 10° C. 4-bromo-2-methoxy-phenylamine (15 g, 74 mmol) in HOAc (100 ml) was added at such a rate that the temperature of the r.m. was maintained below 10° C. After addition was completed, the mixture was stirred at r.t. for 30 min. This solution was added dropwise, to a stirring solution of KI (37 g, 223 mmol) in 48% HBr (200 ml) at r.t. This mixture was stirred for 1 h and was then diluted with ice water (1000 ml). The resulting white precipitate was collected by filtration and washed with H$_2$O, yielding a solid (a) and the mother liquor (b).

The solid (a) was suspended in a mixture of DCM and a sat. aq. Na$_2$CO$_3$ solution. The resulting slurry was filtered over diatomaceous earth. The organic layer of the filtrate was washed with a diluted NH$_4$OH solution until the disappearance of blue colour. The organic phase was dried (MgSO$_4$), filtered and evaporated to yield a brown solid.

The mother liquor (b) was basified by the addition of solid Na$_2$CO$_3$ and was then extracted with DCM. The combined organic extracts were washed with a diluted NH$_4$OH solution until the disappearance of blue colour. The organic phase was dried (MgSO$_4$), filtered and evaporated to give a brown solid.

The 2 brown solids were combined, yielding 24.0 g of intermediate 54 (91%).

b) Preparation of Intermediate 55

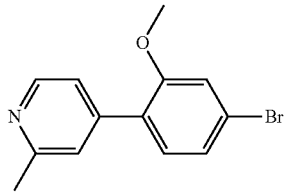 [SMILES: COc1cc(Br)ccc1-c1ccnc(C)c1]

2-Methylpyridine-4-boronic acid pinacol ester (5.49 g, 25.1 mmol) and Pd(PPh$_3$)$_4$ (3.62 g, 3.1 mmol) was added to a solution of intermediate 54 (9.8 g, 31.3 mmol) in dioxane (200 ml), H$_2$O (50 ml) and K$_2$CO$_3$ (13 g, 94 mmol). The resulting mixture was stirred and heated at 100° C. for 18 h. The r.m. was cooled to r.t. and partitioned between H$_2$O and DCM. The combined organic layers were dried (MgSO$_4$), filtered and concentrated in vacuo. The residue was purified by flash column chromatography over silica gel (eluent: DCM/MeOH from 100/0 to 98/4). The product fractions were collected and concentrated in vacuo, yielding 4.5 g of intermediate 55 (52%).

Example A20 a) Preparation of Intermediate 56

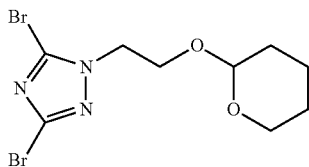 [SMILES: Brc1nc(Br)n(CCOC2CCCCO2)n1]

To a solution of 3,5-dibromo-1H-1,2,4-triazole (5.00 g, 22.04 mmol) in CH$_3$CN (50 ml) was added 2-(2-bromoethoxy)tetrahydro-2H-pyran (5.07 g, 24.24 mmol) and DIPEA (4.00 ml, 24.24 mmol). The resulting solution was heated at 90° C. for 3 h. Subsequently, the mixture was cooled and diluted with EtOAc (100 ml). The resulting solution was then washed with a sat. aq. solution of NaHCO$_3$ and brine. The organic layer was dried (MgSO$_4$) and concentrated under reduced pressure. The residue was purified by flash column chromatography over silica gel (eluent: DCM/MeOH(NH$_3$) from 100/0 to 97/3). The product fractions were collected and concentrated in vacuo, yielding 6.00 g of intermediate 56 (77%).

b) Preparation of Intermediate 57

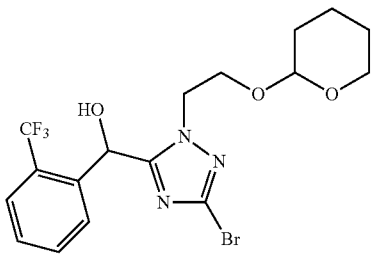 [SMILES: OC(c1ccccc1C(F)(F)F)c1nc(Br)nn1CCOC1CCCCO1]

To a solution of intermediate 56 (4.30 g, 12.1 mmol) in THF (215 mL) at −78° C. was added n-butyl lithium (4.85 ml, 12.1 mmol, 2.5 M in hexanes). The resulting solution was stirred for 20 min. at −78° C. after which a solution of 2-(trifluoromethyl)benzaldehyde (2.10 g, 12.1 mmol) in THF (43 ml) was added. The solution was then stirred at −78° C. for 20 min. and quenched by the addition of a sat. aq. solution of NH$_4$Cl (5 ml). The reaction was then allowed to warm to r.t., diluted with EtOAc (200 ml) and washed with H$_2$O (2×100 ml). The organic layer was dried (MgSO$_4$), filtered and concentrated under reduced pressure. The residue was purified by flash column chromatography over silica gel (eluent: DCM/MeOH(NH$_3$) from 100/0 to 99/1). The product fractions were collected and concentrated in vacuo, yielding 5.00 g of intermediate 57 (92%).

c) Preparation of Intermediate 58

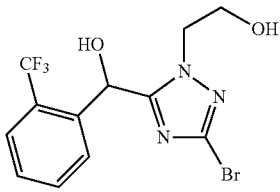 [SMILES: OCCn1nc(Br)nc1C(O)c1ccccc1C(F)(F)F]

To a solution of intermediate 57 (3.00 g, 6.63 mmol) in methanol (300 mL) at room temperature was added p-toluenesulfonic acid (230 mg, 1.33 mmol). The resulting solution was stirred for 2 h. The r.m. was then concentrated in vacuo and the residue dissolved in DCM (100 ml), washed with a sat. aq. solution of NaHCO$_3$, dried (MgSO4) and concentrated under reduced pressure. The residue was purified by flash column chromatography over silica gel (eluent: DCM/MeOH(NH$_3$) from 100/0 to 97/3). The product fractions were collected and concentrated in vacuo, yielding 2.3 g of intermediate 58 (94%).

d) Preparation of Intermediate 59

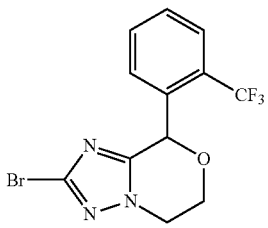 [SMILES: FC(F)(F)c1ccccc1C1OCCn2nc(Br)nc21]

To a solution of intermediate 58 (750 mg, 2.04 mmol) in toluene (100 ml) was added p-toluenesulfonic acid (389.00 mg, 2.04 mmol). The resulting solution was then refluxed using a Dean-Stark apparatus for 25 h. The solution was then washed with an aq. solution of 1 M NaOH and brine, dried (MgSO4), and concentrated under reduced pressure. The residue was purified by flash column chromatography over silica gel (eluent: DCM/MeOH(NH$_3$) from 100/0 to 90/10). The product fractions were collected and concentrated in vacuo, yielding 350 mg of intermediate 59 (49%).

Example A21

Alternative Method for the Preparation of Intermediate 5 a) Preparation of Intermediate 60

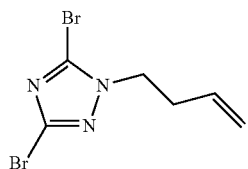

To a solution of 3,5-dibromo-1H-1,2,4-triazole (5.00 g, 22 mmol) in CH$_3$CN (50 ml) was added 4-bromo-1-butene (3.27 g, 24 mmol) and DIPEA (4.00 ml, 24 mmol), the resulting solution was then heated at 90° C. for 3 h. The r.m. was then cooled and diluted with EtOAc (100 ml), washed with an aq. sat. solution of NaHCO$_3$ followed by brine, dried (MgSO$_4$), filtered and concentrated under reduced pressure. The residue was purified by flash column chromatography over silica gel (eluent: Heptane/DCM from 100/0 to 0/100). The product fractions were collected and concentrated in vacuo, yielding 5.55 g of intermediate 60 (89%).

b) Preparation of Intermediate 61

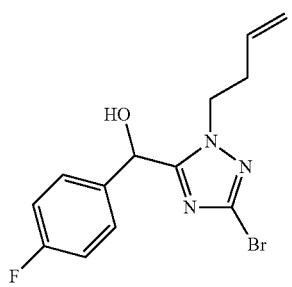 [SMILES: C=CCCn1nc(Br)nc1C(O)c1ccc(F)cc1]

To a solution of intermediate 60 (4.50 g, 16 mmol) in THF (285 ml) at −78° C. was added n-butyl lithium (6.41 ml, 16 mmol, 2.5 M in hexanes). The r.m. was stirred for 20 min. at −78° C. Subsequently, 4-fluorobenzaldehyde (1.99 g, 16 mmol) in THF (56 ml) was added, and the solution was then stirred at −78° C. for 20 min. The r.m. was quenched by the addition of an aq. sat. solution of NH$_4$Cl (5 ml). The reaction was allowed to warm to r.t. and was then diluted by the addition of EtOAc (200 ml), washed with H$_2$O (2×100 ml). The organic layer was dried (MgSO$_4$), filtered and concentrated under reduced pressure. The residue was purified by flash column chromatography over silica gel (eluent: DCM/MeOH(NH$_3$) from 100/0 to 97/3). The product fractions were collected and concentrated in vacuo, yielding 4.20 g of intermediate 61 (80%).

c) Preparation of Intermediate 62

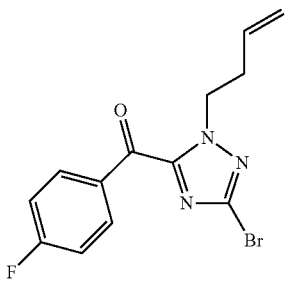

To a solution of intermediate 61 (2.00 g, 6.13 mmol) in DCM (200 ml) at 0° C. was added pyridine (0.74 ml, 9.20 mmol) and Dess-Martin periodinane (2.73 g, 6.44 mmol). The r.m. was stirred for 1 h at 0° C. The r.m. was then diluted with DCM (200 ml) and washed with a sat. aq. solution of NaHCO$_3$. The organic layer was dried (MgSO$_4$), and concentrated under reduced pressure. The residue was purified by flash column chromatography over silica gel (eluent: DCM/MeOH(NH$_3$) from 100/0 to 97/3). The product fractions were collected and concentrated in vacuo, yielding 1.65 g of intermediate 62 (83%).

d) Preparation of Intermediate 63

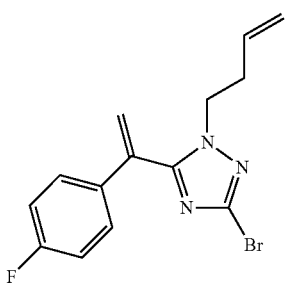 [SMILES: C=CCCn1nc(Br)nc1C(=C)c1ccc(F)cc1]

To a solution of intermediate 62 (1.00 g, 3.09 mmol) in THF (50 ml) at r.t. was added Tebbes reagent (6.17 ml, 3.085 mmol). The r.m. was then stirred for 18 h. The r.m. was diluted by the addition of Et$_2$O (400 ml) and quenched by the addition of an aq. solution of NaOH (30.8 ml, 0.5 M). The mixture was filtered through a pad of diatomaceous earth and concentrated under reduced pressure. The residue was purified by flash column chromatography over silica gel (eluent: DCM/MeOH (NH$_3$) from 100/0 to 97/3). The product fractions were collected and concentrated in vacuo, yielding 660 mg of intermediate 63 (66%).

e) Preparation of Intermediate 64

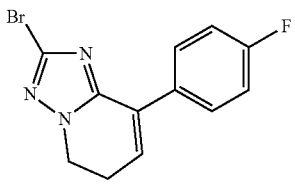 [SMILES: Fc1ccc(C2=CCCn3nc(Br)nc32)cc1]

To a solution of intermediate 63 (550 mg, 1.71 mmol) in DCE (55 ml) was added Grubbs second generation catalyst (145 mg, 0.17 mmol). The r.m. was then heated at 60° C. for 2 h and concentrated under reduced pressure. The residue was purified by flash column chromatography over silica gel (eluent: DCM/MeOH(NH$_3$) from 100/0 to 97/3). The product fractions were collected and concentrated in vacuo, yielding 350 mg of intermediate 64 (69%).

f) Preparation of Intermediate 5

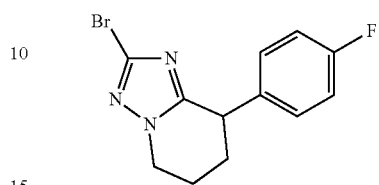

To a solution of intermediate 64 (250 mg, 0.85 mmol) in MeOH (55 ml) was added sodium borohydride (322 mg, 8.50 mmol). The r.m. was stirred at r.t. for 2 h. The r.m. was concentrated under reduced pressure. The residue was then dissolved in DCM and washed with an aq. solution of HCl (0.5 M), dried (MgSO$_4$), and concentrated under reduced pressure. The residue was purified by flash column chromatography over silica gel (eluent: DCM/MeOH(NH$_3$) from 100/0 to 97/3). The product fractions were collected and concentrated in vacuo, yielding 220 mg of intermediate 5 (87%).

B. Preparation of the Compounds

Example B1

Preparation of Compound 1

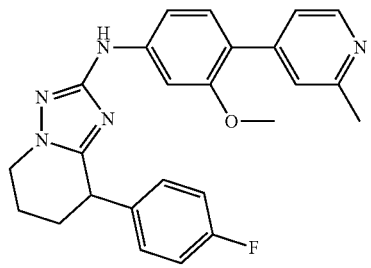 [SMILES: COc1cc(Nc2nc3n(n2)CCCC3c2ccc(F)cc2)ccc1-c1ccnc(C)c1]

Intermediate 49 (176 mg, 0.825 mmol), Pd$_2$(dba)$_3$ (75 mg, 0.0825 mmol), X-Phos (86 mg, 0.182 mmol) and Cs$_2$CO$_3$ (806 mg, 2.47 mmol) were added to a solution of intermediate 5 (280 mg, 0.908 mmol) in 2-methyl-2-propanol (5 ml) under a N$_2$ atmosphere. The r.m. was heated at 110° C. for 20 h. Then the r.m. was cooled to r.t., water was added and the mixture was extracted with DCM. The combined organic layers were dried (MgSO$_4$), filtered and concentrated in vacuo. The residue was purified by RP preparative HPLC [RP Vydac Denali C18-10 μm, 250 g, I.D. 5 cm); mobile phase: gradient of (0.25% NH$_4$HCO$_3$ solution in water)/MeOH+ CH$_3$CN]. The product fractions were collected and worked up. Yield: 115 mg of compound 1 (20%).

Example B2

Preparation of Compound 2

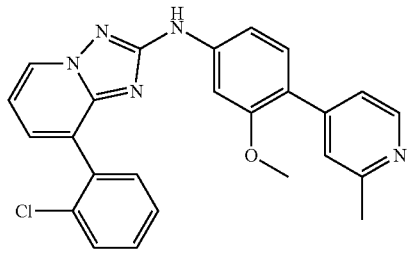 [SMILES: COc1cc(Nc2nc3c(-c4ccccc4Cl)cccn3n2)ccc1-c1ccnc(C)c1]

Intermediate 49 (200 mg, 0.933 mmol), Pd$_2$(dba)$_3$ (85 mg, 0.0933 mmol), X-Phos (98 mg, 0.205 mmol) and Cs$_2$CO$_3$ (912 mg, 2.8 mmol) were added to a solution of intermediate 9 (300 mg, 0.933 mmol) in 2-methyl-2-propanol (5 ml) under a N$_2$ atmosphere. The r.m. was heated at 110° C. for 20 h. Then, the r.m. was cooled to r.t., water was added and the mixture was extracted with DCM. The combined organic layers were dried (MgSO$_4$), filtered and concentrated in vacuo. The residue was purified by flash column chromatography over silica gel (eluent: DCM/MeOH(NH$_3$) from 100/0 to 98/2). The product fractions were collected and concentrated in vacuo, yielding 0.160 g of compound 2 (39%).

Example B3

Preparation of Compound 3

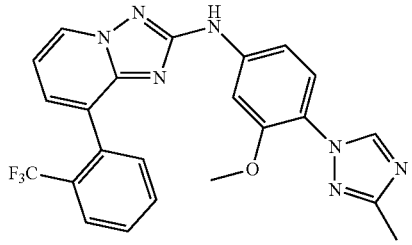 [SMILES: COc1cc(Nc2nc3c(-c4ccccc4C(F)(F)F)cccn3n2)ccc1-n1cnc(C)n1]

Intermediate 39 (360 mg, 0.925 mmol), Pd$_2$(dba)$_3$ (85 mg, 0.0925 mmol), X-Phos (88 mg, 0.185 mmol) and Cs$_2$CO$_3$ (904 mg, 2.78 mmol) were added to a solution of intermediate 11 (189 mg, 0.925 mmol) in 2-methyl-2-propanol (5 ml) under a N$_2$ atmosphere. The r.m. was heated at 110° C. for 20 h. Then, the r.m. was cooled to r.t., water was added and the mixture was extracted with DCM. The combined organic layers were dried (MgSO$_4$), filtered and concentrated in vacuo. The residue was purified by flash column chromatography over silica gel (eluent: DCM/MeOH(NH$_3$) from 100/0 to 98/2), yielding 0.175 g of compound 3 (41%).

Example B4

Preparation of Compound 4

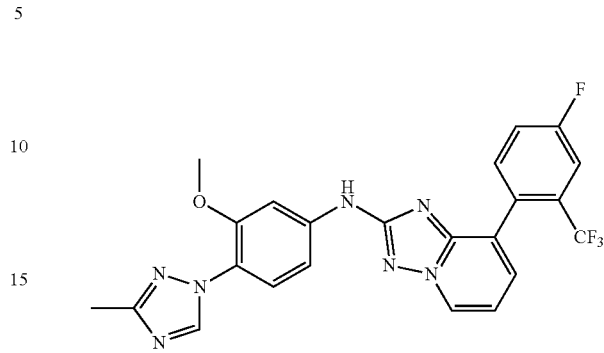

Intermediate 39 (50 mg, 0.139 mmol), Pd$_2$(dba)$_3$ (24 mg, 0.18 mmol), X-Phos (7 mg, 0.014 mmol) and Cs$_2$CO$_3$ (135 mg, 0.417 mmol) were added to a solution of intermediate 14 (28 mg, 0.139 mmol) in 2-methyl-2-propanol (5 ml) under a N$_2$ atmosphere. The r.m. was heated at 110° C. for 20 h. Then, the r.m. was cooled to r.t., water was added and the mixture was extracted with DCM. The combined organic layers were dried (MgSO$_4$), filtered and concentrated in vacuo. The residue was purified by RP preparative HPLC [RP Vydac Denali C18-10 µm, 250 g, I.D. 5 cm); mobile phase: a gradient of (0.25% NH$_4$HCO$_3$ solution in H$_2$O)/MeOH+CH$_3$CN]. The product fractions were collected and worked up. Yield: 10 mg of compound 4 (15%).

Example B5

Preparation of Compound 5

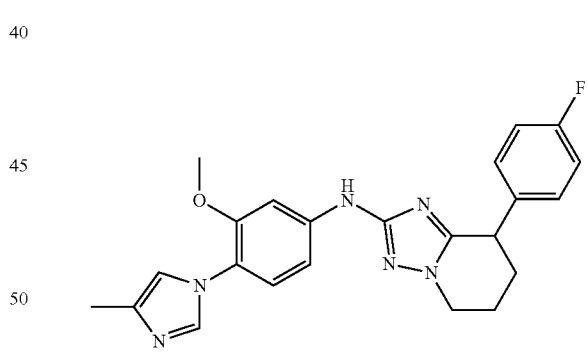

Intermediate 42 (120 mg, 0.52 mmol), Pd$_2$(dba)$_3$ (47 mg, 0.052 mmol), X-Phos (49 mg, 0.10 mmol) and Cs$_2$CO$_3$ (673 mg, 2.07 mmol) were added to a solution of intermediate 4 (157 mg, 0.52 mmol) in 2-methyl-2-propanol (5 ml) under a N$_2$ atmosphere. The r.m. was heated at 110° C. for 20 h. Then, the r.m. was cooled to r.t., water was added and the mixture was extracted with DCM. The combined organic layers were dried (MgSO$_4$), filtered and concentrated in vacuo. The residue was purified by flash column chromatography over silica gel (eluent: DCM/MeOH from 100/0 to 98/2). The product fractions were collected and concentrated in vacuo. The residue was triturated in DIPE, yielding 0.038 g of compound 5 (18%).

Example B6

Preparation of Compound 6

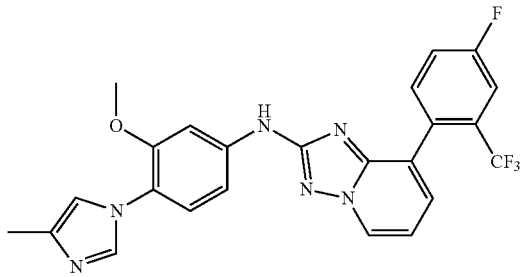 [SMILES: COc1cc(Nc2nc3c(-c4ccc(F)cc4C(F)(F)F)cccn3n2)ccc1-n1cnc(C)c1]

Intermediate 42 (100 mg, 0.34 mmol), Pd$_2$(dba)$_3$ (31 mg, 0.034 mmol), X-Phos (32 mg, 0.068 mmol) and Cs$_2$CO$_3$ (440 mg, 1.35 mmol) were added to a solution of intermediate 13 (102 mg, 0.34 mmol) in 2-methyl-2-propanol (5 ml) under a N$_2$ atmosphere. The r.m. was heated at 110° C. for 20 h. Then, the r.m. was cooled to r.t., water was added and the mixture was extracted with DCM. The combined organic layers were dried (MgSO$_4$), filtered and concentrated in vacuo. The residue was purified by flash column chromatography over silica gel (eluent: DCM/MeOH from 100/0 to 98/2). The product fractions were collected and concentrated in vacuo. The residue was triturated in DIPE, yielding 0.027 g of compound 6 (17%).

Example B7

Preparation of Compound 7

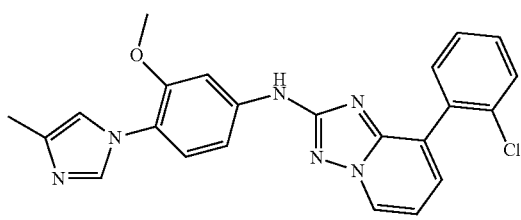 [SMILES: COc1cc(Nc2nc3c(-c4ccccc4Cl)cccn3n2)ccc1-n1cnc(C)c1]

Intermediate 42 (176 mg, 0.72 mmol), Pd$_2$(dba)$_3$ (66 mg, 0.072 mmol), X-Phos (69 mg, 0.14 mmol) and Cs$_2$CO$_3$ (937 mg, 2.88 mmol) were added to a solution of intermediate 8 (218 mg, 0.72 mmol) in 2-methyl-2-propanol (10 ml) under a N$_2$ atmosphere. The r.m. was heated at 110° C. for 20 h. Then, the r.m. was cooled to r.t., water was added and the mixture was extracted with DCM. The combined organic layers were dried (MgSO$_4$), filtered and concentrated in vacuo. The residue was purified by flash column chromatography over silica gel (eluent: DCM/MeOH from 100/0 to 98/2). The product fractions were collected and concentrated in vacuo. The residue was triturated in DIPE, yielding 0.140 g of compound 7 (45%).

Example B8 a) Preparation of Compound 8

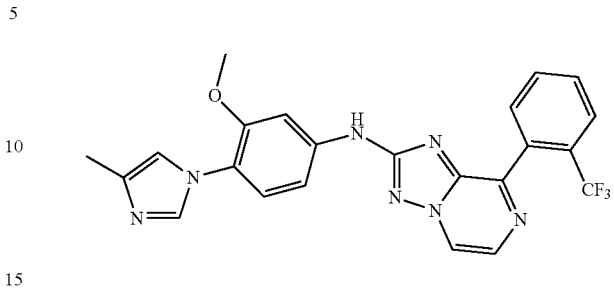

Intermediate 42 (502 mg, 1.8 mmol), Pd$_2$(dba)$_3$ (165 mg, 0.18 mmol), X-Phos (172 mg, 0.36 mmol) and Cs$_2$CO$_3$ (2.35 g, 7.2 mmol) were added to a solution of intermediate 12 (546 mg, 1.8 mmol) in 2-methyl-2-propanol (20 ml) under a N$_2$ atmosphere. The r.m. was heated at 110° C. for 20 h and was then cooled to r.t. H$_2$O was added and the mixture was extracted with DCM. The organic layers were dried (MgSO$_4$), filtered and concentrated in vacuo. The residue was purified by flash column chromatography over silica gel (eluent: DCM/MeOH from 100/0 to 98/2). The product fractions were collected and concentrated in vacuo, yielding 403 mg of compound 8 (48%).

b) Preparation of Compound 9

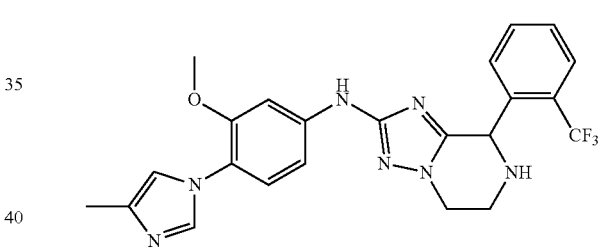

MeOH (40 ml) was added to Pt/C$_5$% (50 mg) under a N$_2$ atmosphere. Subsequently, compound 8 (350 mg, 0.75 mmol) in a mixture HCl/isopropanol (6 N) (0.376 ml, 2.26 mmol) was added. The r.m. was stirred at 25° C. under H$_2$ atmosphere until 2 eq. of H$_2$ was absorbed. The catalyst was filtered off over diatomaceous earth and the filtrate was evaporated. The residue was suspended in DIPE, filtered and dried, yielding 200 mg of compound 9 (57%).

c) Preparation of Compound 13

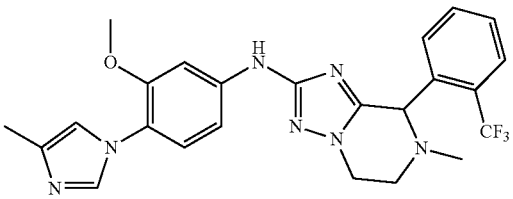 [SMILES: COc1cc(Nc2nc3n(n2)CCN(C)C3c2ccccc2C(F)(F)F)ccc1-n1cnc(C)c1]

Compound 9 (75 mg, 0.16 mmol) and formaldehyde (37% w/w aq. solution; 155 mg, 0.19 mmol) were dissolved in MeOH (2 ml). The r.m. was stirred at r.t. for 45 min. Subsequently, 1 drop of acetic acid was added to the r.m. followed by sodium cyanoborohydride (15 mg, 0.224 mmol). The r.m. was stirred at r.t. for 20 h. 1 Drop of water was added and the r.m. was then evaporated under reduced pressure. The residue was partitioned between DCM/H₂O. The organic layer was separated, dried (MgSO₄), filtered and evaporated under reduced pressure. The residue was precipitated from a mixture of DIPE and CH₃CN. The resulting solid was filtered and dried under vacuum to yield 51 mg of compound 13 (66%).

d) Preparation of Compound 14

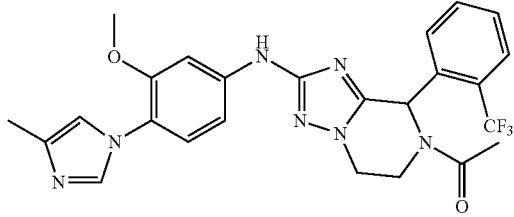 [SMILES: COc1cc(Nc2nc3n(n2)CCN(C(C)=O)C3c2ccccc2C(F)(F)F)ccc1-n1cnc(C)c1]

Acetyl chloride (25 mg, 0.32 mmol) was added to a mixture of compound 9 (75 mg, 0.16 mmol) and Et₃N (0.066 ml, 0.48 mmol) in DCM (3 ml) at r.t. The r.m. was then stirred at r.t. for 20 h. A 37% NH₄OH solution (1 ml) was then added to the r.m. The r.m. was partitioned between DCM and H₂O. The organics were separated, dried (MgSO₄) and evaporated under reduced pressure. The residue was purified by flash column chromatography over silica gel (eluent: DCM/MeOH from 100/0 to 99/1). The product fractions were collected and concentrated in vacuo, yielding 35 mg of compound 14 (43%).

Example B9

Preparation of Compound 36

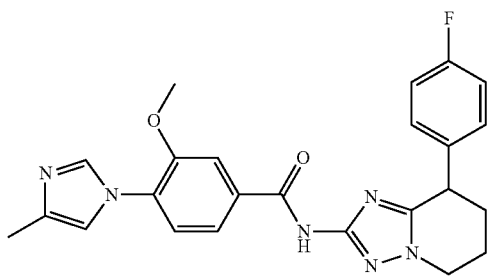 [SMILES: COc1cc(C(=O)Nc2nc3n(n2)CCCC3c2ccc(F)cc2)ccc1-n1cnc(C)c1]

To a mixture of intermediate 4 (60 mg, 0.26 mmol) in pyridine (0.06 ml, 0.78 mmol) and DCM (5 ml) was added intermediate 43 (87 mg, 0.35 mmol) dropwise at 0° C. The r.m. was stirred at r.t. for 1 h. The r.m. was washed with an aq. NaOH sol. (1 M). The organics were dried (MgSO₄), filtered and evaporated under reduced pressure. The residue was purified by flash column chromatography over silica gel (eluent: DCM/MeOH(NH₃) from 100/0 to 98/1). The product fractions were collected and concentrated in vacuo, yielding 15 mg of compound 36 (13%).

Example B10

Preparation of Compound 72

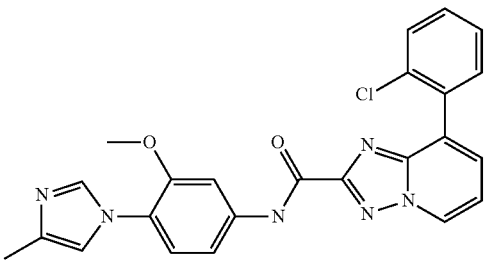 [SMILES: COc1cc(NC(=O)c2nc3c(-c4ccccc4Cl)cccn3n2)ccc1-n1cnc(C)c1]

A mixture of intermediate 9 (127 mg, 41 mmol), intermediate 41 (99 mg, 0.41 mmol), (Pd(OAc)₂ (2 mg, 0.01 mmol), XantPhos (5 mg, 0.01 mmol) and Et₃N (125 mg, 1.20 mmol) in toluene (40 ml) under a nitrogen atmosphere was pressurized to 20 bar CO in an autoclave, and the mixture was reacted for 18 h at 110° C. The r.m. was cooled to r.t. and concentrated under reduced pressure. The residue was dissolved in DCM, washed with water, dried (MgSO₄), filtered and evaporated under reduced pressure. The residue was purified by RP preparative HPLC [RP Vydac Denali C18—10 μm, 250 g, I.D. 5 cm); mobile phase: a gradient of (0.25% NH₄HCO₃ solution in H₂O)/MeOH]. The product fractions were collected and worked up. Yield 9 mg of compound 72 (5%).

Example B11

Preparation of Compound 65

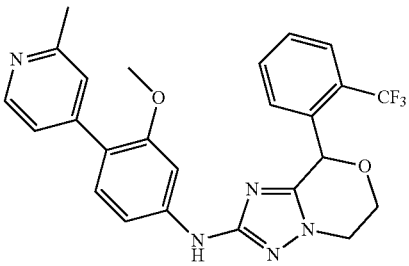 [SMILES: COc1cc(Nc2nc3n(n2)CCOC3c2ccccc2C(F)(F)F)ccc1-c1ccnc(C)c1]

Intermediate 59 (135 mg, 0.39 mmol), Pd₂(dba)₃ (36 mg, 0.039 mmol), X-Phos (37 mg, 0.078 mmol) and Cs₂CO₃ (379 mg, 1.16 mmol) were added to a solution of intermediate 49 (79 mg, 0.37 mmol) in 2-methyl-2-propanol (5 ml) under a N₂ atmosphere. The r.m. was heated at 110° C. for 20 h. Then, the r.m. was cooled to r.t., H₂O was added and the mixture was extracted with DCM. The combined organic layers were dried (MgSO₄), filtered and concentrated in vacuo. The residue was purified by flash column chromatography over silica gel (eluent: DCM/MeOH(NH₃) from 100/0 to 97/3). The product fractions were collected and concentrated in vacuo. The residue was further purified by RP preparative HPLC [RP Vydac Denali C18-10 μm, 250 g, I.D. 5 cm); mobile phase: a gradient of (0.25% NH₄HCO₃ solution in H₂O)/CH₃CN]. The product fractions were collected and worked up. Yield: 30 mg of compound 65 (16%).

Example B12 a) Preparation of Compound 27

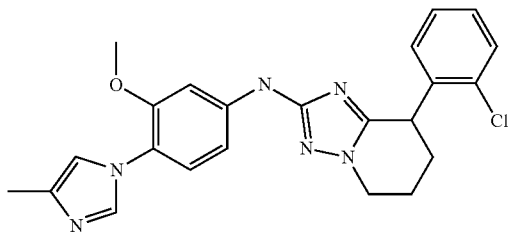 [SMILES: COc1cc(Nc2nc3n(n2)CCCC3c2ccccc2Cl)ccc1-n1cnc(C)c1]

Intermediate 42 (350 mg, 1.40 mmol), Pd$_2$(dba)$_3$ (128 mg, 0.14 mmol), X-Phos (134 mg, 0.28 mmol) and Cs$_2$CO$_3$ (1.37 g, 4.22 mmol) were added to a solution of intermediate 23 (478 mg, 1.41 mmol) in 2-methyl-2-propanol (5 ml) under a N$_2$ atmosphere. The r.m. was heated at 110° C. for 20 h. Then, the r.m. was cooled to r.t., water was added and the mixture was extracted with DCM. The combined organic layers were dried (MgSO$_4$), filtered and concentrated in vacuo. The residue was purified by flash column chromatography over silica gel (eluent: DCM/MeOH from 100/0 to 97/3). The product fractions were collected and concentrated in vacuo. The residue was triturated in DIPE, yielding 0.400 g of compound 27 (62%).

b) Preparation of Compounds 28 and 29

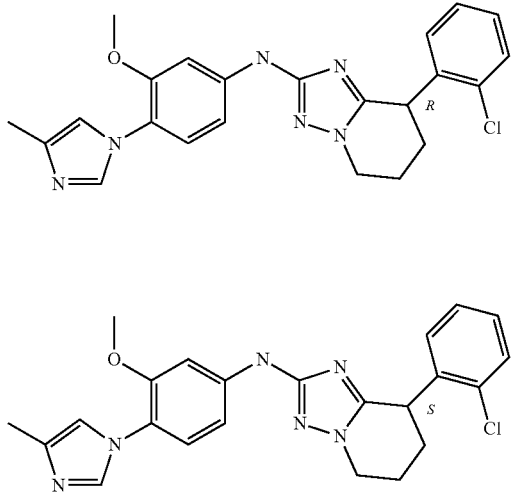

Compound 27 (330 mg) was separated into its enantiomers by preparative SFC (Chiralpak Diacel OJ 20×250 mm) Mobile phase (CO$_2$, MeOH with 0.2% 2-propylamine), to give compound 28 (80 mg, R-enantiomer) and compound 29 (70 mg, S-enantiomer).

Example B14

Preparation of Compound 34

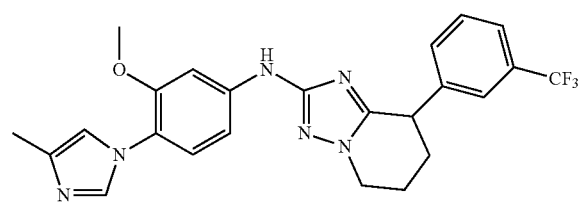 [SMILES: COc1cc(Nc2nc3n(n2)CCCC3c2cccc(C(F)(F)F)c2)ccc1-n1cnc(C)c1]

MeOH (30 ml) was added to Pt/C$_5$% (100 mg) under a N$_2$ atmosphere. Subsequently, compound 20 (165 mg, 0.36 mmol) in a mixture HCl/isopropanol (6N) (0.178 ml, 1.1 mmol) was added. The r.m. was stirred at 50° C. under a H$_2$ atmosphere until 2 eq. of H$_2$ was absorbed. The catalyst was filtered off over diatomaceous earth and the filtrate was evaporated. The residue was then purified by flash column chromatography over silica gel (eluent: DCM/MeOH from 100/0 to 99/1). The product fractions were collected and concentrated in vacuo, yielding 21 mg of compound 34 (56%).

Example B15

Preparation of Compound 33

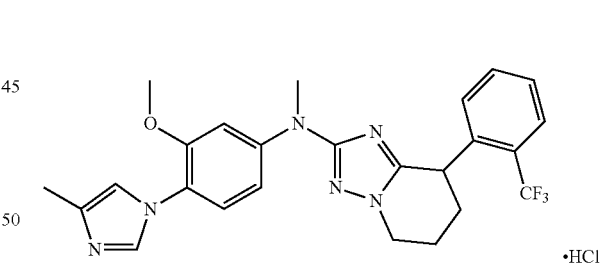

To compound 31 (110 mg, 0.24 mmol) in DMF (5 ml) at 0° C. was added NaH (60% in mineral oil; 9.4 mg, 0.24 mmol). The r.m. was then stirred at 0° C. for 10 min. Methyl iodide (33.3 mg, 0.24 mmol) was then added to the r.m., and the r.m. was then allowed to warm up to r.t. The r.m. was then diluted with water and extracted with EtOAc, dried over Na$_2$SO$_4$, and concentrated in vacuo. The residue was purified by flash column chromatography over silica gel (eluent: DCM/MeOH (NH$_3$) from 100/0 to 97/3). The product fractions were collected and concentrated in vacuo. The residue was dissolved in diethyl ether (5 ml) and a 6 N HCl sol. in 2-propanol (1 ml) was added dropwise to the stirring solution. The HCl salt was then collected by filtration and the product was dried in vacuo to yield 75 mg of compound 33 (.HCl; 66%).

Example B17

Preparation of Compound 66, 77 and 78

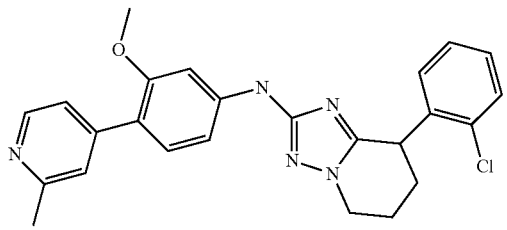

Co. No. 78
OR: +19.43°, 589 nm, 20° C., 0.211 w/v %, MeOH
Co. No. 77
OR: −20.33°, 589 nm, 20° C., 0.2312 w/v %, MeOH

Intermediate 55 (2.477 g, 7.9 mmol), $Pd_2(dba)_3$ (687 mg, 0.75 mmol), X-Phos (715 mg, 1.5 mmol) and $Cs_2CO_3$ (7.33 g, 22.5 mmol) were added to a solution of intermediate 23 (2.06 g, 8.3 mmol) in 2-methyl-2-propanol (100 ml) under a $N_2$ atmosphere. The r.m. was heated at 110° C. for 20 h. Then, the r.m. was cooled to r.t., water was added and the mixture was extracted with DCM. The combined organic layers were dried ($MgSO_4$), filtered and concentrated in vacuo. The residue was purified by flash column chromatography over silica gel (eluent: DCM/MeOH($NH_3$) from 100/0 to 97/3). The product fractions were collected and concentrated in vacuo. The residue was triturated in DIPE, filtered and dried, yielding 3.00 g of compound 66 (rac). Compound 66 was separated into its enantiomers by preparative SFC (Chiralpak Diacel OJ 20×250 mm; mobile phase: $CO_2$, MeOH with 0.2% 2-propylamine), to give 1.00 g of compound 78 and 1.01 g of compound 77.

Tables 1a, 1b, 1c and 1d list the compounds that were prepared by analogy to one of the above Examples. 'Pr.' refers to the Example number according to which protocol the compound was synthesized. 'Co. No.' means compound number.

In case no specific stereochemistry is indicated for a stereocenter of a compound, this means that the compound was obtained as a mixture of the R and the S form (RS).

In case no salt form is indicated, the compound was obtained as a free base. Salt forms of the free bases such as, for example, HCl salt forms, can easily be obtained by using typical procedures known to those skilled in the art. In a typical procedure for the conversion to a HCl salt form, for example, the free base was dissolved in a solvent such as, for example, DIPE or $Et_2O$, and subsequently a HCl solution in a solvent such as 2-propanol or $Et_2O$ was added dropwise. Stirring for a certain period of time, typically about 10 min, could enhance the rate of the reactions.

TABLE 1a

| Co. No. | Pr. | Het¹ | A¹ | A² | $Z^a$ | $R^x$ | $R^y$ | $R^z$ | Salt forms |
|---|---|---|---|---|---|---|---|---|---|
| 7 | B7 | methylimidazole | $COCH_3$ | CH | CH | Cl | H | H | |
| 19 | B7 | methylimidazole | $COCH_3$ | CH | CH | $CH_3$ | H | F | |
| 6 | B6 | methylimidazole | $COCH_3$ | CH | CH | $CF_3$ | H | F | |
| 10 | B3 | methylimidazole | $COCH_3$ | CH | N | $CH_3$ | H | F | |
| 20 | B7 | methylimidazole | $COCH_3$ | CH | CH | H | $CF_3$ | H | |

TABLE 1a-continued

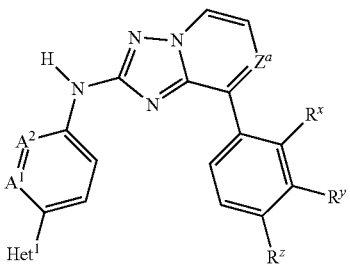

| Co. No. | Pr. | Het¹ | A¹ | A² | Zᵃ | Rˣ | Rʸ | Rᶻ | Salt forms |
|---|---|---|---|---|---|---|---|---|---|
| 8 | B3 | 1-methylimidazol-4-yl | COCH₃ | CH | N | CF₃ | H | H | |
| 22 | B8.a | 1-methylimidazol-4-yl | COCH₃ | CH | N | H | CF₃ | H | |
| 11 | B3 | 1-methylimidazol-4-yl | COCH₃ | N | N | CH₃ | H | F | |
| 186 | B3 | 1-methylimidazol-4-yl | COCH₃ | N | N | CH₃ | H | F | ·HCl |
| 23 | B7 | 4-methyloxazol-5-yl | COCH₃ | CH | CH | CF₃ | H | H | |
| 24 | B3 | 4-methyloxazol-5-yl | CH | CH | CH | CF₃ | H | H | |
| 3 | B3 | 3-methyl-1,2,4-triazol-1-yl | COCH₃ | CH | CH | CF₃ | H | H | |
| 4 | B4 | 3-methyl-1,2,4-triazol-1-yl | COCH₃ | CH | CH | CF₃ | H | F | |
| 2 | B2 | 2-methylpyridin-4-yl | COCH₃ | CH | CH | Cl | H | H | |
| 12 | B2 | 2-methylpyridin-4-yl | COCH₃ | N | N | CH₃ | H | F | |
| 187 | B2 | 2-methylpyridin-4-yl | COCH₃ | N | N | CH₃ | H | F | ·HCl |
| 74 | B2 | 2-methylpyridin-4-yl | COCH₃ | CH | C—CH₃ | H | H | F | |

TABLE 1a-continued
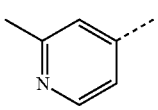
| Co. No. | Pr. | Het¹ | A¹ | A² | $Z^a$ | $R^x$ | $R^y$ | $R^z$ | Salt forms |
|---|---|---|---|---|---|---|---|---|---|
| 25 | B2 | 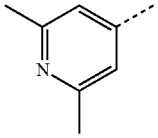 | CF | CH | CH | Cl | H | H | |
| 26 | B2 | 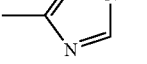 | CH | CH | CH | Cl | H | H | |
TABLE 1b
(OR means optical rotation)
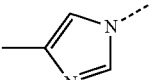
| Co. No. | Pr. | Het¹ | A¹ | A² | L¹ | $Z^b$ | $R^x$ | $R^y$ | $R^z$ | Salt forms/Stereo-chemistry/OR |
|---|---|---|---|---|---|---|---|---|---|---|
| 5 | B5 | 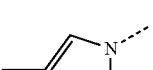 | COCH₃ | CH | NH | CH₂ | H | H | F | |
| 27 | B12.a | 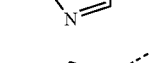 | COCH₃ | CH | NH | CH₂ | Cl | H | H | |
| 28 | B12.b | 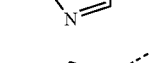 | COCH₃ | CH | NH | CH₂ | Cl | H | H | (R) |
| 29 | B12.b | 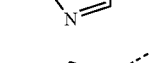 | COCH₃ | CH | NH | CH₂ | Cl | H | H | (S) |
| 30 | B1 | 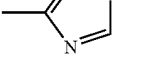 | COCH₃ | CH | NH | CH₂ | H | F | H | |

TABLE 1b-continued (OR means optical rotation)

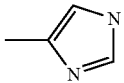

| Co. No. | Pr. | Het¹ | A¹ | A² | L¹ | $Z^b$ | $R^x$ | $R^y$ | $R^z$ | Salt forms/Stereo-chemistry/OR |
|---|---|---|---|---|---|---|---|---|---|---|
| 49 | B5 | 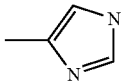 | COCH$_3$ | CH | NH | CH$_2$ | F | H | H | |
| 31 | B5 | 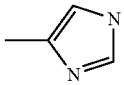 | COCH$_3$ | CH | NH | CH$_2$ | CF$_3$ | H | H | |
| 17 | B5 | 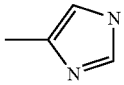 | COCH$_3$ | N | NH | CH$_2$ | CF$_3$ | H | H | |
| 18 | B5 | 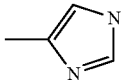 | COCH$_3$ | N | NH | CH$_2$ | Cl | H | H | |
| 32 | B14 | 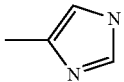 | COCH$_3$ | CH | NH | CH$_2$ | CH$_3$ | H | F | |
| 33 | B15 | 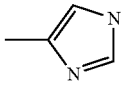 | COCH$_3$ | CH | NCH$_3$ | CH$_2$ | CF$_3$ | H | H | •HCl |
| 9 | B8.b | 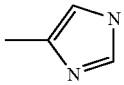 | COCH$_3$ | CH | NH | NH | CF$_3$ | H | H | |
| 13 | B8.c | 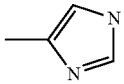 | COCH$_3$ | CH | NH | N—CH$_3$ | CF$_3$ | H | H | |
| 14 | B8.d | | COCH$_3$ | CH | NH | N—C(=O)CH$_3$ | CF$_3$ | H | H | |
| 47 | B11 | 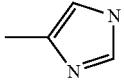 | COCH$_3$ | CH | NH | O | CF$_3$ | H | H | |
| 34 | B14 | 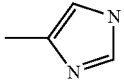 | COCH$_3$ | CH | NH | CH$_2$ | H | CF$_3$ | H | |

TABLE 1b-continued (OR means optical rotation)

| Co. No. | Pr. | Het¹ | A¹ | A² | L¹ | $Z^b$ | $R^x$ | $R^y$ | $R^z$ | Salt forms/Stereo-chemistry/OR |
|---|---|---|---|---|---|---|---|---|---|---|
| 35 | B5 | 4-methylimidazolyl | COCH₃ | CH | NH | CH₂ | H | OCH₃ | H | •2HCl •H₂O |
| 50 | B5 | 4-methylimidazolyl | COCH₃ | CH | NH | CH₂ | H | H | CF₃ | |
| 36 | B9 | 4-methylimidazolyl | COCH₃ | CH | (C=O)NH | CH₂ | H | H | F | |
| 37 | B5 | 4-methyloxazolyl | CH | CH | NH | CH₂ | CF₃ | H | H | |
| 38 | B5 | 4-methyloxazolyl | COCH₃ | CH | NH | CH₂ | CF₃ | H | H | |
| 39 | B5 | 2-methyloxazolyl | CH | CH | NH | CH₂ | CF₃ | H | H | |
| 15 | B5 | 3-methyl-1,2,4-triazolyl | COCH₃ | CH | NH | CH₂ | CF₃ | H | H | |
| 75 | B1 | 4-pyridyl | CH | CH | NH | CH₂ | CF₃ | H | H | |
| 46 | B1 | 3-pyridyl | CH | CH | NH | CH₂ | CF₃ | H | H | |
| 40 | B5 | 2-methyl-4-pyridyl | COCH₃ | CH | NH | CH₂ | H | OCH₃ | H | •1.8HCl •0.9 H₂O |
| 76 | B11 | 2-methyl-4-pyridyl | CH | CH | NH | O | Cl | H | H | |

TABLE 1b-continued (OR means optical rotation)

| Co. No. | Pr. | Het¹ | A¹ | A² | L¹ | $Z^b$ | $R^x$ | $R^y$ | $R^z$ | Salt forms/Stereo-chemistry/OR |
|---|---|---|---|---|---|---|---|---|---|---|
| 66 | B12.a or B17 | 2-methylpyridin-4-yl | COCH₃ | CH | NH | CH₂ | Cl | H | H | |
| 77 | B17 | 2-methylpyridin-4-yl | COCH₃ | CH | NH | CH₂ | Cl | H | H | OR: <20.33° |
| 78 | B17 | 2-methylpyridin-4-yl | COCH₃ | CH | NH | CH₂ | Cl | H | H | OR: +19.43° |
| 87 | B11 | 2-methylpyridin-4-yl | COCH₃ | CH | NH | O | Cl | H | H | |
| 79 | B11 | 2-methylpyridin-4-yl | COCH₃ | CH | NH | O | Cl | H | H | Enantiomer B |
| 80 | B11 | 2-methylpyridin-4-yl | COCH₃ | CH | NH | O | Cl | H | H | Enantiomer A |
| 81 | B17 | 2-methylpyridin-4-yl | CH | CH | NH | CH₂ | F | H | F | |
| 86 | B11 | 2-methylpyridin-4-yl | CF | CH | NH | O | CF₃ | H | H | |
| 65 | B11 | 2-methylpyridin-4-yl | COCH₃ | CH | NH | O | CF₃ | H | H | |
| 83 | B11 | 2-methylpyridin-4-yl | COCH₃ | CH | NH | O | CF₃ | H | H | Enantiomer B |
| 84 | B11 | 2-methylpyridin-4-yl | COCH₃ | CH | NH | O | CF₃ | H | H | Enantiomer A |

TABLE 1b-continued (OR means optical rotation)

| Co. No. | Pr. | Het¹ | A¹ | A² | L¹ | $Z^b$ | $R^x$ | $R^y$ | $R^z$ | Salt forms/Stereo-chemistry/OR |
|---|---|---|---|---|---|---|---|---|---|---|
| 85 | B11 | 2-methylpyridin-4-yl | CH | CH | NH | O | CF₃ | H | H | |
| 41 | B5 | 2-methylpyridin-4-yl | CH | CH | NH | CH₂ | Cl | H | H | |
| 68 | B12.b | 2-methylpyridin-4-yl | CH | CH | NH | CH₂ | Cl | H | H | OR: +23.74° |
| 73 | B12.b | 2-methylpyridin-4-yl | CH | CH | NH | CH₂ | Cl | H | H | OR: −18.39° |
| 88 | B11 | 2-methylpyridin-4-yl | CF | CH | NH | O | Cl | H | H | |
| 43 | B5 | 2-methylpyridin-4-yl | COCH₃ | CH | NH | CH₂ | CF₃ | H | H | |
| 44 | B5 | 2-methylpyridin-4-yl | COCH₃ | CH | NH | CH₂ | H | F | H | |
| 89 | B17 | 2-methylpyridin-4-yl | COCH₃ | CH | NH | CH₂ | H | H | CF₃ | |
| 91 | B17 | 2-methylpyridin-4-yl | COCH₃ | CH | NH | CH₂ | CH₃ | H | F | |
| 92 | B11 | 2-methylpyridin-4-yl | COCH₃ | CH | NH | O | CH₃ | H | F | |
| 90 | B17 | 2-methylpyridin-4-yl | CH | CH | NH | CH₂ | CH₃ | H | F | |

TABLE 1b-continued (OR means optical rotation)

| Co. No. | Pr. | Het¹ | A¹ | A² | L¹ | $Z^b$ | $R^x$ | $R^y$ | $R^z$ | Salt forms/Stereo-chemistry/OR |
|---|---|---|---|---|---|---|---|---|---|---|
| 93 | B17 | 2-methylpyridin-4-yl | CH | CH | NH | $CH_2$ | $CH_3$ | H | F | (R) |
| 94 | B17 | 2-methylpyridin-4-yl | CH | CH | NH | $CH_2$ | $CH_3$ | H | F | (S) |
| 82 | B17 | 2-methylpyridin-4-yl | $COCH_3$ | CH | NH | $CH_2$ | F | H | F | |
| 95 | B17 | 2-methylpyridin-4-yl | $COCH_3$ | CH | NH | $CH_2$ | F | H | F | Enantiomer B |
| 96 | B17 | 2-methylpyridin-4-yl | $COCH_3$ | CH | NH | $CH_2$ | F | H | F | Enantiomer A |
| 42 | B5 | 2-methylpyridin-4-yl | CH | CH | NH | $CH_2$ | $CF_3$ | H | H | |
| 97 | B17 | 2-methylpyridin-4-yl | CH | CH | NH | $CH_2$ | $CF_3$ | H | H | OR: −42.07° |
| 98 | B17 | 2-methylpyridin-4-yl | CH | CH | NH | $CH_2$ | $CF_3$ | H | H | OR: +40.65° |
| 99 | B17 | 2-methylpyridin-4-yl | $COCH_3$ | CH | NH | $CH_2$ | F | H | H | |
| 100 | B11 | 2-methylpyridin-4-yl | $COCH_3$ | CH | NH | O | F | H | F | |
| 1 | B1 | 2-methylpyridin-4-yl | $COCH_3$ | CH | NH | $CH_2$ | H | H | F | |

TABLE 1b-continued (OR means optical rotation)

| Co. No. | Pr. | Het¹ | A¹ | A² | L¹ | $Z^b$ | $R^x$ | $R^y$ | $R^z$ | Salt forms/Stereo-chemistry/OR |
|---|---|---|---|---|---|---|---|---|---|---|
| 16 | B1 | 2-methylpyridin-4-yl | COCH₃ | N | NH | CH₂ | H | H | F | |
| 101 | B17 | 2-methylpyridin-4-yl | COCH₃ | CH | NH | CH=CH₃ | H | H | F | CIS (rac) |
| 102 | B17 | 2-methylpyridin-4-yl | CF | CH | NH | CH₂ | H | OCH₃ | H | |
| 103 | B17 | 2-methylpyridin-4-yl | CH | CH | NH | CH₂ | H | OCH₃ | H | |
| 104 | B17 | 2-methylpyridin-4-yl | COCH₃ | CH | NH | CH₂ | H | F | OCH₃ | 1.3 HCl 2.3 H₂O |
| 105 | B6 | 2-methylpyridin-4-yl | CH | CH | NH | CH₂ | H | F | OCH₃ | 1.6 HCl 2.4 H₂O |
| 106 | B17 | 2-methylpyridin-4-yl | CH | CH | NH | CH₂ | H | OCH₃ | F | |
| 107 | B17 | 2-methylpyridin-4-yl | COCH₃ | CH | NH | CH₂ | H | OCH₃ | F | |
| 111 | B17 | 2-methylpyridin-4-yl | COCH₃ | CH | NH | CH₂ | H | N(CH₃)₂ | H | |
| 45 | B1 | 2,5-dimethylpyridin-4-yl | CH | CH | NH | CH₂ | CF₃ | H | H | |

TABLE 1c

| Co. No. | Pr. | Structure | Salt form |
|---|---|---|---|
| 21 | B7 | 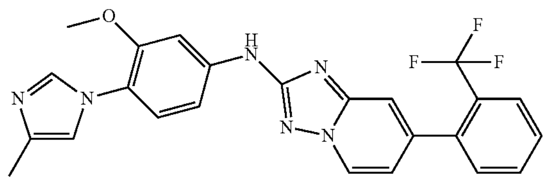 [SMILES: COc1cc(Nc2nc3cc(-c4ccccc4C(F)(F)F)ccn3n2)ccc1-n1cnc(C)c1] | |
| 181 | B2 | 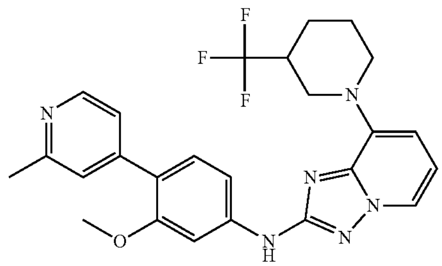 [SMILES: COc1cc(Nc2nc3c(N4CCCC(C(F)(F)F)C4)cccn3n2)ccc1-c1ccnc(C)c1] | 1.5 HCl 1.7 $H_2O$ |
| 62 | BB1 | 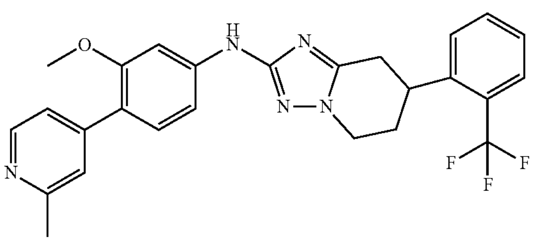 [SMILES: COc1cc(Nc2nc3n(n2)CCC(c2ccccc2C(F)(F)F)C3)ccc1-c1ccnc(C)c1] | •HCl |
| 63 | B7 | 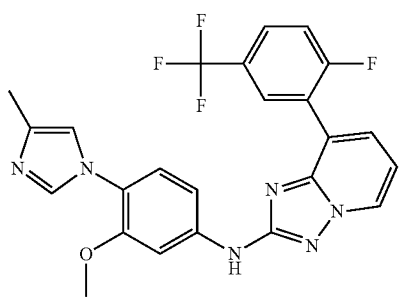 [SMILES: COc1cc(Nc2nc3c(-c4cc(C(F)(F)F)ccc4F)cccn3n2)ccc1-n1cnc(C)c1] | |
| 72 | B10 | 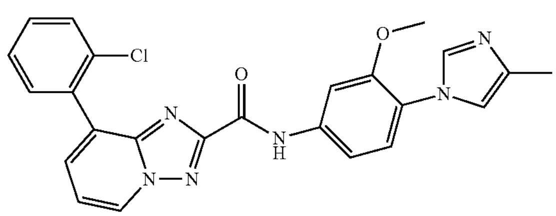 [SMILES: COc1cc(NC(=O)c2nc3c(-c4ccccc4Cl)cccn3n2)ccc1-n1cnc(C)c1] | |
| 48 | B5 | 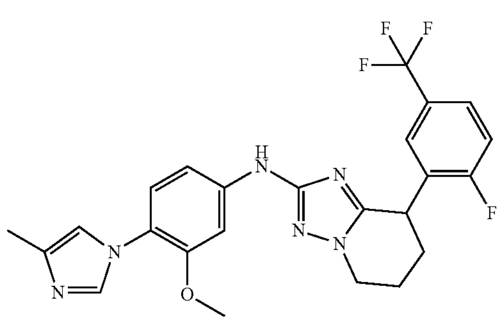 [SMILES: COc1cc(Nc2nc3n(n2)CCCC3c2cc(C(F)(F)F)ccc2F)ccc1-n1cnc(C)c1] | |

TABLE 1c-continued

| Co. No. | Pr. | Structure | Salt form |
|---|---|---|---|
| 51 | B5 | 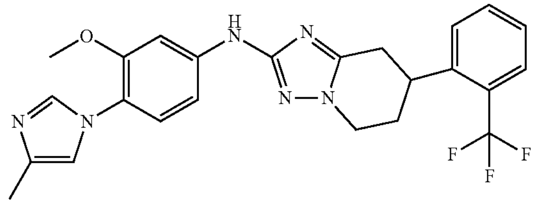 [SMILES: COc1cc(Nc2nc3n(n2)CCC(c2ccccc2C(F)(F)F)C3)ccc1-n1cnc(C)c1] | |
| 52 | B17 | 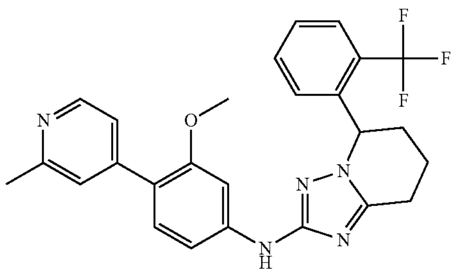 [SMILES: COc1cc(Nc2nc3n(n2)C(c2ccccc2C(F)(F)F)CCC3)ccc1-c1ccnc(C)c1] | 1.8 HCl<br>3 H$_2$O |

TABLE 1d

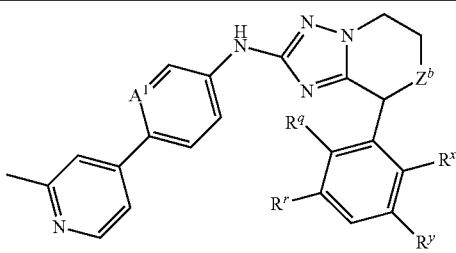

| Co. No. | Pr. | A$^1$ | Z$^b$ | R$^x$ | R$^y$ | R$^q$ | R$^r$ | Salt forms/Stereo-chemistry |
|---|---|---|---|---|---|---|---|---|
| 184 | B17 | CF | CH$_2$ | F | H | H | OCH$_3$ | |
| 185 | B17 | CH | CH$_2$ | H | F | H | OCH$_3$ | |
| 110 | B17 | COCH$_3$ | CH$_2$ | Cl | H | F | H | |
| 116 | B17 | CH | CH$_2$ | Cl | H | F | H | |
| 144 | B17 | CH | CH$_2$ | CH$_3$ | H | H | CF$_3$ | |
| 151 | B17 | COCH$_3$ | CH$_2$ | CH$_3$ | H | H | CF$_3$ | |
| 183 | B17 | CH | CH$_2$ | F | H | H | OCH$_3$ | |
| 172 | B17 | COCH$_3$ | CH$_2$ | F | H | H | OCH$_3$ | 1.7 HCl |
| 182 | B17 | COCH$_3$ | CH$_2$ | F | H | H | CF$_3$ | |
| 114 | B17 | CH | CH$_2$ | F | H | H | CF$_3$ | |
| 115 | B17 | COCH$_3$ | CH$_2$ | H | OCH$_3$ | H | F | |

Analytical Part
LCMS (Liquid Chromatography/Mass spectrometry)
General Procedure A The LC measurement was performed using an Acquity HPLC (Ultra Performance Liquid Chromatography) (Waters) system comprising a binary pump, a sample organizer, a column heater (set at 55° C.), a diode-array detector (DAD) and a column as specified in the respective methods below. Flow from the column was split to a MS spectrometer. The MS detector was configured with an electrospray ionization source. Mass spectra were acquired by scanning from 100 to 1000 in 0.18 seconds (sec) using a dwell time of 0.02 sec. The capillary needle voltage was 3.5 kV and the source temperature was maintained at 140° C. N$_2$ was used as the nebulizer gas. Data acquisition was performed with a Waters-Micromass MassLynx-Openlynx data system.

General Procedure B

The HPLC measurement was performed using an Alliance HT 2790 (Waters) system comprising a quaternary pump with degasser, an autosampler, a column oven (set at 45° C., unless otherwise indicated), a DAD and a column as specified in the respective methods below. Flow from the column was split to a MS spectrometer. The MS detector was configured with an electrospray ionization source. Mass spectra were acquired by scanning from 100 to 1000 in 1 sec using a dwell time of 0.1 sec. The capillary needle voltage was 3 kV and the source temperature was maintained at 140° C. N$_2$ was used as the nebulizer gas. Data acquisition was performed with a Waters-Micromass MassLynx-Openlynx data system.

General Procedure C

The HPLC measurement was performed using an Agilent 1100 module comprising a pump, a DAD (wavelength 220 nm), a column heater and a column as specified in the respective methods below. Flow from the column was split to a Agilent MSD Series G1946C and G1956A. MS detector was configured with API-ES (atmospheric pressure electrospray ionization). Mass spectra were acquired by scanning from 100 to 1000. The capillary needle voltage was 2500 V for positive ionization mode and 3000 V for negative ionization mode. Fragmentation voltage was 50 V. Drying gas temperature was maintained at 350° C. at a flow of 10 l/min.

LCMS Method 1

In addition to general procedure A: Reversed phase HPLC was carried out on a bridged ethylsiloxane/silica hybrid (BEH) C18 column (1.7 µm, 2.1×50 mm; Waters Acquity) with a flow rate of 0.8 ml/minute (min) 2 Mobile phases (25 mM ammonium acetate (NH$_4$OAc)/CH$_3$CN 95/5; mobile phase B: CH$_3$CN) were used to run a gradient condition from 95% A and 5% B to 5% A and 95% B in 1.3 min and hold for 0.3 min. An injection volume of 0.5 µl was used. Cone voltage was 30 V for positive ionization mode and 30 V for negative ionization mode.

LCMS Method 2

In addition to general procedure B: Column heater was set at 40° C. Reversed phase HPLC was carried out on an Xterra MS C18 column (3.5 µm, 4.6×100 mm) with a flow rate of 1.6 ml/min. 3 Mobile phases (mobile phase A: 95% 25 mM NH$_4$OAc+5% CH$_3$CN; mobile phase B: CH$_3$CN; mobile phase C: MeOH) were employed to run a gradient condition from 100% A to 1% A, 49% B and 50% C in 6.5 min, to 1% A and 99% B in 1 min and hold these conditions for 1 min and reequilibrate with 100% A for 1.5 min. An injection volume of 10 μl was used. Cone voltage was 10 V for positive ionization mode and 20 V for negative ionization mode.

LCMS Method 3

In addition to general procedure B: Column heater was set at 40° C. Reversed phase HPLC was carried out on an Xterra MS C18 column (3.5 μm, 4.6×100 mm) with a flow rate of 1.6 ml/min. 3 Mobile phases (mobile phase A: 95% 25 mM NH$_4$OAc+5% CH$_3$CN; mobile phase B: CH$_3$CN; mobile phase C: MeOH) were employed to run a gradient condition from 100% A to 1% A, 49% B and 50% C in 6.5 min, to 1% A, 99% B in 0.5 min and keep these conditions for 1 min. An injection volume of 10 μl was used. Cone voltage was 10 V for positive ionization mode and 20 V for negative ionization mode.

LCMS Method 4

In addition to general procedure B: Column heater was set at 45° C. Reversed phase HPLC was carried out on an Atlantis C18 column (3.5 μm, 4.6×100 mm) with a flow rate of 1.6 ml/min. 2 Mobile phases (mobile phase A: 70% MeOH+30% H$_2$O; mobile phase B: 0.1% formic acid in H$_2$O/MeOH 95/5) were employed to run a gradient condition from 100% B to 5% B+95% A in 9 min and hold these conditions for 3 min. An injection volume of 10 μl was used. Cone voltage was 10 V for positive ionization mode and 20 V for negative ionization mode.

LCMS Method 5

In addition to general procedure A: Reversed phase HPLC was carried out on a BEH C18 column (1.7 μm, 2.1×50 mm; Waters Acquity) with a flow rate of 0.8 ml/min. 2 Mobile phases (mobile phase A: 0.1% formic acid in H$_2$O/MeOH 95/5; mobile phase B: MeOH) were used to run a gradient condition from 95% A and 5% B to 5% A and 95% B in 1.3 min and hold for 0.2 min. An injection volume of 0.5 μl was used. Cone voltage was 10 V for positive and 20 V for negative ionization mode.

Melting Points

Unless otherwise mentioned, melting points (m.p.) were determined with a DSC823e (Mettler-Toledo). Melting points were measured with a temperature gradient of 30° C./min. Maximum temperature was 400° C. Values are peak values.

The results of the analytical measurements are shown in table 2a.

TABLE 2a

Retention time ($R_t$) in min., [M + H]$^+$ peak (protonated molecule), LCMS method and m.p. (melting point in ° C.). (n.d. means not determined)

| Co. No. | $R_t$ | [M + H]$^+$ | LCMS Method | m.p. (° C.) |
|---|---|---|---|---|
| 1 | 1.16 | 430 | 1 | 207.1 |
| 2 | 1.25 | 442 | 1 | 186.7 |
| 3 | 5.81 | 466 | 2 | 195.5 |
| 4 | 1.32 | 484 | 1 | n.d. |
| 5 | 0.95 | 419 | 1 | n.d. |
| 6 | 1.07 | 483 | 1 | 238.4 |
| 7 | 1.04 | 431 | 1 | 235.0 |
| 8 | 1.32 | 466 | 1 | 206.9 |
| 9 | 5.28 | 470 | 2 | 248.0 |
| 10 | 0.99 | 430 | 1 | n.d. |
| 11 | 1.01 | 431 | 1 | 278.9 |
| 12 | 1.12 | 442 | 1 | 268.2 |
| 13 | 1.05 | 484 | 1 | n.d. |
| 14 | 0.86 | 512 | 1 | n.d. |
| 15 | 1.02 | 470 | 1 | 233.2 |
| 16 | 1.06 | 431 | 1 | n.d. |
| 17 | 1.08 | 470 | 1 | n.d. |
| 18 | 1.04 | 436 | 1 | n.d. |
| 19 | 6.20 | 429 | 2 | n.d. |
| 20 | 1.15 | 465 | 1 | 175.0 |
| 21 | 1.09 | 465 | 1 | n.d. |
| 22 | 1.16 | 466 | 1 | 199.0 |
| 23 | 1.12 | 466 | 1 | 220.3 |
| 24 | 1.14 | 436 | 1 | n.d. |
| 25 | 1.12 | 430 | 1 | 251.0 |
| 26 | 1.17 | 426 | 1 | 228.1 |
| 27 | 1.01 | 435 | 1 | n.d. |
| 28 | 1.01 | 435 | 1 | 195.0 |
| 29 | 1.02 | 435 | 1 | 193.2 |
| 30 | 0.98 | 419 | 1 | 200.6 |
| 31 | 1.06 | 469 | 1 | 187.9 |
| 32 | 1.01 | 433 | 1 | 249.0 |
| 33 | 1.12 | 483 | 1 | n.d. |
| 34 | 1.05 | 469 | 1 | 224.9 |
| 35 | 5.96 | 431 | 4 | 163.0 |
| 36 | 4.70 | 447 | 3 | n.d. |
| 37 | 6.07 | 440 | 2 | 207.4 |
| 38 | 1.12 | 470 | 1 | 258.5 |
| 39 | 1.12 | 440 | 1 | 162.0 |
| 40 | 1.04 | 442 | 1 | n.d. |
| 41 | 1.10 | 416 | 1 | 227.2 |
| 42 | 1.13 | 450 | 1 | n.d. |
| 43 | 1.13 | 480 | 1 | n.d. |
| 44 | 1.05 | 430 | 1 | 170.1 |
| 45 | 1.18 | 464 | 1 | n.d. |
| 46 | 1.12 | 436 | 1 | n.d. |
| 47 | 0.90 | 471 | 5 | 202.9 |
| 48 | 6.72 | 487 | 4 | 204.4 |
| 49 | 0.97 | 419 | 1 | 188.3 |
| 50 | 1.07 | 469 | 1 | 229.7 |
| 51 | 1.05 | 469 | 1 | n.d. |
| 52 | 1.03 | 480 | 5 | n.d. |
| 62 | 1.13 | 480 | 1 | n.d. |
| 63 | 7.15 | 483 | 4 | n.d. |
| 65 | 5.93 | 482 | 2 | n.d. |
| 68 | 1.10 | 416 | 1 | n.d. |
| 72 | 5.79 | 459 | 2 | n.d. |
| 73 | 1.10 | 416 | 1 | n.d. |
| 74 | 1.14 | 440 | 1 | n.d. |
| 75 | 1.10 | 436 | 1 | 240.4 |
| 76 | 1.00 | 418 | 1 | 216.1 |
| 77 | 1.09 | 446 | 1 | 167.9 |
| 78 | 1.09 | 446 | 1 | 169.0 |
| 79 | 1.01 | 448 | 1 | n.d. |
| 80 | 1.02 | 448 | 1 | n.d. |
| 81 | 1.05 | 418 | 1 | 193.7 |
| 82 | 1.06 | 448 | 1 | 192.7 |
| 83 | 1.07 | 482 | 1 | 139.5 |
| 84 | 1.07 | 482 | 1 | 89.6 |
| 85 | 1.05 | 452 | 1 | n.d. |
| 86 | 0.97 | 470 | 5 | n.d. |
| 87 | 0.87 | 448 | 5 | 181.3 |
| 88 | 1.05 | 436 | 1 | n.d. |
| 89 | 1.14 | 480 | 1 | n.d. |
| 90 | 1.08 | 414 | 1 | 153.9 |
| 91 | 1.09 | 444 | 1 | 161.4 |
| 92 | 1.03 | 446 | 1 | 201.9 |
| 93 | 1.07 | 414 | 1 | n.d. |
| 94 | 1.07 | 414 | 1 | n.d. |
| 95 | 1.06 | 448 | 1 | n.d. |
| 96 | 1.06 | 448 | 1 | n.d. |
| 97 | 1.14 | 450 | 1 | n.d. |
| 98 | 1.14 | 450 | 1 | 157.1 |
| 99 | 1.04 | 430 | 1 | 214.9 |
| 100 | 0.98 | 450 | 1 | 217.2 |
| 101 | 0.98 | 444 | 5 | 122.1 |
| 102 | 1.07 | 430 | 1 | 148.4 |
| 103 | 1.01 | 412 | 1 | 221.6 |
| 104 | 1.03 | 460 | 1 | n.d. |
| 105 | 1.01 | 430 | 1 | n.d. |

TABLE 2a-continued

Retention time ($R_t$) in min., [M + H]+ peak (protonated molecule), LCMS method and m.p. (melting point in ° C.). (n.d. means not determined)

| Co. No. | $R_t$ | [M + H]+ | LCMS Method | m.p. (° C.) |
|---|---|---|---|---|
| 106 | 1.03 | 430 | 1 | 150.6 |
| 107 | 1.03 | 460 | 1 | 147.4 |
| 110 | 1.09 | 464 | 1 | 174.0 |
| 111 | n.d. | n.d. | — | n.d. |
| 114 | 1.14 | 468 | 1 | 194.4 |
| 115 | 6.61 | 460 | 4 | n.d. |
| 116 | 1.08 | 434 | 1 | 234.4 |
| 144 | 1.16 | 464 | 1 | n.d. |
| 151 | 1.16 | 494 | 1 | 146.8 |
| 172 | 1.05 | 460 | 1 | n.d. |
| 181 | 1.23 | 483 | 1 | n.d. |
| 182 | 1.14 | 498 | 1 | 173.1 |
| 183 | 6.22 | 430 | 4 | 204.6 |
| 184 | 1.09 | 448 | 1 | 221.5 |
| 185 | 1.05 | 430 | 1 | 175.1 |
| 186 | 1.02 | 431 | 1 | n.d. |
| 187 | 1.12 | 442 | 1 | n.d. |

For Co. No. 66, the [M-H]− peak was detected: Rt 1.10; [M-H]− 444; LCMS Method 1;
Melting Point: 176.6° C.

Optical Rotation (OR)

The optical rotation was measured using a Perkin Elmer 341 polarimeter. $[\alpha]_D^{20}$ indicates the optical rotation measured with light at the wavelength (λ) of 365 nm or 589 nm, at a temperature of 20° C. The cell pathlength is 1 dm. Behind the actual value the wavelength (λ) in nm, concentration (Conc.) and solvent of the solution which was used to measure the optical rotation are mentioned.

TABLE 2b

Optical rotation

| Co. No. | $[\alpha]_D^{20}$ | λ | Conc. | solvent |
|---|---|---|---|---|
| 28 | +45.94° | 365 | 0.3004 w/v % | MeOH |
| 29 | −42.61° | 365 | 0.3168 w/v % | MeOH |
| 68 | +23.74° | 589 | 0.4296 w/v % | DMF |
| 73 | −18.39° | 589 | 0.3806 w/v % | DMF |
| 77 | −20.33° | 589 | 0.2312 w/v % | MeOH |
| 78 | +19.43° | 589 | 0.2110 w/v % | MeOH |
| 93 | −33.53 | 589 | 0.3460 w/v % | MeOH |
| 94 | +33.46 | 589 | 0.3586 w/v % | MeOH |
| 97 | −42.07° | 589 | 0.3518 w/v % | MeOH |
| 98 | +40.65° | 589 | 0.3616 w/v % | MeOH |

SFC-MS

For SFC-MS, an analytical SFC system from Berger Instruments (Newark, Del., USA) was used comprising a dual pump control module (FCM-1200) for delivery of $CO_2$ and modifier, a thermal control module for column heating (TCM2100) with temperature control in the range 1-150° C. and column selection valves (Valco, VICI, Houston, Tex., USA) for 6 different columns. The photodiode array detector (Agilent 1100, Waldbronn, Germany) is equipped with a high-pressure flow cell (up to 400 bar) and configured with a CTC LC Mini PAL auto sampler (Leap Technologies, Carrboro, N.C., USA). A ZQ mass spectrometer (Waters, Milford, Mass., USA) with an orthogonal Z-electrospray interface is coupled with the SFC-system. Instrument control, data collection and processing were performed with an integrated platform consisting of the SFC ProNTo software and Masslynx software.

Co. No. 83-84: SFC-MS was carried out on a OD-H column (500×4.6 mm) (Daicel Chemical Industries Ltd) with a flow rate of 3 ml/min. Two mobile phases (mobile phase A: $CO_2$; mobile phase B: MeOH containing 0.2% iPrNH$_2$) were employed. First 25% B was hold for 18 min. Then a gradient was applied from 25% B to 50% B in 2.5 min and hold for 4.1 min. Column temperature was set at 50° C. Under these conditions, Co. No. 84 ('enantiomer A') had a shorter $R_t$ on the column than Co. No. 83 ('enantiomer B'). The measurement was compared against the racemic mixture.

Co. No. 95-96: SFC-MS was carried out on a OJ-H column (500×4.6 mm) (Daicel Chemical Industries Ltd) with a flow rate of 3 ml/min. Two mobile phases (mobile phase A: $CO_2$; mobile phase B: MeOH containing 0.2% iPrNH$_2$) were employed. First 25% B was hold for 18 min. Then a gradient was applied from 25% B to 50% B in 2.5 min and hold for 4.1 min. Column temperature was set at 50° C. Under these conditions, Co. No. 96 ('enantiomer A') had a shorter $R_t$ on the column than Co. No. 95 ('enantiomer B'). The measurement was compared against the racemic mixture.

Co. No. 79-80: SFC-MS was carried out on a OJ-H column (500×4.6 mm) (Daicel Chemical Industries Ltd) with a flow rate of 3 ml/min. Two mobile phases (mobile phase A: $CO_2$; mobile phase B: MeOH containing 0.2% iPrNH$_2$) were employed. 35% B was hold for 15 min. Column temperature was set at 50° C. Under these conditions, Co. No. 80 ('enantiomer A') had a shorter $R_t$ on the column than Co. No. 79 ('enantiomer B'). The measurement was compared against the racemic mixture.

NMR

For a number of compounds, $^1$H NMR spectra were recorded on a Bruker DPX-360, on a Bruker DPX-400 or on a Bruker Avance 600 spectrometer with standard pulse sequences, operating at 360 MHz, 400 MHz and 600 MHz respectively, using CHLOROFORM-d (deuterated chloroform, CDCl$_3$) or DMSO-d$_6$ (deuterated DMSO, dimethyl-d6 sulfoxide) as solvents. Chemical shifts (δ) are reported in parts per million (ppm) relative to tetramethylsilane (TMS), which was used as internal standard.

| Co. No. | NMR result |
|---|---|
| 1 | (360 MHz, CDCl$_3$) δ ppm 1.96-2.14 (m, 2 H) 2.17-2.25 (m, 1 H) 2.29-2.40 (m, 1 H) 2.58 (s, 3 H) 3.83 (s, 3 H) 4.12-4.27 (m, 3 H) 6.68 (s, 1 H) 6.94 (dd, J = 8.23, 2.01 Hz, 1 H) 7.03 (t, J = 8.78 Hz, 2 H) 7.16 (dd, J = 8.78, 5.12 Hz, 2 H) 7.21-7.35 (m, 4 H) 8.46 (d, J = 5.12 Hz, 1 H) |
| 2 | (400 MHz, DMSO-d$_6$) δ ppm 2.48 (s, 3 H) 3.77 (s, 3 H) 7.15 (t, J = 7.27, 6.86 Hz, 1 H) 7.27 (dd, J = 8.07, 1.61 Hz, 1 H) 7.28-7.39 (m, 3 H) 7.42-7.57 (m, 2 H) 7.60 (dd, J = 7.27, 1.21 Hz, 1 H) 7.61-7.64 (m, 2 H) 7.66 (d, J = 1.61 Hz, 1 H) 8.39 (d, J = 4.84 Hz, 1 H) 8.87 (dd, J = 6.86, 1.21 Hz, 1 H) 9.96 (s, 1 H) |
| 3 | (360 MHz, DMSO-d$_6$) δ ppm 2.32 (s, 3 H) 3.78 (s, 3 H) 7.16 (t, J = 6.95 Hz, 1 H) 7.22 (dd, J = 8.60, 2.01 Hz, 1 H) 7.43 (d, J = 8.78 Hz, 1 H) 7.52 (d, J = 6.95 Hz, 1 H) 7.61 (d, J = 7.32 Hz, 1 H) 7.66 (d, J = 2.20 Hz, 1 H) 7.71 (t, J = 7.68 Hz, 1 H) 7.80 (t, |

-continued

| Co. No. | NMR result |
|---|---|
| | J = 7.32 Hz, 1 H) 7.92 (d, J = 7.32 Hz, 1 H) 8.63 (s, 1 H) 8.87 (dd, J = 6.59, 1.10 Hz, 1 H) 10.00 (s, 1 H) |
| 4 | (360 MHz, CDCl$_3$) δ ppm 2.49 (s, 3 H) 3.92 (s, 3 H) 6.96 (dd, J = 8.60, 2.38 Hz, 1 H) 7.00 (t, J = 6.95 Hz, 1 H) 7.01 (s, 1 H) 7.32-7.43 (m, 2 H) 7.48-7.61 (m, 3 H) 7.65 (d, J = 2.20 Hz, 1 H) 8.49 (s, 1 H) 8.51 (dd, J = 6.59, 0.73 Hz, 1 H) |
| 5 | (360 MHz, DMSO-d$_6$) δ ppm 1.87-2.11 (m, 3 H) 2.12 (s, 3 H) 2.17-2.27 (m, 1 H) 3.70 (s, 3 H) 4.13 (t, J = 5.67 Hz, 2 H) 4.25 (dd, J = 8.97, 5.67 Hz, 1 H) 6.97 (s, 1 H) 7.07-7.22 (m, 4 H) 7.25-7.33 (m, 2 H) 7.38 (d, J = 1.46 Hz, 1 H) 7.59 (d, J = 1.10 Hz, 1 H) 9.37 (s, 1 H) |
| 6 | (360 MHz, DMSO-d$_6$) δ ppm 2.14 (s, 3 H) 3.75 (s, 3 H) 7.01 (s, 1 H) 7.14 (t, J = 6.95 Hz, 1 H) 7.19-7.26 (m, 2 H) 7.51 (d, J = 7.32 Hz, 1 H) 7.59 (s, 1 H) 7.63 (s, 1 H) 7.65-7.71 (m, 2 H) 7.83 (dd, J = 8.96, 2.01 Hz, 1 H) 8.89 (dd, J = 6.59, 0.73 Hz, 1 H) 9.98 (s, 1 H) |
| 7 | (600 MHz, DMSO-d$_6$) δ ppm 2.14 (s, 3 H) 3.76 (s, 3 H) 7.01 (s, 1 H) 7.15 (t, J = 7.0 Hz, 1 H), 7.22 (s, 2 H), 7.44-7.54 (m, 2 H) 7.60 (dd, J = 7.3, 1.2 Hz, 1 H), 7.61-7.64 (m, 3 H), 7.69 (s, 1 H), 8.86 (dd, J = 6.7, 1.2 Hz, 1 H), 9.95 (s, 1 H) |
| 8 | (360 MHz, DMSO-d$_6$) δ ppm 2.14 (s, 3 H) 3.76 (s, 3 H) 7.04 (s, 1 H) 7.23 (dd, J = 8.78, 1.83 Hz, 1 H) 7.26 (d, J = 8.78 Hz, 1 H) 7.62 (d, J = 1.83 Hz, 1 H) 7.67 (s, 1 H) 7.74-7.89 (m, 3 H) 7.97 (d, J = 7.68 Hz, 1 H) 8.24 (d, J = 4.39 Hz, 1 H) 8.98 (d, J = 4.39 Hz, 1 H) 10.23 (s, 1 H) |
| 9 | (400 MHz, DMSO-d$_6$) δ ppm 2.13 (s, 3 H) 3.22-3.32 (m, 1 H) 3.32-3.42 (m, 2 H) 3.68 (s, 3 H) 4.04-4.13 (m, 1 H) 4.13-4.24 (m, 1 H) 5.33 (d, J = 4.04 Hz, 1 H) 6.98 (s, 1 H) 7.07 (dd, J = 8.48, 2.02 Hz, 1 H) 7.14 (d, J = 8.48 Hz, 1 H) 7.36 (d, J = 2.02 Hz, 1 H) 7.49-7.57 (m, 2 H) 7.61 (d, J = 0.81 Hz, 1 H) 7.64 (t, J = 8.07 Hz, 1 H) 7.77 (d, J = 8.07 Hz, 1 H) 9.34 (s, 1 H) |
| 10 | (360 MHz, CDCl$_3$) δ ppm 2.30 (s, 3 H) 2.43 (s, 3 H) 3.88 (s, 3 H) 6.87 (s, 1 H) 7.00-7.11 (m, 3 H) 7.17 (s, 1 H) 7.20 (d, J = 8.42 Hz, 1 H) 7.57 (d, J = 2.20 Hz, 1 H) 7.63 (s, 1 H) 7.73 (d, J = 8.42, 5.85 Hz, 1 H) 8.21 (dd, J = 4.39, 0.73 Hz, 1 H) 8.41 (dd, J = 4.39, 0.73 Hz, 1 H) |
| 11 | (360 MHz, CDCl$_3$) δ ppm 2.30 (d, J = 1.10 Hz, 3 H) 2.43 (s, 3 H) 3.94 (s, 3 H) 6.89 (t, J = 1.10 Hz, 1 H) 7.02-7.13 (m, 2 H) 7.58 (d, J = 8.42 Hz, 1 H) 7.66 (d, J = 1.46 Hz, 1 H) 7.67 (s, 1 H) 7.73 (dd, J = 8.23, 6.04 Hz, 1 H) 7.79 (d, J = 8.42 Hz, 1 H) 8.23 (d, J = 4.39 Hz, 1 H) 8.43 (d, J = 4.39 Hz, 1 H) |
| 12 | (360 MHz, CDCl$_3$) δ ppm 2.43 (s, 3 H) 2.60 (s, 3 H) 3.95 (s, 3 H) 7.03-7.13 (m, 2 H) 7.33 (d, J = 5.49 Hz, 1 H) 7.37 (s, 1 H) 7.69 (s, 1 H) 7.71-7.76 (m, 2 H) 7.81 (d, 1 H) 8.23 (dd, J = 4.39, 0.73 Hz, 1 H) 8.44 (dd, J = 4.39, 0.73 Hz, 1 H) 8.50 (d, J = 5.12 Hz, 1 H) |
| 13 | (400 MHz, DMSO-d$_6$) δ ppm 2.12 (d, J = 0.81 Hz, 3 H) 2.19 (s, 3 H) 3.05 (td, J = 12.11, 4.04 Hz, 1 H) 3.34 (dd, J = 12.11, 4.04 Hz, 1 H) 3.66 (s, 3 H) 4.17 (dd, J = 12.11, 3.43 Hz, 1 H) 4.30 (td, J = 12.11, 4.44 Hz, 1 H) 4.69 (s, 1 H) 6.95 (s, 1 H) 7.02 (dd, J = 8.88, 2.22 Hz, 1 H) 7.12 (d, J = 8.88 Hz, 1 H) 7.39 (d, J = 2.22 Hz, 1 H) 7.53 (t, J = 7.47 Hz, 1 H) 7.57 (d, J = 1.21 Hz, 1 H) 7.59-7.72 (m, 2 H) 7.76 (d, J = 7.67 Hz, 1 H) 9.42 (s, 1 H) |
| 14 | (400 MHz, DMSO-d$_6$) δ ppm 2.12 (s, 3 H), 2.14 (s, 3 H), 3.70 (s, 3 H), 3.85-3.94 (m, 1 H), 4.22-4.35 (m, 2 H), 4.38 (d, J = 14.9 Hz, 1 H), 6.81 (s, 1 H), 6.92 (s, 1 H), 7.07-7.13 (m, 2 H), 7.35 (d, J = 7.7 Hz, 1 H), 7.42 (s, 1 H), 7.49-7.57 (m, 2 H), 7.60 (t, J = 7.3 Hz, 1 H), 7.76 (d, J = 7.7 Hz, 1 H), 9.06 (s, 1 H) |
| 15 | (360 MHz, CDCl$_3$) δ ppm 1.84-2.00 (m, 1 H) 2.08-2.34 (m, 2 H) 2.39-2.47 (m, 1 H) 2.48 (s, 3 H) 3.86 (s, 3 H) 4.16-4.36 (m, 2 H) 4.57 (dd, J = 9.51, 5.85 Hz, 1 H) 6.69 (s, 1 H) 6.84 (dd, J = 8.42, 1.83 Hz, 1 H) 7.11 (d, J = 7.68 Hz, 1 H) 7.39 (t, J = 7.32 Hz, 1 H) 7.46 (d, J = 1.83 Hz, 1 H) 7.47-7.53 (m, 2 H) 7.72 (d, J = 7.68 Hz, 1 H) 8.44 (s, 1 H) |
| 16 | (360 MHz, CDCl$_3$) δ ppm 1.87-2.47 (m, 4 H) 2.59 (s, 3 H) 3.90 (s, 3 H) 4.16-4.27 (m, 3 H) 7.04 (t, J = 8.60 Hz, 2 H) 7.11-7.19 (m, 2 H) 7.29-7.34 (m, 1 H) 7.36 (s, 1 H) 7.56 (d, J = 8.05 Hz, 1 H) 7.68 (d, J = 8.05 Hz, 1 H) 8.42-8.53 (m, 1 H) |
| 19 | (360 MHz, DMSO-d$_6$) δ ppm 2.14 (s, 3 H) 2.23 (s, 3 H) 3.76 (s, 3 H) 7.02 (s, 1 H) 7.07-7.18 (m, 2 H) 7.19-7.30 (m, 3 H) 7.43 (dd, J = 8.4, 5.9 Hz, 1 H) 7.51 (dd, J = 7.3, 1.1 Hz, 1 H) 7.65 (d, J = 7.3 Hz, 2 H) 8.84 (dd, J = 6.6, 0.7 Hz, 1 H) 9.96 (s, 1 H) |
| 28 | (360 MHz, CDCl$_3$) δ ppm 1.99-2.25 (m, 3 H) 2.29 (s, 3 H) 2.31-2.42 (m, 1 H) 3.81 (s, 3 H) 4.22 (t, J = 5.9 Hz, 2 H) 4.64 (t, J = 6.6 Hz, 1 H) 6.65 (s, 1 H) 6.84 (s, 1 H) 6.90 (dd, J = 8.4, 2.2 Hz, 1 H) 6.95-7.04 (m, 1 H) 7.12 (d, J = 8.4 Hz, 1 H) 7.17-7.25 (m, 2 H) 7.34 (d, J = 2.2 Hz, 1 H) 7.38-7.46 (m, 1 H) 7.59 (s, 1 H) |
| 31 | (360 MHz, CDCl$_3$) δ ppm 1.85-2.00 (m, 1 H) 2.08-2.23 (m, 1 H) 2.23-2.34 (m, 4 H) 2.39-2.51 (m, 1 H) 3.80 (s, 3 H) 4.15-4.33 (m, 2 H) 4.57 (dd, J = 9.5, 5.9 Hz, 1 H) 6.67 (s, 1 H) 6.83 (t, J = 1.1 Hz, 1 H) 6.87 (dd, J = 8.6, 2.4 Hz, 1 H) 7.06-7.15 (m, 2 H) 7.33 (d, J = 2.2 Hz, 1 H) 7.39 (t, J = 7.5 Hz, 1 H) 7.50 (t, J = 7.1 Hz, 1 H) 7.58 (d, J = 1.1 Hz, 1 H) 7.71 (d, J = 8.1 Hz, 1 H) |
| 41 | (360 MHz, CDCl$_3$) δ ppm 1.97-2.25 (m, 3 H) 2.30-2.41 (m, 1 H) 2.60 (s, 3 H) 4.23 (t, J = 5.85 Hz, 2 H) 4.65 (t, J = 6.40 Hz, 1 H) 6.70 (s, 1 H) 6.92-7.02 (m, 1 H) 7.17-7.25 (m, 2 H) 7.29 (dd, J = 5.49, 1.46 Hz, 1 H) 7.34 (s, 1 H) 7.38-7.46 (m, 1 H) 7.52 (m, 2 H) 7.59 (m, 2 H) 8.49 (d, J = 5.49 Hz, 1 H) |
| 42 | (360 MHz, CDCl$_3$) δ ppm 1.85-1.99 (m, 1 H) 2.08-2.22 (m, 1 H) 2.22-2.33 (m, 1 H) 2.38-2.50 (m, 1 H) 2.60 (s, 3 H) 4.18-4.36 (m, 2 H) 4.58 (dd, J = 9.1, 5.9 Hz, 1 H) 6.69 (s, 1 H) 7.11 (d, J = 7.7 Hz, 1 H) 7.29 (dd, J = 5.1, 1.8 Hz, 1 H) 7.34 (d, J = 1.8 Hz, 1 H) 7.39 (t, J = 7.7 Hz, 1 H) 7.45-7.54 (m, 3 H) 7.55-7.63 (m, 2 H) 7.72 (d, J = 7.7 Hz, 1 H) 8.49 (d, J = 5.1 Hz, 1 H) |

| Co. No. | NMR result |
| --- | --- |
| 43 | (360 MHz, CDCl₃) δ ppm 1.86-2.00 (m, 1 H) 2.06-2.22 (m, 1 H) 2.22-2.35 (m, 1 H) 2.38-2.51 (m, 1 H) 2.58 (s, 3 H) 3.82 (s, 3 H) 4.16-4.36 (m, 2 H) 4.58 (dd, J = 9.1, 5.9 Hz, 1 H) 6.66 (s, 1 H) 6.92 (dd, J = 8.4, 2.2 Hz, 1 H) 7.11 (d, J = 7.7 Hz, 1 H) 7.24 (d, J = 8.4 Hz, 1 H) 7.26-7.29 (m, 1 H) 7.29-7.33 (m, 2 H) 7.39 (t, J = 7.7 Hz, 1 H) 7.50 (t, J = 7.7 Hz, 1 H) 7.72 (d, J = 7.3 Hz, 1 H) 8.46 (d, J = 5.1 Hz, 1 H) |
| 62 | (360 MHz, DMSO-d₆) δ ppm 2.01-2.19 (m, 1 H) 2.39-2.48 (m, 1 H) 2.74 (s, 3 H) 3.03 (dd, J = 16.6, 4.9 Hz, 1 H) 3.14 (dd, J = 16.6, 11.2 Hz, 1 H) 3.40-3.58 (m, 1 H) 3.87 (s, 3 H) 4.09-4.21 (m, 1 H) 4.22-4.31 (m, 1 H) 7.39 (dd, J = 8.6, 2.0 Hz, 1 H) 7.46-7.55 (m, 2 H) 7.63 (d, J = 8.4 Hz, 1 H) 7.69-7.80 (m, 2 H) 7.80-7.87 (m, 1 H) 8.05 (dd, J = 6.4, 1.6 Hz, 1 H) 8.09 (d, J = 1.6 Hz, 1 H) 8.63 (d, J = 6.6 Hz, 1 H) 9.86 (s, 1 H) |
| 65 | (360 MHz, CDCl₃) δ ppm 2.58 (s, 3 H) 3.83 (s, 3 H) 4.14-4.31 (m, 2 H) 4.35-4.55 (m, 2 H) 6.14 (s, 1 H) 6.69 (s, 1 H) 6.92 (dd, J = 8.2, 2.0 Hz, 1 H) 7.19-7.35 (m, 4 H) 7.40 (d, J = 7.3 Hz, 1 H) 7.45-7.64 (m, 2 H) 7.77 (d, J = 7.0 Hz, 1 H) 8.46 (d, J = 5.1 Hz, 1 H) |
| 66 | (360 MHz, CDCl₃) δ ppm 1.98-2.25 (m, 3 H) 2.27-2.45 (m, 1 H) 2.58 (s, 3 H) 3.83 (s, 3 H) 4.22 (t, J = 5.9 Hz, 2 H) 4.65 (t, J = 6.6 Hz, 1 H) 6.66 (s, 1 H) 6.95 (dd, J = 8.4, 1.5 Hz, 1 H) 6.98-7.04 (m, 1 H) 7.18-7.35 (m, 6 H) 7.36-7.46 (m, 1 H) 8.46 (d, J = 5.1 Hz, 1 H) |
| 68 | (360 MHz, CDCl₃) δ ppm 1.98-2.24 (m, 3 H) 2.28-2.42 (m, 1 H) 2.60 (s, 3 H) 4.23 (t, J = 5.85 Hz, 2 H) 4.65 (t, J = 6.40 Hz, 1 H) 6.78 (s, 1 H) 6.92-7.02 (m, 1 H) 7.18-7.25 (m, 2 H) 7.29 (dd, J = 5.49, 1.46 Hz, 1 H) 7.34 (s, 1 H) 7.38-7.45 (m, 1 H) 7.51 (m, 2 H) 7.59 (m, 2 H) 8.48 (d, J = 5.49 Hz, 1 H) |
| 73 | (360 MHz, CDCl₃) δ ppm 1.98-2.24 (m, 3 H) 2.28-2.45 (m, 1 H) 2.61 (s, 3 H) 4.23 (t, J = 5.85 Hz, 2 H) 4.66 (t, J = 6.40 Hz, 1 H) 6.70 (s, 1 H) 6.93-7.04 (m, 1 H) 7.17-7.25 (m, 2 H) 7.29 (dd, J = 5.49, 1.46 Hz, 1 H) 7.35 (s, 1 H) 7.38-7.45 (m, 1 H) 7.52 (m, 2 H) 7.59 (m, 2 H) 8.49 (d, J = 5.49 Hz, 1 H) |
| 75 | (360 MHz, CDCl₃) δ ppm 1.83-2.00 (m, 1 H) 2.06-2.23 (m, 1 H) 2.23-2.35 (m, 1 H) 2.37-2.52 (m, 1 H) 4.17-4.36 (m, 2 H) 4.58 (dd, J = 9.1, 5.9 Hz, 1 H) 6.72 (s, 1 H) 7.11 (d, J = 7.7 Hz, 1 H) 7.35-7.42 (m, 1 H) 7.45-7.54 (m, 5 H) 7.57-7.65 (m, 2 H) 7.72 (d, J = 7.7 Hz, 1 H) 8.60 (d, J = 5.5 Hz, 2 H) |
| 78 | (360 MHz, CDCl₃) δ ppm 1.99-2.26 (m, 3 H) 2.28-2.44 (m, 1 H) 2.58 (s, 3 H) 3.83 (s, 3 H) 4.22 (t, J = 5.9 Hz, 2 H) 4.65 (t, J = 6.6 Hz, 1 H) 6.69 (s, 1 H) 6.95 (dd, J = 8.4, 2.2 Hz, 1 H) 6.97-7.04 (m, 1 H) 7.19-7.25 (m, 3 H) 7.28 (dd, J = 5.1, 1.5 Hz, 1 H) 7.30-7.34 (m, 2 H) 7.36-7.46 (m, 1 H) 8.46 (d, J = 5.1 Hz, 1 H) |
| 81 | (360 MHz, CDCl₃) δ ppm 1.91-2.07 (m, 1 H) 2.08-2.27 (m, 2 H) 2.27-2.39 (m, 1 H) 2.60 (s, 3 H) 4.09-4.33 (m, 2 H) 4.41 (dd, J = 8.2, 6.0 Hz, 1 H) 6.68 (s, 1 H) 6.79-6.90 (m, 2 H) 6.98-7.09 (m, 1 H) 7.29 (d, J = 5.5 Hz, 1 H) 7.34 (s, 1 H) 7.45-7.55 (m, 2 H) 7.55-7.63 (m, 2 H) 8.49 (d, J = 5.1 Hz, 1 H) |
| 82 | (360 MHz, CDCl₃) δ ppm 1.94-2.07 (m, 1 H) 2.07-2.26 (m, 2 H) 2.27-2.39 (m, 1 H) 2.58 (s, 3 H) 3.83 (s, 3 H) 4.08-4.30 (m, 2 H) 4.41 (dd, J = 8.4, 5.9 Hz, 1 H) 6.66 (s, 1 H) 6.80-6.89 (m, 2 H) 6.95 (dd, J = 8.4, 2.2 Hz, 1 H) 6.98-7.11 (m, 1 H) 7.24 (d, J = 8.4 Hz, 1 H) 7.26-7.29 (m, 1 H) 7.29-7.33 (m, 2 H) 8.46 (d, J = 5.1 Hz, 1 H) |
| 87 | (360 MHz, CDCl₃) δ ppm 2.58 (s, 3 H) 3.84 (s, 3 H) 4.14-4.28 (m, 2 H) 4.33-4.46 (m, 2 H) 6.20 (s, 1 H) 6.69 (s, 1 H) 6.94 (dd, J = 8.2, 2.0 Hz, 1 H) 7.22-7.39 (m, 7 H) 7.47 (d, J = 7.7 Hz, 1 H) 8.46 (d, J = 5.1 Hz, 1 H) |
| 90 | (360 MHz, CDCl₃) δ ppm 1.84-1.99 (m, 1 H) 2.00-2.15 (m, 1 H) 2.15-2.34 (m, 2 H) 2.38 (s, 3 H) 2.60 (s, 3 H) 4.23 (t, J = 5.9 Hz, 2 H) 4.31-4.40 (m, 1 H) 6.71 (s, 1 H) 6.81-6.88 (m, 2 H) 6.92 (d, J = 9.5 Hz, 1 H) 7.29 (dd, J = 5.5, 1.1 Hz, 1 H) 7.34 (s, 1 H) 7.46-7.55 (m, 2 H) 7.55-7.63 (m, 2 H) 8.49 (d, J = 5.1 Hz, 1 H) |
| 91 | (360 MHz, CDCl₃) δ ppm 1.82-1.99 (m, 1 H) 1.99-2.16 (m, 1 H) 2.16-2.35 (m, 2 H) 2.38 (s, 3 H) 2.58 (s, 3 H) 3.84 (s, 3 H) 4.22 (t, J = 5.9 Hz, 2 H) 4.35 (dd, J = 7.7, 5.9 Hz, 1 H) 6.66 (s, 1 H) 6.83-6.88 (m, 2 H) 6.89-6.98 (m, 2 H) 7.19-7.34 (m, 4 H) 8.46 (d, J = 5.5 Hz, 1 H) |
| 98 | (360 MHz, CDCl₃) δ ppm 1.80-2.02 (m, 1 H) 2.05-2.22 (m, 1 H) 2.22-2.34 (m, 1 H) 2.36-2.51 (m, 1 H) 2.60 (s, 3 H) 4.10-4.36 (m, 2 H) 4.58 (dd, J = 8.8, 5.9 Hz, 1 H) 6.71 (s, 1 H) 7.11 (d, J = 7.7 Hz, 1 H) 7.28 (dd, J = 5.1, 1.8 Hz, 1 H) 7.34 (s, 1 H) 7.39 (t, J = 7.7 Hz, 1 H) 7.45-7.53 (m, 3 H) 7.54-7.62 (m, 2 H) 7.72 (d, J = 7.7 Hz, 1 H) 8.49 (d, J = 5.5 Hz, 1 H) |
| 181 | (360 MHz, DMSO-d₆) δ ppm 1.42-1.60 (m, 1 H) 1.65-1.81 (m, 1 H) 1.81-1.91 (m, 1 H) 1.96-2.09 (m, 1 H) 2.61-2.73 (m, 1 H) 2.74 (s, 3 H) 2.76-2.87 (m, 2 H) 3.92 (s, 3H) 4.14-4.23 (m, 1 H) 4.35-4.46 (m, 1 H) 6.89-7.01 (m, 2 H) 7.43 (dd, J = 8.6, 2.0 Hz, 1 H) 7.63 (d, J = 8.8 Hz, 1 H) 7.78 (d, J = 1.8 Hz, 1 H) 8.06 (dd, J = 6.6, 1.8 Hz, 1 H) 8.10 (d, J = 1.8 Hz, 1 H) 8.39 (dd, J = 5.9, 1.5 Hz, 1 H) 8.64 (d, J = 6.6 Hz, 1 H) 10.18 (s, 1 H) |

Pharmacology

A) Screening of the Compounds of the Invention for γ-Secretase-Modulating Activity Screening was carried out using SKNBE2 cells carrying the APP 695—wild type, grown in Dulbecco's Modified Eagle's Medium/Nutrient mixture F-12 (DMEM/NUT-mix F-12) (HAM) provided by Invitrogen (cat no. 10371-029) containing 5% Serum/Fe supplemented with 1% non-essential amino acids, 1-glutamine 2 mM, Hepes 15 mM, penicillin 50 U/ml (units/ml) en streptomycin 50 μg/ml. Cells were grown to near confluency.

The screening was performed using a modification of the assay as described in Citron et al (1997) Nature Medicine 3: 67. Briefly, cells were plated in a 384-well plate at $10^4$ cells/well in Ultraculture (Lonza, BE12-725F) supplemented with 1% glutamine (Invitrogen, 25030-024), 1% non-essential amino acid (NEAA), penicillin 50 U/ml en streptomycin 50 µg/ml in the presence of test compound at different test concentrations. The cell/compound mixture was incubated overnight at 37° C., 5% $CO_2$. The next day the media were assayed by two sandwich immuno-assays, for Aβ42 and Aβtotal.

Aβtotal and Aβ42 concentrations were quantified in the cell supernatant using the Aphalisa technology (Perkin Elmer). Alphalisa is a sandwich assay using biotinylated antibody attached to streptavidin coated donorbeads and antibody conjugated to acceptor beads. In the presence of antigen, the beads come into close proximity. The excitation of the donor beads provokes the release of singlet oxygen molecules that trigger a cascade of energy transfer in the acceptor beads, resulting in light emission. To quantify the amount of Aβ42 in the cell supernatant, monoclonal antibody specific to the C-terminus of Aβ42 (JRF/cAβ42/26) was coupled to the receptor beads and biotinylated antibody specific to the N-terminus of Aβ (JRF/AβN/25) was used to react with the donor beads. T quantify the amount of Aβtotal in the cell supernatant, monoclonal antibody specific to the N-terminus of Aβ (JRF/AβN/25) was coupled to the receptor beads and biotinylated antibody specific to the mid region of Aβ (biotinylated 4G8) was used to react with the donor beads.

To obtain the values reported in Table 3, the data are calculated as percentage of the maximum amount of amyloid Beta 42 measured in the absence of the test compound. The sigmoidal dose response curves were analyzed using non-linear regression analysis with percentage of the control plotted against the log concentration of the compound. A 4-parameter equation was used to determine the $IC_{50}$.

TABLE 3

| Co. No. | IC50 Aβ42 (µM) | IC50 Aβtotal (µM) |
| --- | --- | --- |
| 1 | 0.016 | 7.762 |
| 2 | 0.007 | >10 |
| 3 | 0.019 | >10 |
| 4 | 0.022 | >10 |
| 5 | 0.018 | >10 |
| 6 | 0.007 | 7.41 |
| 7 | 0.007 | >10 |
| 8 | 0.032 | 7.59 |
| 9 | 0.065 | >10 |
| 10 | 0.009 | >10 |
| 11 | n.d. | n.d. |
| 12 | n.d. | n.d. |
| 13 | 0.009 | 7.762 |
| 14 | 0.066 | >10 |
| 15 | 0.079 | >10 |
| 16 | 0.363 | >10 |
| 17 | 0.295 | >10 |
| 18 | 0.112 | >10 |
| 19 | 0.004 | 3.72 |
| 20 | 0.005 | 5.89 |
| 21 | 0.115 | >10 |
| 22 | 0.040 | 7.586 |
| 23 | 0.013 | >10 |
| 24 | 0.126 | >10 |
| 25 | 0.015 | >10 |
| 26 | 0.043 | >10 |
| 27 | 0.014 | 8.51 |
| 28 | 0.016 | 5.13 |
| 29 | 0.025 | >10 |
| 30 | 0.049 | >10 |
| 31 | 0.013 | 5.75 |
| 32 | 0.012 | 9.333 |
| 33 | 4.467 | >10 |
| 34 | 0.010 | 7.586 |
| 35 | 0.031 | >10 |
| 36 | 0.501 | >10 |
| 37 | 0.174 | 6.31 |
| 38 | 0.029 | >10 |
| 39 | 0.110 | 8.13 |
| 40 | 0.039 | >10 |
| 41 | 0.028 | >10 |
| 42 | 0.023 | >10 |
| 43 | 0.016 | 7.08 |
| 44 | 0.039 | >10 |
| 45 | 0.145 | >10 |
| 46 | 5.248 | >10 |
| 47 | 0.055 | >10 |
| 48 | 0.030 | 5.75 |
| 49 | 0.029 | >10 |
| 50 | 0.019 | 8.13 |
| 51 | 0.062 | >10 |
| 52 | 0.182 | 10 |
| 62 | 0.123 | >10 |
| 63 | 0.019 | 8.13 |
| 65 | 0.052 | >10 |
| 66 | 0.035 | 9.12 |
| 68 | 0.043 | >10 |
| 72 | 0.023 | 4.571 |
| 73 | 0.044 | >10 |
| 74 | 0.015 | 7.41 |
| 75 | 0.257 | >10 |
| 76 | 0.046 | >10 |
| 77 | 0.040 | >10 |
| 78 | 0.032 | >10 |
| 79 | 0.071 | >10 |
| 80 | 0.036 | >10 |
| 81 | 0.069 | >10 |
| 82 | 0.039 | >10 |
| 83 | 0.095 | >10 |
| 84 | 0.042 | >10 |
| 85 | 0.044 | >10 |
| 86 | 0.048 | >10 |
| 87 | 0.035 | >10 |
| 88 | 0.036 | 9.33 |
| 89 | 0.032 | 9.12 |
| 90 | 0.056 | >10 |
| 91 | 0.025 | 8.51 |
| 92 | 0.021 | >10 |
| 93 | 0.043 | >10 |
| 94 | 0.056 | >10 |
| 95 | 0.045 | >10 |
| 96 | 0.022 | >10 |
| 97 | 0.046 | >10 |
| 98 | 0.047 | >10 |
| 99 | 0.050 | >10 |
| 100 | 0.036 | >10 |
| 101 | 0.044 | >10 |
| 102 | 0.029 | >10 |
| 103 | 0.059 | >10 |
| 104 | 0.056 | >10 |
| 105 | 0.056 | >10 |
| 106 | 0.040 | >15 |
| 107 | 0.032 | >15 |
| 110 | 0.050 | >10 |
| 111 | 0.056 | >10 |
| 114 | 0.041 | >10 |
| 115 | 0.041 | >10 |
| 116 | 0.071 | >10 |
| 144 | 0.028 | >10 |
| 151 | 0.031 | 7.08 |
| 172 | 0.038 | >10 |
| 181 | 0.016 | 3.98 |
| 182 | 0.044 | >10 |
| 183 | 0.041 | >10 |
| 184 | 0.023 | >10 |
| 185 | 0.028 | >10 |
| 186 | 1.096 | >10 |
| 187 | 1.622 | >10 |

B) Demonstration of In Vivo Efficacy

Aβ42 lowering agents of the invention can be used to treat AD in mammals such as humans or alternatively demonstrating efficacy in animal models such as, but not limited to, the mouse, rat, or guinea pig. The mammal may not be diagnosed with AD, or may not have a genetic predisposition for AD, but may be transgenic such that it overproduces and eventually deposits Aβ in a manner similar to that seen in humans afflicted with AD.

Aβ42 lowering agents can be administered in any standard form using any standard method. For example, but not limited to, Aβ42 lowering agents can be in the form of liquid, tablets or capsules that are taken orally or by injection. Aβ42 lowering agents can be administered at any dose that is sufficient to significantly reduce levels of Aβ42 in the blood, blood plasma, serum, cerebrospinal fluid (CSF), or brain.

To determine whether acute administration of an Aβ42 lowering agent would reduce Aβ42 levels in vivo, non-transgenic rodents, e.g. mice or rats were used. Animals treated with the Aβ42 lowering agent were examined and compared to those untreated or treated with vehicle and brain levels of soluble Aβ42 and total Aβ were quantitated by standard techniques, for example, using ELISA. Treatment periods varied from hours (h) to days and were adjusted based on the results of the Aβ42 lowering once a time course of onset of effect could be established.

A typical protocol for measuring Aβ42 lowering in vivo is shown but it is only one of many variations that could be used to optimize the levels of detectable Aβ. For example, Aβ42 lowering compounds were formulated in 20% of Captisol® (a sulfobutyl ether of β-cyclodextrin) in water or 20% hydroxypropyl β cyclodextrin. The Aβ42 lowering agents were administered as a single oral dose or by any acceptable route of administration to overnight fasted animals. After 4 h, the animals were sacrificed and Aβ42 levels were analysed.

Blood was collected by decapitation and exsanguinations in EDTA-treated collection tubes. Blood was centrifuged at 1900 g for 10 minutes (min) at 4° C. and the plasma recovered and flash frozen for later analysis. The brain was removed from the cranium and hindbrain. The cerebellum was removed and the left and right hemisphere were separated. The left hemisphere was stored at −18° C. for quantitative analysis of test compound levels. The right hemisphere was rinsed with phosphate-buffered saline (PBS) buffer and immediately frozen on dry ice and stored at −80° C. until homogenization for biochemical assays.

Mouse brains from non-transgenic animals were resuspended in 8 volumes of 0.4% DEA (diethylamine)/50 mM NaCl containing protease inhibitors (Roche-11873580001 or 04693159001) per gram of tissue, e.g. for 0.158 g brain, add 1.264 ml of 0.4% DEA. All samples were homogenized in the FastPrep-24 system (MP Biomedicals) using lysing matrix D (MPBio #6913-100) at 6 m/s for 20 seconds. Homogenates were centrifuged at 221.300×g for 50 min. The resulting high speed supernatants were then transferred to fresh eppendorf tubes. Nine parts of supernatant were neutralized with 1 part 0.5 M Tris-HCl pH 6.8 and used to quantify Aβtotal and Aβ42.

To quantify the amount of Aβtotal and Aβ42 in the soluble fraction of the brain homogenates, Enzyme-Linked-Immunosorbent-Assays were used. Briefly, the standards (a dilution of synthetic Aβ1-40 and Aβ1-42, Bachem) were prepared in 1.5 ml Eppendorf tube in Ultraculture, with final concentrations ranging from 10000 to 0.3 pg/ml. The samples and standards were co-incubated with HRPO-labelled N-terminal antibody for Aβ42 detection and with the biotinylated mid-domain antibody 4G8 for Aβtotal detection. 50 μl of conjugate/sample or conjugate/standards mixtures were then added to the antibody-coated plate (the capture antibodies selectively recognize the C-terminal end of Aβ42, antibody JRF/cAβ42/26, for Aβ42 detection and the N-terminus of Aβ, antibody JRF/rAβ/2, for Aβtotal detection). The plate was allowed to incubate overnight at 4° C. in order to allow formation of the antibody-amyloid complex. Following this incubation and subsequent wash steps the ELISA for Aβ42 quantification was finished by addition of Quanta Blu fluorogenic peroxidase substrate according to the manufacturer's instructions (Pierce Corp., Rockford, Il). A reading was performed after 10 to 15 min (excitation 320 nm/emission 420 nm).

For Aβtotal detection, a Streptavidine-Peroxidase-Conjugate was added, followed 60 min later by an additional wash step and addition of Quanta Blu fluorogenic peroxidase substrate according to the manufacturer's instructions (Pierce Corp., Rockford, Ill). A reading was performed after 10 to 15 min (excitation 320 nm/emission 420 nm).

In this model at least 20% Aβ42 lowering compared to untreated animals would be advantageous.

The results are shown in Table 4 (dose 30 mg/kg oral dosing) (value for untreated animals as control (Ctrl) was set at 100):

| Co. No. | Aβ42 (% vs Ctrl)_Mean | Aβtotal (% vs Ctrl)_Mean |
|---|---|---|
| 3 | 75 | 95 |
| 13 | 93 | 100 |
| 14 | 101 | 119 |
| 43 | 71 | 87 |
| 42 | 58 | 83 |
| 31 | 83 | 96 |
| 52 | 45 | 112 |
| 46 | 61 | 98 |
| 41 | 54 | 102 |
| 58 | 88 | 89 |
| 54 | 46 | 88 |
| 28 | 81 | 93 |
| 29 | 99 | 98 |
| 59 | 69 | 94 |
| 65 | 64 | 101 |
| 66 | 54 | 92 |
| 67 | 60 | 89 |
| 68 | 51 | 90 |
| 73 | 55 | 99 |
| 69 | 63 | 97 |
| 82 | 47 | 89 |
| 81 | 41 | 84 |
| 140 | 83 | 86 |
| 141 | 78 | 98 |
| 185 | 52 | 96 |
| 90 | 38 | 83 |
| 91 | 51 | 92 |
| 105 | 51 | 99 |
| 160 | 77 | 83 |
| 133 | 67 | 94 |
| 87 | 48 | 89 |
| 108 | 70 | 94 |
| 109 | 85 | 117 |
| 78 | 46 | 103 |

Composition Examples

"Active ingredient" (a.i.) as used throughout these examples relates to a compound of Formula (I), including any stereochemically isomeric form thereof, a pharmaceutically acceptable salt thereof or a solvate thereof; in particular to any one of the exemplified compounds.

Typical examples of recipes for the formulation of the invention are as follows:

1. Tablets

| Active ingredient | 5 to 50 mg |
|---|---|
| Di-calcium phosphate | 20 mg |
| Lactose | 30 mg |
| Talcum | 10 mg |
| Magnesium stearate | 5 mg |
| Potato starch | ad 200 mg |

2. Suspension

An aqueous suspension is prepared for oral administration so that each milliliter contains 1 to 5 mg of active ingredient, 50 mg of sodium carboxymethyl cellulose, 1 mg of sodium benzoate, 500 mg of sorbitol and water ad 1 ml.

3. Injectable

A parenteral composition is prepared by stirring 1.5% (weight/volume) of active ingredient in 0.9% NaCl solution or in 10% by volume propylene glycol in water.

4. Ointment

| Active ingredient | 5 to 1000 mg |
|---|---|
| Stearyl alcohol | 3 g |
| Lanoline | 5 g |
| White petroleum | 15 g |
| Water | ad 100 g |

In this Example, active ingredient can be replaced with the same amount of any of the compounds according to the present invention, in particular by the same amount of any of the exemplified compounds.

Reasonable variations are not to be regarded as a departure from the scope of the invention. It will be obvious that the thus described invention may be varied in many ways by those skilled in the art.

The invention claimed is:

1. A compound of Formula (I)

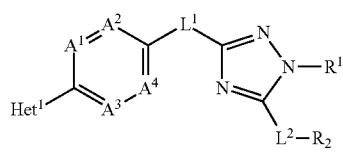

(I)

or a stereoisomeric form thereof, wherein
Het$^1$ is a heterocycle, having formula (a-3a),

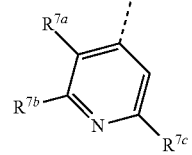

(a-3a)

$R^{7a}$ is hydrogen or $C_{1-4}$alkyl;
$R^{7b}$ and $R^{7c}$ each independently are hydrogen or $C_{1-4}$alkyl;
$A^1$ is $CR^9$; wherein $R^9$ is hydrogen, halo, or $C_{1-4}$alkyloxy;
$A^2$, $A^3$, and $A^4$ are CH;
$L^1$ is $NR^{10}$;
wherein $R^{10}$ is hydrogen or $C_{1-4}$alkyl;
$R^1$ and -$L^2$-$R^2$ are taken together to form a bivalent radical —$R^{1'}$—$R^2$-$L^2$-having formula (b-1) or (b-2)

$$-(CH_2)_{m-n}-Y-(CH_2)_n- \qquad (b\text{-}1);$$

$$-(CH_2)_n-Y-(CH_2)_{m-n}- \qquad (b\text{-}2);$$

wherein (b-1) or (b-2) may be substituted on one carbon atom with one aryl$^1$ substituent;
Y is O
m is 3
n is 1;
wherein $R^1$, the nitrogen atom to which $R^1$ is attached, -$L^2$-$R^2$, and the carbon atom to which $L^2$ is attached together form a six-membered ring;
aryl$^1$ is phenyl optionally substituted with one or more substituents each independently selected from the group consisting of halo, $C_{1-4}$alkyloxy, and $C_{1-4}$alkyl optionally substituted with one or more halo substituents;
each $R^{11e}$ and $R^{11f}$ independently is hydrogen, $C_{1-4}$ alkyl or $C_{1-4}$alkylcarbonyl;
each $R^{12e}$ and $R^{12f}$ independently is hydrogen or $C_{1-4}$alkyl;
$R^{13d}$ is hydrogen, or $C_{1-4}$alkyl optionally substituted with one or more substituents each independently selected from the group consisting of halo and cyclo $C_{3-7}$alkyl;
or a pharmaceutically acceptable addition salt thereof.

2. A pharmaceutical composition comprising a pharmaceutically acceptable carrier and, as active ingredient, a therapeutically effective amount of a compound as defined claim 1.

3. A method for the treatment of a patient for a disease or condition selected from Alzheimer's disease, traumatic brain injury, mild cognitive impairment, senility, dementia, dementia with Lewy bodies, cerebral amyloid angiopathy, multi-infarct dementia, dementia pugilistica, Down's syndrome, dementia associated with Parkinson's disease and dementia associated with beta-amyloid comprising administering to said patient a therapeutically effective amount of the compound of claim 1.

4. The method according to claim 3 wherein the disease is Alzheimer's disease.

* * * * *